United States Patent
Schäfer et al.

(10) Patent No.: US 9,353,065 B2
(45) Date of Patent: May 31, 2016

(54) HETEROCYCLIC BRIDGED BIPHENYLS

(75) Inventors: Thomas Schäfer, Liestal (CH); Peter Murer, Oberwil (CH); Frédérique Wendeborn, Ranspach-le-Haut (FR); Beat Schmidhalter, Bubendorf (CH); Kristina Bardon, Waldshut (DE); Andrea Ricci, Basel (CH); Joern Pommerehne, Lörrach (DE)

(73) Assignee: BASF SE, Ludwigshafen (DE)

( * ) Notice: Subject to any disclaimer, the term of this patent is extended or adjusted under 35 U.S.C. 154(b) by 209 days.

(21) Appl. No.: 12/531,885

(22) PCT Filed: Mar. 19, 2008

(86) PCT No.: PCT/EP2008/053251
§ 371 (c)(1),
(2), (4) Date: Sep. 18, 2009

(87) PCT Pub. No.: WO2008/119666
PCT Pub. Date: Oct. 9, 2008

(65) Prior Publication Data
US 2010/0109514 A1  May 6, 2010

(30) Foreign Application Priority Data
Mar. 29, 2007  (EP) .................................. 07105221

(51) Int. Cl.
| | | |
|---|---|---|
| H01J 1/63 | (2006.01) | |
| C07D 235/02 | (2006.01) | |
| C07D 235/18 | (2006.01) | |
| C07D 241/38 | (2006.01) | |
| C07D 263/52 | (2006.01) | |
| C07D 403/14 | (2006.01) | |
| C07D 413/14 | (2006.01) | |
| H01L 51/00 | (2006.01) | |
| H01L 51/50 | (2006.01) | |

(52) U.S. Cl.
CPC ............ C07D 235/02 (2013.01); C07D 241/38 (2013.01); C07D 263/52 (2013.01); C07D 403/14 (2013.01); C07D 413/14 (2013.01); H01L 51/0071 (2013.01); H01L 51/5012 (2013.01)

(58) Field of Classification Search
None
See application file for complete search history.

(56) References Cited

U.S. PATENT DOCUMENTS

| | | | |
|---|---|---|---|
| 2001/0049067 A1* | 12/2001 | Mitsumori et al. .......... | 430/58.8 |
| 2004/0126619 A1 | 7/2004 | Nishita | |
| 2004/0209117 A1 | 10/2004 | Aziz et al. | |
| 2005/0264174 A1* | 12/2005 | Liao et al. ................ | 313/500 |
| 2006/0289882 A1 | 12/2006 | Nishimura et al. | |
| 2007/0029927 A1 | 2/2007 | Kawamura et al. | |

FOREIGN PATENT DOCUMENTS

| | | | | |
|---|---|---|---|---|
| JP | 02134644 A | * | 5/1990 | ............... G03G 5/06 |
| JP | 2001-023777 A | * | 1/2001 | ............. H05B 33/14 |
| WO | 2005/123737 A | | 12/2005 | |
| WO | 2006/063466 A | | 6/2006 | |
| WO | 2006/130598 A | | 12/2006 | |
| WO | 2007/059610 A | | 5/2007 | |
| WO | 2007/095753 A | | 8/2007 | |

OTHER PUBLICATIONS

Machine English translation of JP 2001-023777 A. Jun. 30, 2011.*
Pramick et al. Organometallics 2003, 22, 523-528.*
Human English translation of JP 2001-23777 A. Publication date Jan. 26, 2001.*
Gaurot et al., Elsevier Science Publishers B.V. GB, vol. 48, No. 24.
Patent Abstracts of Japan 09013025.
Patent Abstracts of Japan 2000323278.
Patent Abstracts of Japan 2001023777.
Patent Abstracts of Japan 2001118683.
Patent Abstracts of Japan 2002050473.
Patent Abstracts of Japan 2002367786.
Patent Abstracts of Japan 2003059670.
Extended European Search Report Dated Dec. 5, 2007.
Copending U.S. Appl. No. 12/223,139.
Copending U.S. Appl. No. 12/309,090.
Copending U.S. Appl. No. 12/310,737.
Copending U.S. Appl. No. 11/886,138.

* cited by examiner

Primary Examiner — J. L. Yang
(74) Attorney, Agent, or Firm — Shruti Costales

(57) ABSTRACT

The present invention relates to compounds of the formula (I), a process for their preparation and their use in organic light emitting diodes (OLEDs), especially as host for phosphorescent compounds. The hosts may function with phosphorescent materials to provide improved efficiency, stability, manufacturability, or special characteristics of electroluminescent devices.

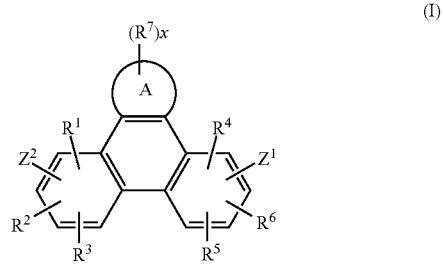

(I)

10 Claims, No Drawings

HETEROCYCLIC BRIDGED BIPHENYLS

The present invention relates to compounds of the formula

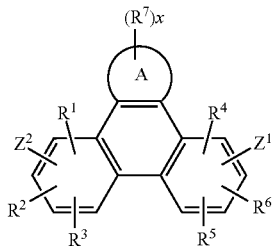

(I)

a process for their preparation and their use in organic light emitting diodes (OLEDs), especially as host for phosphorescent compounds. The hosts may function with phosphorescent materials to provide improved efficiency, stability, manufacturability, or spectral characteristics of electroluminescent devices.

WO2006063466 (WO2007/059610) discloses compounds of formula

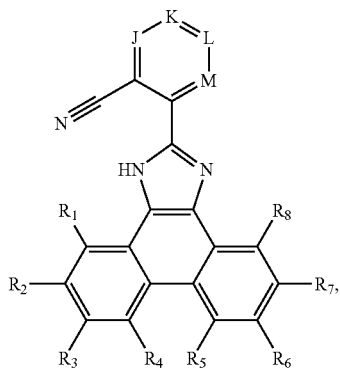

which are inhibitors of the microsomal prostaglandin E synthase-1 (mPGES-1) enzyme and are therefore useful to treat pain and/or inflammation from a variety of diseases or conditions.

WO2005/123737 relates to charge transport materials of formula

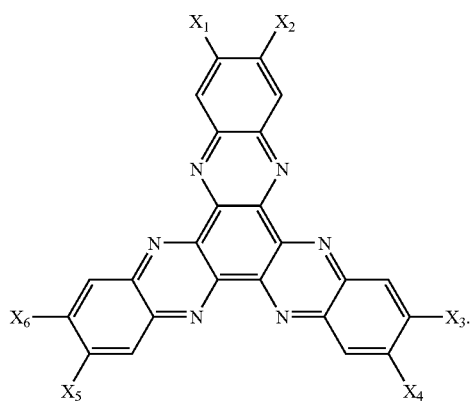

US20060289882 relates to an organic electroluminescent device, wherein the electron extracting layer may be formed of a hexaazatriphenylene derivative represented by the following structural formula

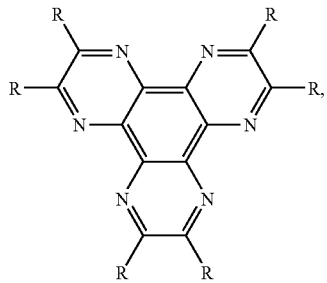

wherein R represents hydrogen, an alkyl group having a carbon number of 1 to 10, an alkyloxy group having a carbon number of 1 to 10, a dialkylamine group having a carbon number of 1 to 10, F, Cl, Br, I or CN.

US20070029927 discloses aromatic amine derivative represented by the following general formula (1):

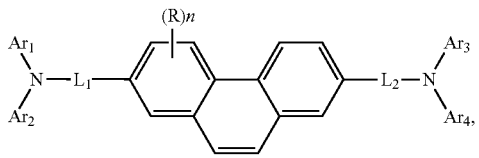

wherein $Ar_1$ to $Ar_4$ each independently represents a substituted or unsubstituted aryl group having 6 to 30 ring carbon atoms or a substituted or unsubstituted heteroaryl group having 5 to 30 ring carbon atoms;

$L_1$ and $L_2$ each independently represents a single bond, a substituted or unsubstituted arylene group having 6 to 30 ring carbon atoms or a substituted or unsubstituted heteroarylene group having 5 to 30 ring carbon atoms;

when both $L_1$ and $L_2$ are single bonds, however, a case where both $Ar_1$ and $Ar_3$ each represents a substituted or unsubstituted phenyl group and further, where both $Ar_2$ and $Ar_4$ each represents a substituted or unsubstituted biphenylyl group or a substituted or unsubstituted phenyl group is excluded; R represents a substituent and when R exists two or more, they may bond each other to form a ring; and n represents an integer of 0 to 8, and their use in organic electroluminescence devices.

US2004126619 relates to an electroluminescence devices, wherein the electron transporting organic material is at least one of compounds represented by the formula

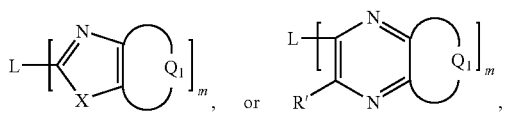

wherein X represents O, S, Se, Te or N—R, R represents a hydrogen atom, an aliphatic hydrocarbyl group, an aryl group or a heterocyclic group, $Q_1$ represents atoms necessary for forming an aromatic heterocyclic ring, m represents an integer of 2 or more, L represents a linking group; and R' represents a hydrogen atom or a substituent.

JP9013025 discloses an electroluminescent element, comprising a quinoxaline derivative represented by the formula

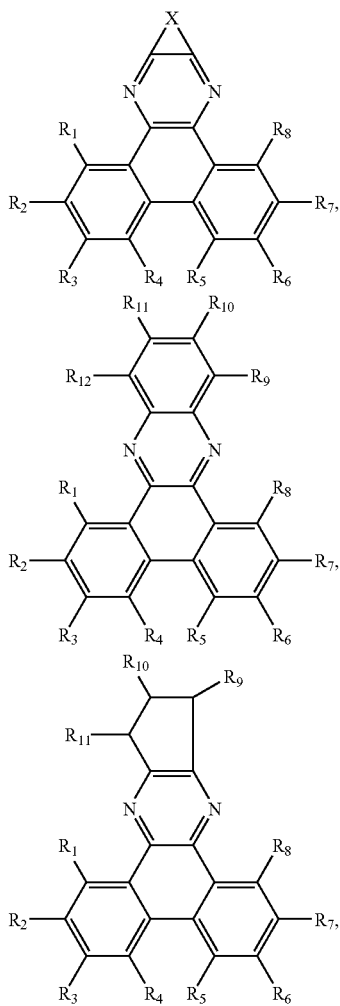

wherein X is a $C_{2-5}$(un)saturated alkylen, arylene or alkylarylene; $R_1$ to $R_8$, which are independent of each other, are each H, halogen, a $C_{1-6}$(perfluoro)alkyl, cyano, $R_1$ to $R_8$, which are independent of each other, are each H, $C_{1-6}$alkyl, $R_9$ to $R_{12}$ and $R_9$ to $R_{11}$ may form condensed rings when they are adjacent.

JP2000323278 relates to an emitter including an organic phosphor having an imidazole structure of the formula

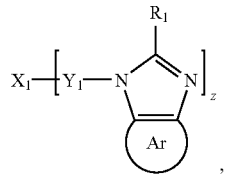

wherein $R_1$ may be either same or different respectively and selected from hydrogen, an alkyl group, a cycloalkyl group, an aralkyl group, an alkenyl group, a cycloalkenyl group, etc., $X_1$ is a bonding unit and selected from a substituted or non-substituted aromatic ring, heterocycle, a saturated fat chain, etc., $Y_1$ is selected from a single bond or a combination of either of single bond, an alkyl chain, an alkylene chain, an ether chain, etc., and Ar is selected from a substituted or non-substituted aromatic ring, heterocycle, etc. and z expresses a natural number. The organic phosphor is preferably a light emitting material having a guest material doped in a host material.

JP 2001023777 describes compounds of the formula

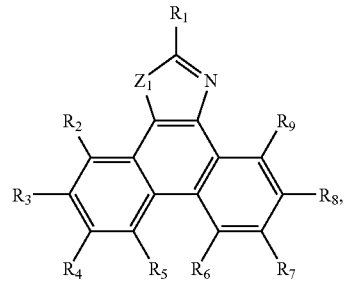

wherein $R_1$ to $R_9$ represent bonding, hydrogen, an alkyl group, a cycloalkyl group, an aralkyl group, an alkenyl group, a cycloalkenyl group, an alkoxy group, an alkylthio group, an arylether group, an aryl thioether group, an aryl group, a heterocyclic group, halogen, a cyano group, an aldehyde group, a carbonyl group, an ester group, a carbamoyl group, an amino group, a nitro group, a silyl group, a siloxyanyl group, and ring structure formed between adjacent substituting groups, and $Z_1$ represents oxygen, sulfur, nitrogen, or saturated hydrocarbon. The compounds having a phenanthroazole skeleton are suitable as a host material or a dopant material in a material of a hole transport layer, an electron transport layer, and a luminescent layer. No compounds, wherein any of $R_1$ to $R_9$ is an electron deficient heteroaryl group are explicitly disclosed.

JP2001118683 relates to a luminescent element, wherein the luminescent material is at least composed of a guest material and a host material and the peak of the emission spectrum of the host material is more than 300 nm and less than 460 nm. The following phenanthroazole compound is explicitly disclosed:

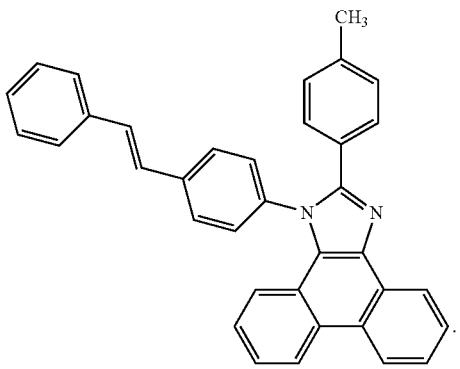 [SMILES: Cc1ccc(-c2nc3c4ccccc4c4ccccc4c3n2-c2ccc(/C=C/c3ccccc3)cc2)cc1]

JP2002050473 describes an element, in which a light emitting substance exists between a positive electrode and a negative electrode and which emits light by electric energy, and the element contains at least one kind of product formed by a photoreaction. The following phenanthroazole compound is explicitly disclosed:

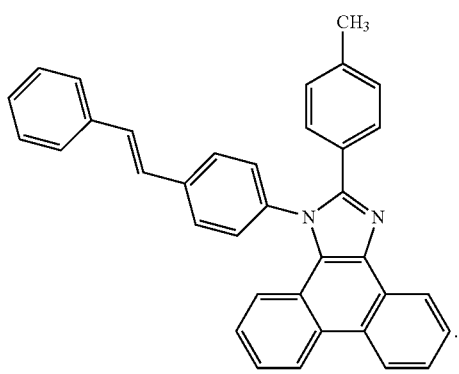 [SMILES: Cc1ccc(-c2nc3c4ccccc4c4ccccc4c3n2-c2ccc(/C=C/c3ccccc3)cc2)cc1]

JP2003059670 describes a light-emitting element having a structure in which at least a positive electrode, a luminous layer, an electron carrier layer, and a negative electrode are laminated in order, the electron carrier layer has an ionization potential 0.1 eV or more larger than the ionization potential of the luminous layer, and the material that mainly constitutes the luminous layer and the electron carrier layer is made of an organic compound having sublimation performance, and further, the organic compound that mainly constitutes the electron carrier layer has a molecular weight of 400 or more and a glass transition temperature of 90° C. or more. The following phenanthroazole compound is explicitly disclosed:

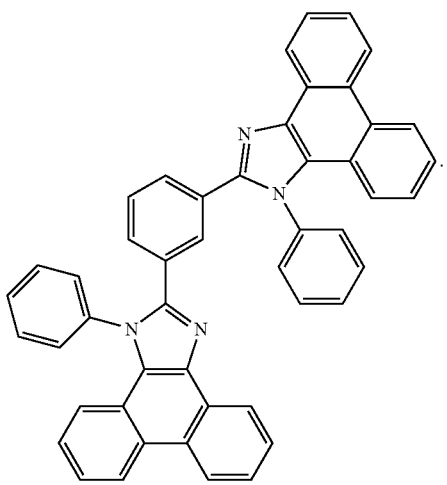 [SMILES: c1ccc(-n2c(-c3cccc(-c4nc5c6ccccc6c6ccccc6c5n4-c4ccccc4)c3)nc3c4ccccc4c4ccccc4c32)cc1]

JP2002367786 describes a luminous element having a sequentially laminated structure of at least a positive electrode, a luminous layer, a hole transport layer, an electron transport layer and a negative electrode, the relation between the luminous layer and the electron transport layer is (Ip (ETL)-Ip(EML))>(Ea(ETL)-Ea(EML)). The main material composing the luminous layer and the electron transport layer is made of an organic compound with sublimatic nature, and the main material composing the electron transport layer is an organic compound with molecular mass of not less than 400. [Ea: electron affinity (eV), Ip: ionization potential (eV), EML: luminous layer, and ETL: electron transport layer]. The following phenanthroazole compound is explicitly disclosed:

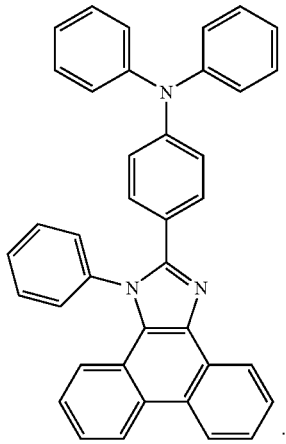 [SMILES: c1ccc(N(c2ccccc2)c2ccc(-c3nc4c5ccccc5c5ccccc5c4n3-c3ccccc3)cc2)cc1]

Notwithstanding these developments, there remains a need for new host materials, and especially hosts that will function with phosphorescent materials to provide improved efficiency, stability, manufacturability, or spectral characteristics of electroluminescent devices.

Accordingly, the present invention provides compounds of the formula

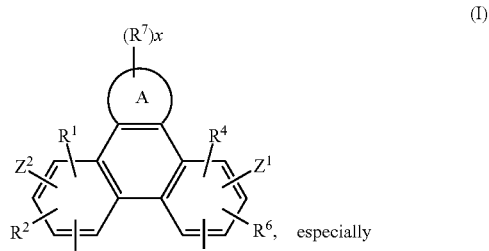

especially

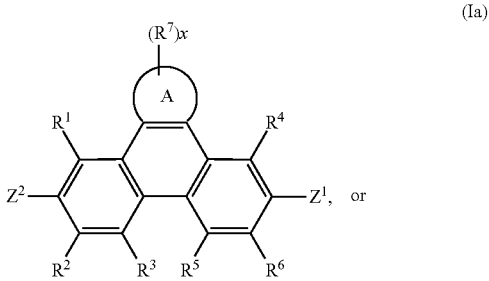

or

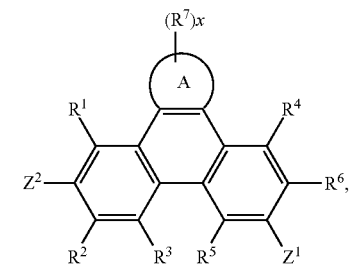

wherein A is a 5-, 6-, or 7-membered heteroaromatic ring, containing at least one heteroatom selected from nitrogen, oxygen and sulfur, especially one nitrogen atom and at least one further heteroatom selected from nitrogen, substituted nitrogen, oxygen and sulfur, with the proviso that, if the heteroatom is a group NR, R is different from a hydrogen atom, $Z^1$ and $Z^2$ are independently of each other a group Y, or -L-Y, wherein L is a linking group and Y is an electron deficient heteroaryl group, or $C_{10-30}$ aryl group, which may optionally be substituted, $R^1$, $R^2$, $R^3$, $R^4$, $R^5$ and $R^6$ are independently of each other hydrogen, F, or an organic substituent, or $R^1$ and $R^2$, $R^4$ and $R^6$, $R^2$ and $R^3$, $R^5$ and $R^3$ and/or $R^5$ and $R^6$, which are adjacent to each other, together form an aromatic, or heteroaromatic ring, or ring system, which can optionally be substituted, $R^7$ is an organic substituent, wherein two or more substituents $R^7$ in the same molecule may have different meanings, or can form together an aromatic, or heteroaromatic ring, or ring system, and x is 0, or an integer of 1 to 5.

The compounds of formula I can be used in organic light emitting diodes (OLEDs), especially as hosts for phosphorescent compounds. Accordingly, the present invention also provides an electroluminescent device comprising a cathode, an anode, and therebetween a light emitting layer containing a host material and a phosphorescent light-emitting material, wherein the host material is a compound of formula I.

The term "electron deficient heteroaryl group" means a group in which the isolated (unconnected) electron deficient heteroaryl unit has a HOMO of −5.5 eV or lower. Preferably at least one of $Z^1$ and $Z^2$, more preferably both of $Z^1$ and $Z^2$ are an electron deficient heteroaryl group.

The HOMO and LUMO energy levels for organic materials to be used in OLEDs have been estimated in several ways. The two common methods for estimating HOMO levels are solution electrochemistry and ultraviolet photoelectron spectroscopy (UPS). The most common method for determining oxidation and reduction potentials is cyclic voltametry, whereas the unknown is dissolved with a high concentration of electrolyte. Electrodes are inserted and the voltage scanned in either the positive or negative direction (depending on whether an oxidation or reduction is performed). The presence of a redox reaction is indicated by current flowing through the cell. The voltage scan is then reversed and the redox reaction is reversed. If the areas of the two redox waves are the same the process is reversible. The potential at which these events occur give the value of the reduction or oxidation potential relative to a reference. The reference can be an external one, such as Ag/AgCl or SCE, or it can be an internal one, such as ferrocene, which has a known oxidation potential.

Although this is a solution process, in contrast to the solid state OLED, and the reference may be hard to adjust to give values relative to vacuum, the method is good for giving relative numbers. One useful parameter that may come from the electrochemical measurement is the carrier gap. If both the reduction and oxidation are reversible, one can determine the energy difference between the hole and the electron. This value is important to determine the LUMO energy from a well defined HOMO energy.

The preferred method to estimate HOMO energies in the solid state is UPS. This is a photoelectric measurement, where the solid is irradiated with UV photons. The energy of the photons is gradually increased until photo-generated electrons are evolved. The onset of ejected electrons gives the energy of the HOMO. The best accepted method for determining HOMO energies is UPS, which gives values in eV relative to vacuum. This is the binding energy for the electron.

A first energy level (HOMO or LUMO) is considered "less than" or "lower" than a second energy level if it is lower on a conventional energy level diagram, which means that the first energy level would have a value that is more negative than the second energy level.

Examples of $Z^1$ and $Z^2$ are

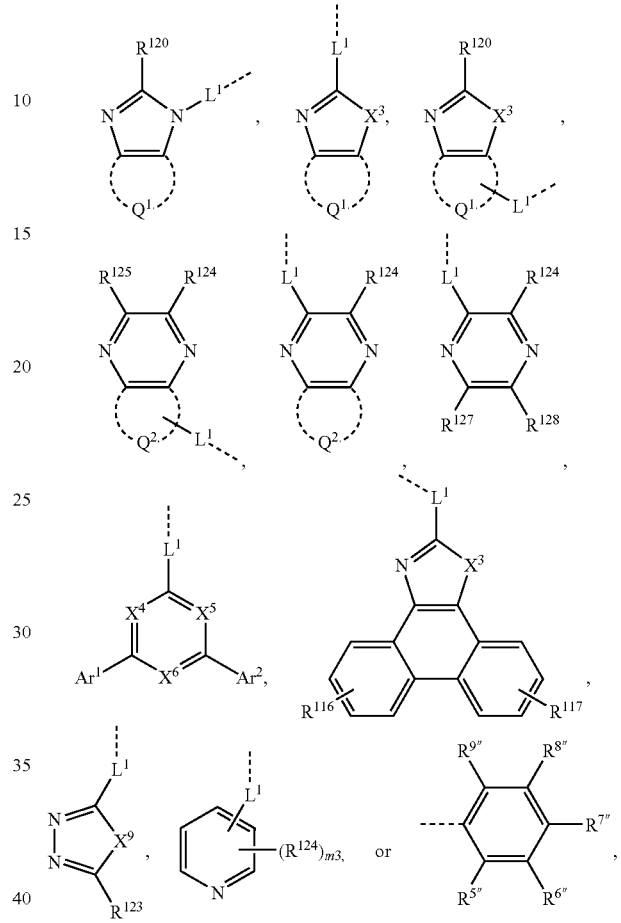

wherein
$R^{5''}$ is hydrogen, or has the meaning of $R^6$,
$R^{6''}$, $R^{7''}$, $R^{8''}$ and $R^{9''}$ are independently of each other $C_6$-$C_{18}$aryl; which may optionally be substituted by G; or $C_2$-$C_{20}$heteroaryl, which may optionally be substituted by G,
$X^3$ represents O, S or N—$R^{121'}$, especially N—$R^{121'}$,
$X^9$ represents O, S or N—$R^{121'}$, especially O,
$Q^1$ and $Q^2$ represents atoms necessary for forming a carbocyclic aromatic, or heterocyclic aromatic ring, which can optionally be condensed with other ring(s) to form a condensed ring, and/or can optionally be substituted by G,
$R^{116}$ and $R^{117}$ are as defined below,
$R^{121'}$ is $C_6$-$C_{18}$aryl; or $C_2$-$C_{20}$heteroaryl; which can optionally be substituted by $C_1$-$C_{18}$alkyl, $C_1$-$C_{18}$perfluoroalkyl, or $C_1$-$C_{18}$alkoxy; $C_1$-$C_{18}$alkyl; or $C_1$-$C_{18}$alkyl which is interrupted by —O—;
$R^{120}$, $R^{123}$, $R^{124}$ and $R^{125}$ independently of each other H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, which can optionally be substituted by G, $C_2$-$C_{20}$heteroaryl, which can optionally be substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl,
$R^{127}$ and $R^{128}$ are independently of each other H, CN, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, which can optionally be substituted by G, $C_2$-$C_{20}$heteroaryl, which can optionally be substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, $L^1$ is a single bond, —$(CR^{47}=CR^{48})_{m2}$—, —$(Ar^3)_{m3}$—, —$[Ar^3(Y^1)_{m1}]_{m4}$—, —$[(Y^1)_{m1}Ar^3]_{m4}$—, or —$[Ar^3(Y^2)_{m1}Ar^4]_{m4}$—, wherein $Y^1$ is —$(CR^{47}=CR^{48})$—, $Y^2$ is $NR^{49}$, O, S, C=O, C(=O)O, wherein $R^{49}$ is H; $C_6$-$C_{18}$aryl which can optionally be substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{47}$ and $R^{48}$ are independently of each other hydrogen, fluorine, $C_1$-$C_{20}$alkyl, or $C_6$-$C_{24}$aryl, which can optionally be substituted by G, m1 is an integer of 1 to 10, m2 is an integer of 1 to 10, m3 is an integer of 1 to 5, m4 is an integer of 1 to 5, $Ar^3$ and $Ar^4$ are independently of each other arylen, or heteroarylen, which can optionally be substituted.

$X^4$, $X^5$ and $X^6$ are independently of each other N, or CH, with the proviso that at least one, preferably at least two of the substituents $X^4$, $X^5$ and $X^6$ are N, and $Ar^1$ and $Ar^2$ are independently of each other $C_6$-$C_{24}$aryl, which can optionally be substituted by G, or $C_2$-$C_{20}$heteroaryl, which can optionally be substituted by G, wherein D, E and G are as defined below.

$R^{127}$ and $R^{128}$ are preferably independently of each other H, CN, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, which can optionally be substituted by G, $C_2$-$C_{20}$heteroaryl, which can optionally be substituted by G, or $C_7$-$C_{25}$aralkyl.

$R^{120}$, $R^{122}$, $R^{123}$, $R^{124}$ and $R^{125}$ are preferably independently of each other H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, which can optionally be substituted by G, or $C_2$-$C_{20}$heteroaryl, which can optionally be substituted by G, Specific examples of the aromatic heterocyclic ring formed by $Q^1$, or $Q^2$ include pyridine, pyrazine, pyrimidine, pyridazine and triazine. Preferred are pyridine, pyrazine, pyrimidine and pyridazine, with pyridine and pyrazine being more preferred, and pyridine being still more preferred. The (6-membered) aromatic heterocyclic ring formed by $Q^1$, or $Q^2$ may be condensed with other ring(s) to form a condensed ring, or may have a substituent G.

More specific examples of the groups $Z^1$ and $Z^2$ are the following groups:

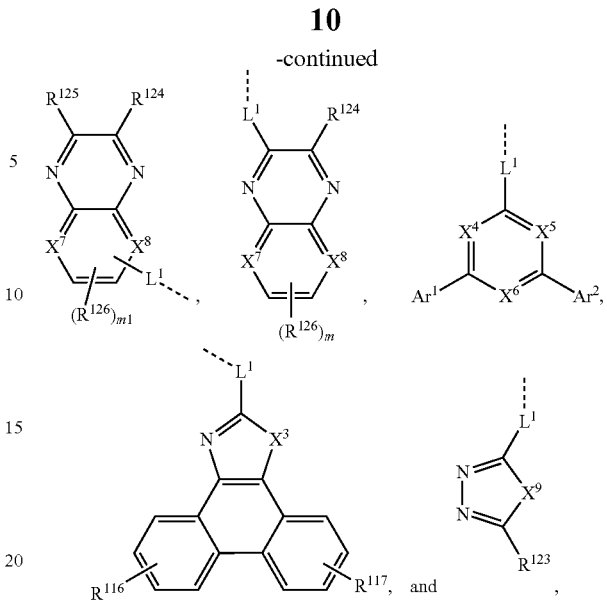

wherein m is 0, or an integer 1 to 3,
m1 is 0, 1, or 2,
$R^{116}$ and $R^{117}$ are as defined below,
$R^{123}$, $Ar^1$ and $Ar^2$ are independently of each other phenyl or 1- or 2-naphthyl which can be substituted one to three times with $C_1$-$C_{18}$alkyl, $C_1$-$C_{18}$alkyl, which can optionally be interrupted by O; or $C_1$-$C_{18}$alkoxy, which can optionally be interrupted by O, $R^{126}$ can be the same or different at each occurrence and is F, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{125}$, —C(=O)—$R^{127'}$, or —C(=O)$NR^{122}R^{122'}$, or substituents $R^{126}$, which are adjacent to each other, can form a ring, $R^{122}$ and $R^{122'}$ are independently of each other H; $C_6$-$C_{18}$aryl; or $C_2$-$C_{20}$heteroaryl; which can optionally be substituted by $C_1$-$C_{18}$alkyl, $C_1$-$C_{18}$perfluoroalkyl, or $C_1$-$C_{18}$alkoxy; $C_1$-$C_{18}$alkyl; or $C_1$-$C_{18}$alkyl which is interrupted by —O—;

$R^{127}$ and $R^{127'}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $X^7$ and $X^8$ are independently of each other N, or $CR^{127''}$, wherein $R^{127''}$ has the meaning of $R^{126}$, and $R^{120}$, $R^{124}$, $R^{125}$, $X^3$, $X^4$, $X^5$, $X^6$, $X^9$ and $L^1$ are as defined above.

Among the above groups $Z^1$ and $Z^2$ the following groups are even more preferred:

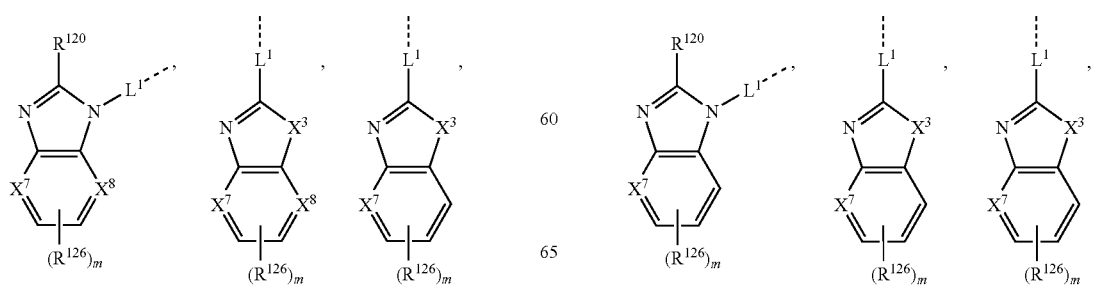

wherein the following groups are most preferred:

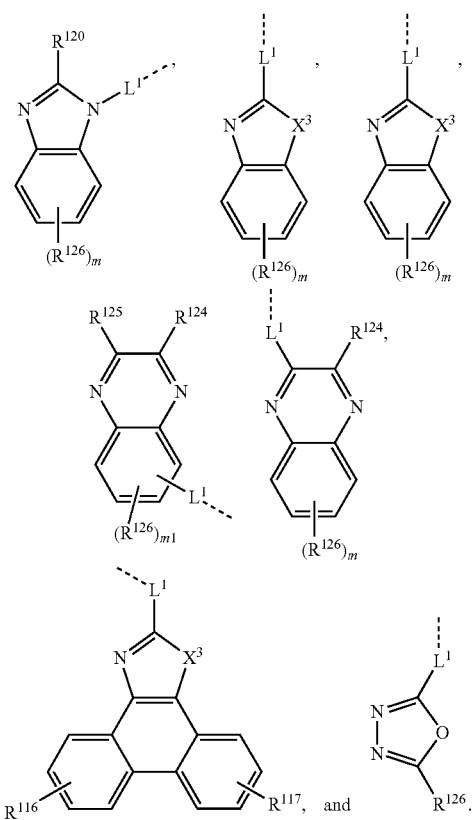

L¹ (or L) is preferably a single bond, or a group

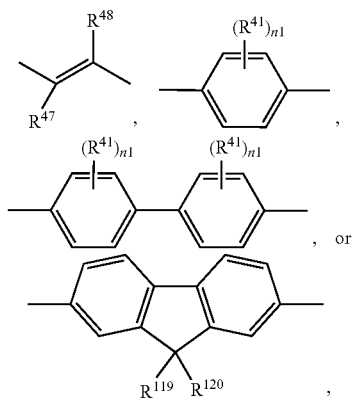

wherein R⁴¹ can be the same or different at each occurrence and is F, CN, N(R⁴⁵)₂, a C₁-C₂₅alkyl group, a C₄-C₁₈cycloalkyl group, a C₁-C₂₅alkoxy group, in which one or more carbon atoms which are not in neighbourhood to each other could be replaced by —NR⁴⁵—, —O—, —S—, —C(=O)—O—, or —O—C(=O)—O—, and/or wherein one or more hydrogen atoms can be replaced by F, a C₆-C₂₄aryl group, or a C₆-C₂₄aryloxy group, wherein one or more carbon atoms can be replaced by O, S, or N, and/or which can be substituted by one or more non-aromatic groups R⁴¹, or two or more groups R⁴¹ form a ring system;

R⁴⁵ is a C₁-C₂₅alkyl group, a C₄-C₁₈cycloalkyl group, in which one or more carbon atoms which are not in neighbourhood to each other could be replaced by —NR⁴⁵″—, —O—, —S—, —C(=O)—O—, or, —O—C(=O)—O—, and/or wherein one or more hydrogen atoms can be replaced by F, a C₆-C₂₄aryl group, or a C₆-C₂₄aryloxy group, wherein one or more carbon atoms can be replaced by O, S, or N, and/or which can be substituted by one or more non-aromatic groups R⁴¹, and R⁴⁵″ is H, a C₁-C₂₅alkyl group, or a C₄-C₁₈cycloalkyl group, n1 is 0, or an integer 1 to 3, and R⁴⁷, R⁴⁸, R¹¹⁹ and R¹²⁰ are as defined above. Most preferred for L¹ are a single bond, or a group

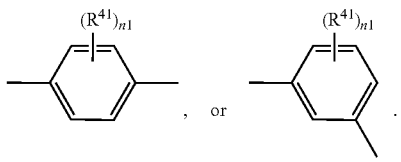

In a particularly preferred embodiment of the present invention Z¹ and Z² are independently of each other a group

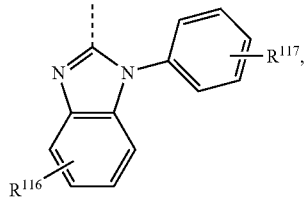

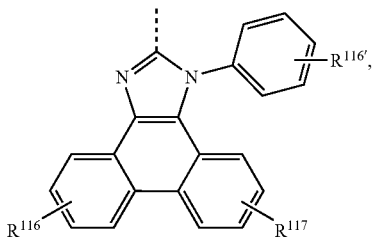

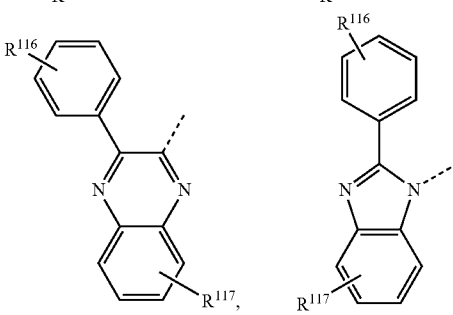

-continued
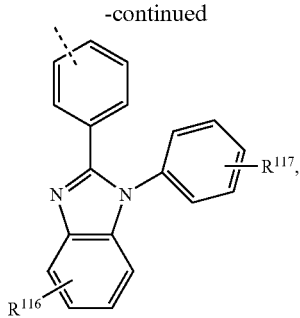
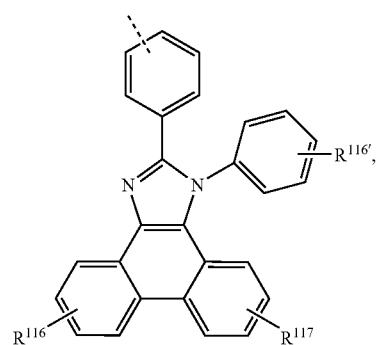
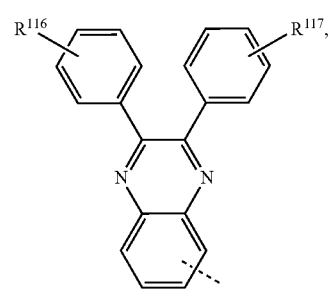
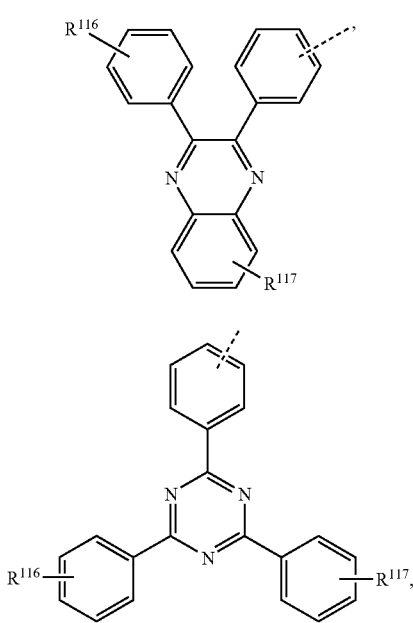
-continued
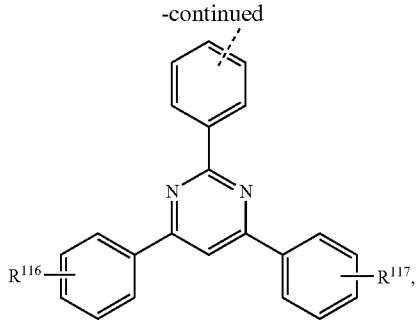
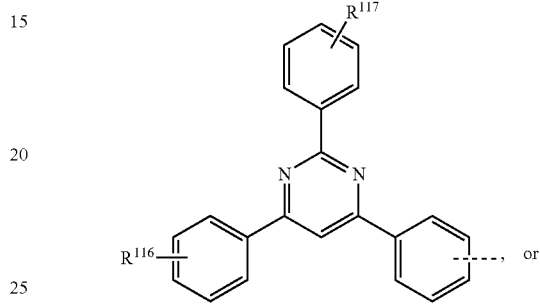
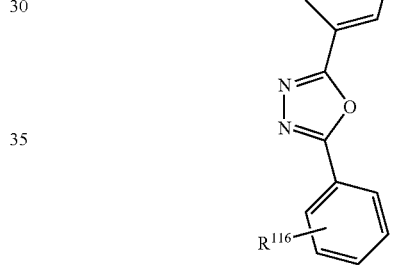
In another preferred embodiment of the present invention $Z^1$ and $Z^2$ are independently of each other a group
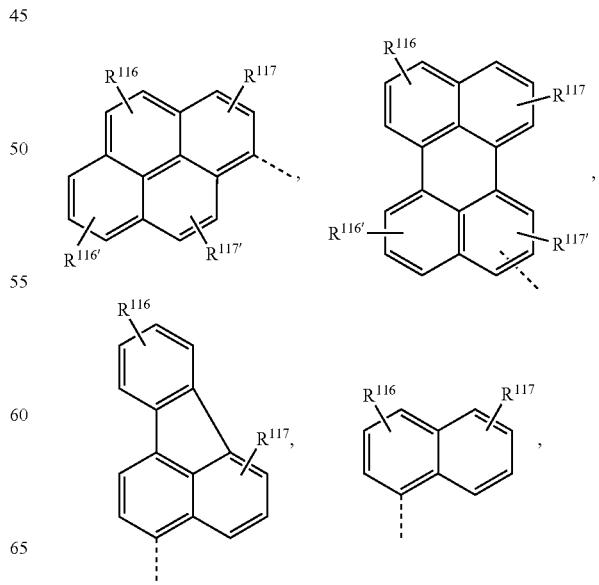

-continued

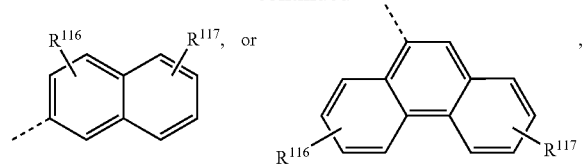

wherein $R^{116}$, $R^{116'}$, $R^{117}$ and $R^{117'}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{127}$, —C(=O)O$R^{127}$, or —C(=O)N$R^{127}R^{126}$, or substituents $R^{116}$, $R^{117}$ and $R^{117'}$, which are adjacent to each other, can form a ring, $R^{126}$ and $R^{127}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, D, E and G are as defined above.

Preferably, $R^{116}$, $R^{116'}$, $R^{117}$ and $R^{117'}$ are independently of each other H, F, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, D is —O—; —N$R^{25}$—; and E is —O$R^{29}$; —N$R^{25}R^{26}$; —CN; or F;

G is E, $C_1$-$C_{18}$alkyl, $C_1$-$C_{18}$alkyl which is interrupted by O, $C_1$-$C_{18}$alkoxy, or $C_1$-$C_{18}$alkoxy which interrupted by O, wherein $R^{23}$, $R^{24}$, $R^{25}$ and $R^{26}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or $R^{25}$ and $R^{26}$ together form a five or six membered ring, and $R^{29}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—.

A is a 5-, 6-, or 7-membered heteroaromatic ring, containing one heteroatom selected from nitrogen, oxygen and sulphur, which can be substituted and/or can be part of a fused aromatic or heteroaromatic ring system. Non-limiting examples of A are:

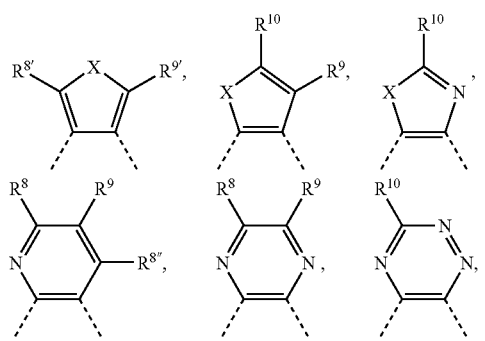

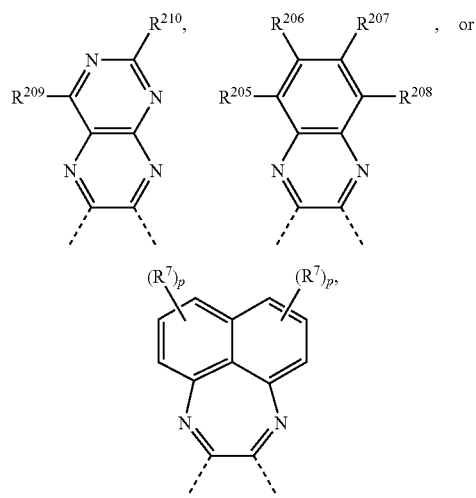

wherein $R^7$ has the meaning of $R^8$, $R^{8''}$ has the meaning of $R^8$, X is O, S, N—$R^{17}$, wherein $R^{205}$, $R^{206}$, $R^{207}$, $R^{208}$, $R^{209}$, $R^{210}$, $R^8$, $R^9$, $R^{8'}$, $R^{9'}$, $R^{10}$ and $R^{17}$ are as defined below, p is 0, 1, 2, or 3 and the dotted line - - - indicates the bonding to the biphenyl unit.

Preferably, the compound of formula I is a compound according of formula:

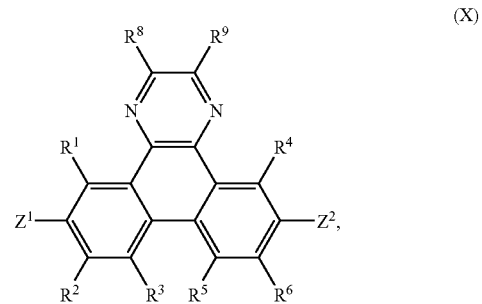

(X)

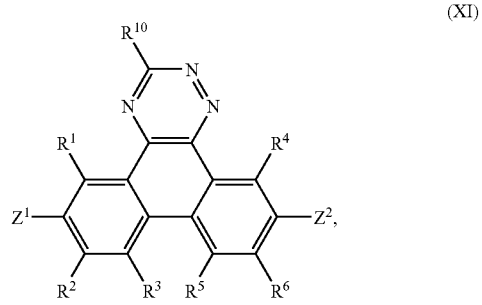

(XI)

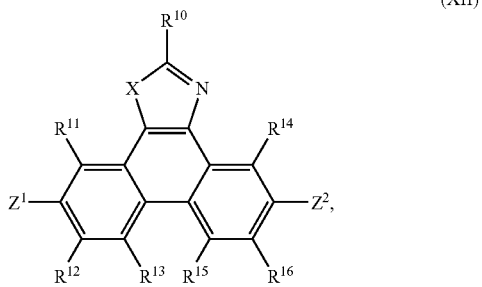

(XII)

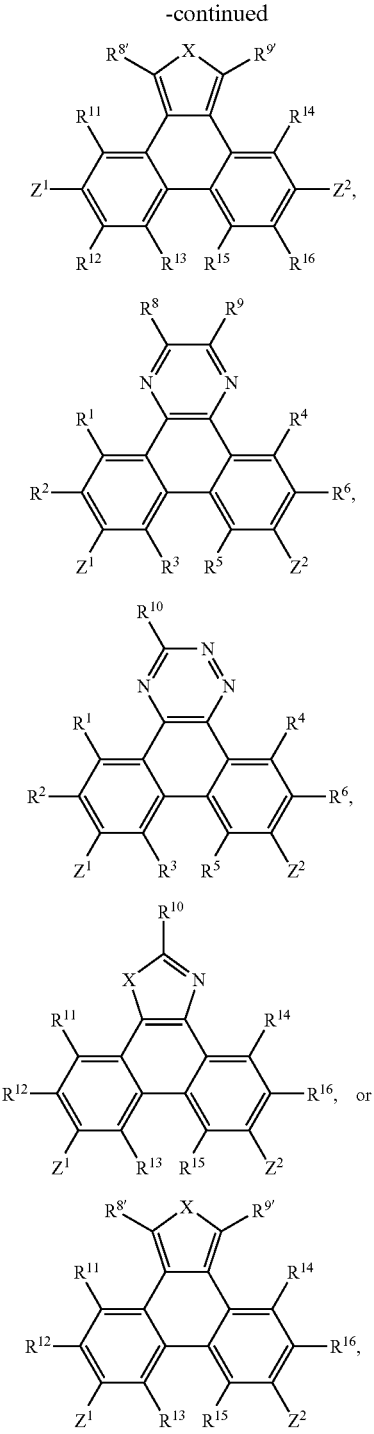

$C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$, $R^8$ and $R^9$ are independently of each other H, CN, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$, or $R^8$ and $R^9$ together form a group wherein $R^{206'}$, $R^{208'}$, $R^{205}$, $R^{206}$, $R^{207}$, $R^{208}$, $R^{209}$ and $R^{210}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_7$-$C_{25}$aralkyl, CN, or —CO—$R^{28}$, $R^{10}$ is H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —CO—$R^{28}$, $R^{8'}$ and $R^{9'}$ are independently of each other H, CN, —COO$R^{27}$; —CONR$^{25}$R$^{26}$, $C_1$-$C_{18}$alkyl, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$;

$R^{11}$ and $R^{14}$ are independently of each other hydrogen, F, $C_1$-$C_{18}$alkyl, $C_1$-$C_{18}$alkyl which is substituted by E and/or interrupted by D, $C_1$-$C_{18}$perfluoroalkyl, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, CN, or —CO—$R^{28}$, $R^{12}$, $R^{13}$, $R^{15}$ and $R^{16}$ are independently of each other H, halogen, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN or —CO—$R^{28}$, X is O, S, or NR$^{17}$, wherein R$^{17}$ is $C_6$-$C_{18}$aryl; $C_2$-$C_{20}$heteroaryl; $C_6$-$C_{18}$aryl, or $C_2$-$C_{20}$heteroaryl, which are substituted by $C_1$-$C_{18}$alkyl, $C_1$-$C_{18}$perfluoroalkyl, —N($C_6$-$C_{18}$aryl)$_2$, or $C_1$-$C_{18}$alkoxy; $C_1$-$C_{18}$alkyl; or $C_1$-$C_{18}$alkyl which is interrupted by —O—;

or two substituents $R^1$ and $R^2$, $R^4$ and $R^6$, $R^{11}$ and $R^{12}$, and/or $R^{14}$ and $R^{16}$, $R^2$ and $R^3$, $R^5$ and $R^6$, $R^{12}$ and $R^{13}$, and/or $R^{15}$ and $R^{16}$, which are adjacent to each other, together form a group

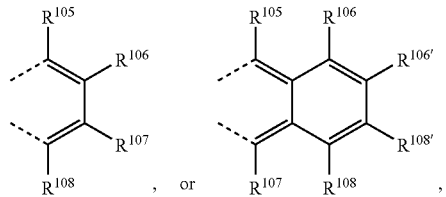

or two substituents $R^{15}$ and $R^{13}$, and/or $R^5$ and $R^3$, which are adjacent to each other, together form a group

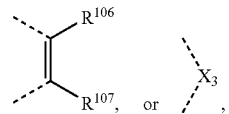

wherein $X^3$ is O, S, C($R^{119}$)($R^{120}$), or $NR^{17}$, wherein $R^{17}$ is as defined above, $R^{105}$, $R^{106}$, $R^{107}$, $R^{108}$, $R^{106'}$ and $R^{108'}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $R^{119}$ and $R^{126}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{119}$ and $R^{120}$ together form a group of formula =$CR^{121}R^{122}$, wherein $R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—$R^{127}$, and $R^{127}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, D is —CO—; —COO—; —S—; —SO—; —SO$_2$—; —O—; —$NR^{25}$—; —$SiR^{30}R^{31}$—; —$POR^{32}$—; —$CR^{23}$=$CR^{24}$—; or —C≡C—; and E is $OR^{29}$; —$SR^{29}$; —$NR^{25}R^{26}$; —$COR^{28}$; —$COOR^{27}$; —$CONR^{25}R^{26}$; —CN; or halogen; G is E, $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, wherein $R^{23}$, $R^{24}$, $R^{25}$ and $R^{26}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or $R^{25}$ and $R^{26}$ together form a five or six membered ring, $R^{27}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{28}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{29}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{30}$ and $R^{31}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{32}$ is $C_1$-$C_{18}$alkyl, $C_6$-$C_{18}$aryl, or $C_6$-$C_{18}$aryl, which is substituted by $C_1$-$C_{18}$alkyl, and $Z^1$ and $Z^2$ are as defined above.

Preferably, $R^{116}$ and $R^{117}$ are independently of each other H, $C_1$-$C_{12}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, or n-heptyl, $C_1$-$C_{12}$alkyl which is substituted by E and/or interrupted by D, such as —$CH_2OCH_3$, —$CH_2OCH_2CH_3$, —$CH_2OCH_2CH_2OCH_3$, or —$CH_2OCH_2CH_2OCH_2CH_3$, $C_6$-$C_{14}$aryl, such as phenyl, naphthyl, or biphenylyl, $C_5$-$C_{12}$cycloalkyl, such as cyclohexyl, $C_6$-$C_{14}$aryl which is substituted by G, such as —$C_6H_4OCH_3$, —$C_6H_4OCH_2CH_3$, —$C_6H_3(OCH_3)_2$, or —$C_6H_3(OCH_2CH_3)_2$, —$C_6H_4CH_3$, —$C_6H_3(CH_3)_2$, —$C_6H_2(CH_3)_3$, or —$C_6H_4tBu$.

X is O, S, or $NR^{17}$. In case of compounds of formula XII and XVIII X is preferably O, or $NR^{17}$. In case of compounds of formula XIII and XIX X is preferably S, or $NR^{17}$.

$R^{17}$ is preferably $C_1$-$C_{12}$alkyl, such as methyl, ethyl, n-propyl, iso-propyl, n-butyl, isobutyl, sec-butyl, t-butyl, 2-methylbutyl, n-pentyl, isopentyl, n-hexyl, 2-ethylhexyl, n-heptyl, or $C_6$-$C_{14}$aryl, such as phenyl, naphthyl, or biphenylyl.

Preferably, $R^{119}$ and $R^{120}$ are independently of each other $C_1$-$C_{12}$alkyl, such as methyl, ethyl, n-propyl, iso-propyl, n-butyl, sec-butyl, hexyl, octyl, or 2-ethyl-hexyl, $C_1$-$C_{12}$alkyl which is substituted by E and/or interrupted by D, such as —$CH_2(OCH_2CH_2)_wOCH_3$, w=1, 2, 3, or 4, $C_6$-$C_{14}$aryl, such as phenyl, naphthyl, or biphenylyl, $C_6$-$C_{14}$aryl which is substituted by G, such as —$C_6H_4OCH_3$, —$C_6H_4OCH_2CH_3$, —$C_6H_3(OCH_3)_2$, —$C_6H_3(OCH_2CH_3)_2$, —$C_6H_4CH_3$, —$C_6H_3(CH_3)_2$, —$C_6H_2(CH_3)_3$, or —$C_6H_4tBu$, or $R^{119}$ and $R^{120}$ together form a 4 to 8 membered ring, especially a 5 or 6 membered ring, such as cyclohexyl, or cyclopentyl, which can optionally be substituted by $C_1$-$C_8$alkyl.

D is preferably —CO—, —COO—, —S—, —SO—, —$SO_2$—, —O—, —$NR^{25}$—, wherein $R^{25}$ is $C_1$-$C_{12}$alkyl, such as methyl, ethyl, n-propyl, iso-propyl, n-butyl, isobutyl, or sec-butyl, or $C_6$-$C_{14}$aryl, such as phenyl, naphthyl, or biphenylyl.

E is preferably —$OR^{29}$; —$SR^{29}$; —$NR^{25}R^{25}$; —$COR^{28}$; —$COOR^{27}$; —$CONR^{25}R^{25}$; or —CN; wherein $R^{25}$, $R^{27}$, $R^{28}$ and $R^{29}$ are independently of each other $C_1$-$C_{12}$alkyl, such as methyl, ethyl, n-propyl, iso-propyl, n-butyl, isobutyl, sec-butyl, hexyl, octyl, or 2-ethyl-hexyl, or $C_6$-$C_{14}$ aryl, such as phenyl, naphthyl, or biphenylyl, which may optionally be substituted.

G has the same preferences as E, or is $C_1$-$C_{18}$alkyl, especially $C_1$-$C_{12}$alkyl, such as methyl, ethyl, n-propyl, iso-propyl, n-butyl, isobutyl, sec-butyl, hexyl, octyl, or 2-ethyl-hexyl.

Compounds of the formula X, XI, XII, XVI, XVII or XVIII are preferred, compounds of the formula X, XII, XVI and XVIII are even more preferred, wherein $R^1$ and $R^4$ are hydrogen, $R^2$, $R^3$, $R^5$ and $R^6$ are independently of each other H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, $C_7$-$C_{25}$aralkyl, or a group —$X^2$—$R^{18}$, $R^8$ and $R^9$ are independently of each other H, CN, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, or a group —$X^2$—$R^{18}$; or two substituents $R^2$ and $R^3$ and/or $R^5$ and $R^6$, which are adjacent to each other, together form a group

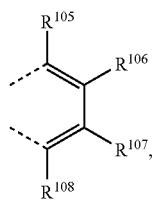

or two substituents $R^5$ and $R^3$, which are adjacent to each other, together form a group

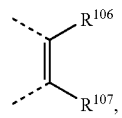

wherein $R^{105}$, $R^{106}$, $R^{107}$ and —$R^{108}$ are independently of each other H, or $C_1$-$C_8$alkyl, or $R^8$ and $R^9$ together form a group

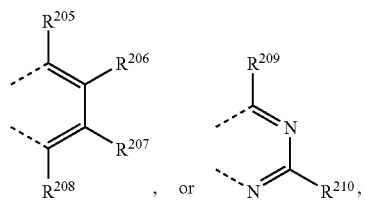

wherein $R^{205}$, $R^{206}$, $R^{207}$, $R^{208}$, $R^{209}$ and $R^{210}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $C_1$-$C_{18}$perfluoroalkyl, $R^{10}$ is H, $C_6$-$C_{18}$aryl, which can be substituted by G, $C_2$-$C_{18}$heteroaryl, which can be substituted by G, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is substituted by E and/or interrupted by D, or a group —$X^2$—$R^{18}$, wherein $X^2$ is a spacer, such as $C_6$-$C_{12}$aryl, or $C_6$-$C_{12}$heteroaryl, especially phenyl, or naphthyl, which can be substituted one more, especially one to two times with $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, and $R^{18}$ is H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, or —$NR^{25}R^{26}$;

D is —CO—; —COO—; —S—; —SO—; —$SO_2$—; —O—; —$NR^{25}$—; —$CR^{23}$=$CR^{24}$—; or —C≡C—; wherein $R^{23}$, $R^{24}$, $R^{25}$ and $R^{26}$ are independently of each other H; $C_6$-$C_{18}$aryl; $C_6$-$C_{18}$aryl which is substituted by $C_1$-$C_8$alkyl, or $C_1$-$C_8$alkoxy; $C_1$-$C_8$alkyl; or $C_1$-$C_8$alkyl which is interrupted by —O—, or $R^{25}$ and $R^{26}$ together form a five or six membered ring, and $Z^1$ and $Z^2$ are as defined above.

In a further preferred embodiment the present invention relates to compounds of formula

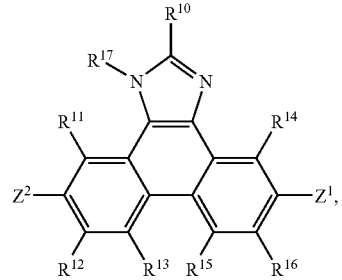
(XIIa)

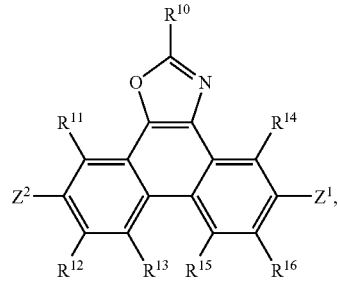
(XIIb)

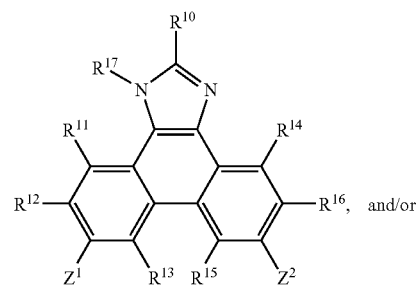
(XVIIIa)

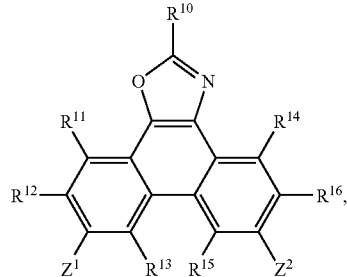
(XVIIIb)

wherein $R^{10}$ is H, $C_6$-$C_{18}$aryl, which can be substituted by G, $C_2$-$C_{18}$heteroaryl, which can be substituted by G, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is substituted by E and/or interrupted by D, or a group —$X^2$—$R^{18}$, wherein $X^2$ is a spacer, such as $C_6$-$C_{12}$aryl, or $C_6$-$C_{12}$heteroaryl, especially phenyl, or naphthyl, which can be substituted one more, especially one to two times with $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, and $R^{18}$ is H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, or —$NR^{25}R^{26}$;

$R^{11}$ and $R^{14}$ are hydrogen, $R^{12}$, $R^{13}$, $R^{15}$ and $R^{16}$ are hydrogen, $R^{17}$ is $C_6$-$C_{18}$aryl; $C_6$-$C_{18}$aryl which is substituted by $C_1$-$C_{18}$alkyl, $C_1$-$C_{18}$perfluoroalkyl, or $C_1$-$C_{18}$alkoxy; $C_1$-$C_{18}$alkyl; —N($C_6$-$C_{18}$aryl)$_2$, or $C_1$-$C_{18}$alkyl which is interrupted by —O—; or two substituents $R^5$ and $R^3$, $R^{12}$ and $R^{13}$, and/or $R^{15}$ and $R^{16}$, which are adjacent to each other, together form a group

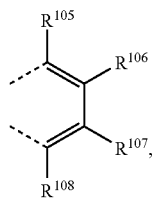

or two substituents $R^{15}$ and $R^{13}$, which are adjacent to each other, together form a group

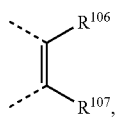

wherein $R^{105}$, $R^{106}$, $R^{107}$ and $R^{108}$ are independently of each other H, or $C_1$-$C_8$alkyl, D is —S—; —O—; or —$NR^{25}$—;

E is —$OR^{29}$; —$SR^{29}$; —$NR^{25}R^{26}$; —CN; or F; G is E, $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, wherein $R^{25}$ and $R^{26}$ are independently of each other H; $C_6$-$C_{18}$aryl; $C_6$-$C_{18}$aryl which is substituted by $C_1$-$C_8$alkyl, or $C_1$-$C_8$alkoxy; $C_1$-$C_8$alkyl; or $C_1$-$C_8$alkyl which is interrupted by —O—, or $R^{25}$ and $R^{26}$ together form a five or six membered ring, in particular

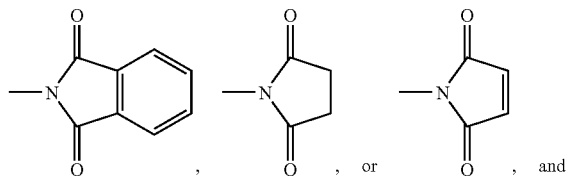

$R^{29}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, and $Z^1$ and $Z^2$ are as defined above.

In a preferred embodiment the present invention is directed to compounds of formula XIIa, especially XIIa, XVIIIa, especially XVIIIa, wherein $R^{10}$ is a group of formula

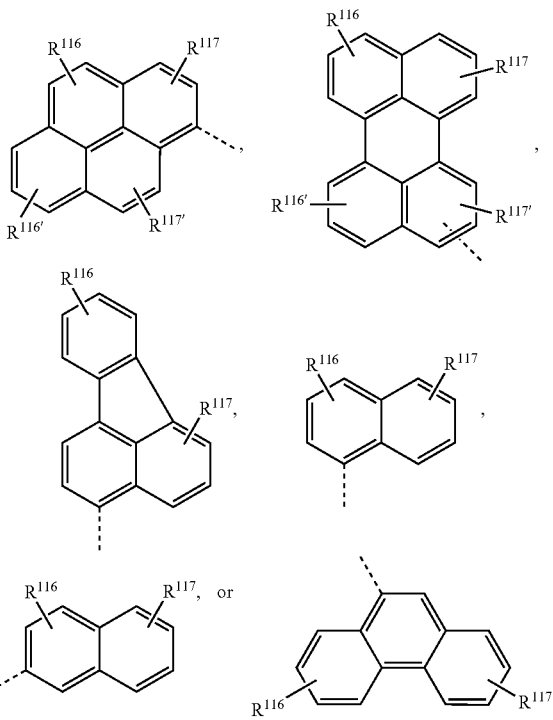

wherein $R^{116}$, $R^{116'}$, $R^{117}$ and $R^{117'}$ are as defined above.

In another preferred embodiment the present invention is directed to compounds of formula I, wherein $Z^1$ and $Z^2$ are independently of each other a group of formula

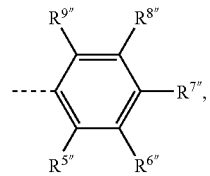

wherein $R^{5''}$ is hydrogen, or has the meaning of $R^6$, $R^{6''}$, $R^{7''}$, $R^{8''}$ and $R^{9''}$ are independently of each other $C_6$-$C_{18}$aryl; which may optionally be substituted by G; or $C_2$-$C_{20}$heteroaryl, which may optionally be substituted by G. Preferably, $R^{5''}$, $R^{6''}$, $R^{7''}$, $R^{8''}$ and $R^{9''}$ are independently of each other a group of formula

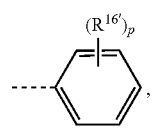

wherein p1 is 0, or an integer 1 to 4, p is 0, or an integer 1 to 5, $R^{16'}$ may be the same or different in each occurrence and is $C_1$-$C_{18}$alkyl, $C_1$-$C_{18}$alkyl which is interrupted by O, $C_1$-$C_{18}$perfluoroalkyl, $C_6$-$C_{18}$aryl, which may be substituted by $C_1$-$C_{18}$alkyl which may be interrupted by —O—.

In a preferred embodiment the present invention is directed to compounds of formula

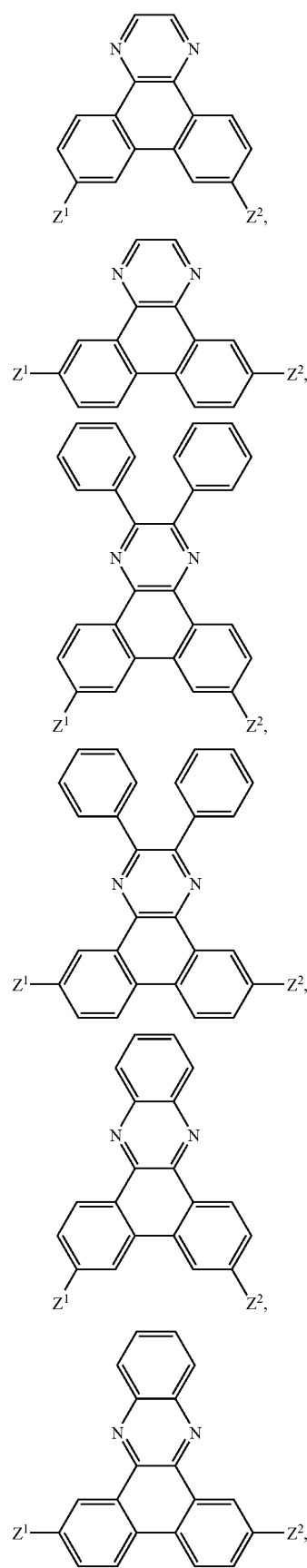
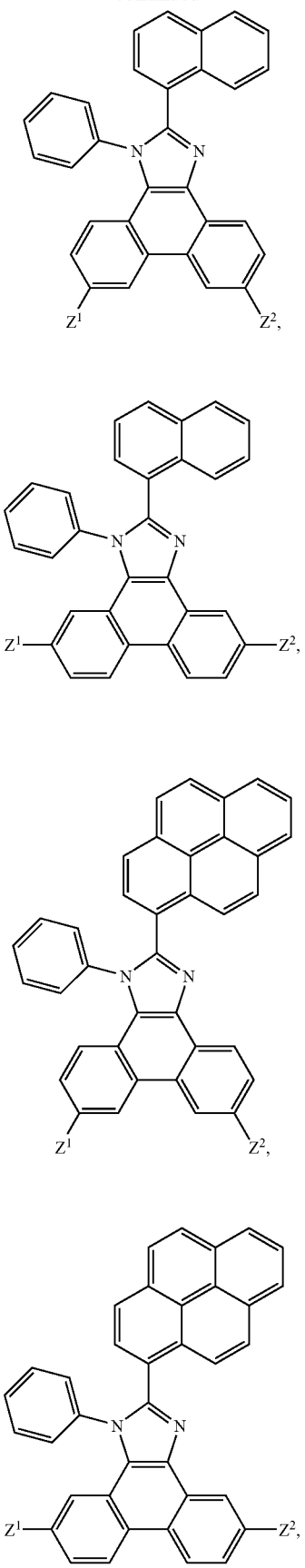

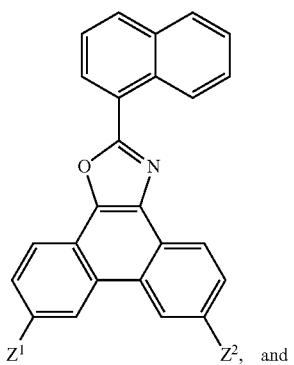
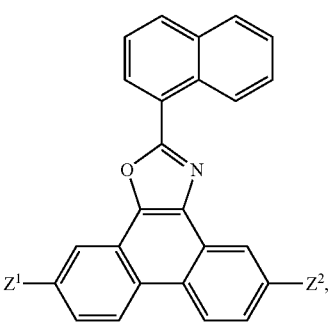
wherein $Z^1$ and $Z^2$ are independently of each other
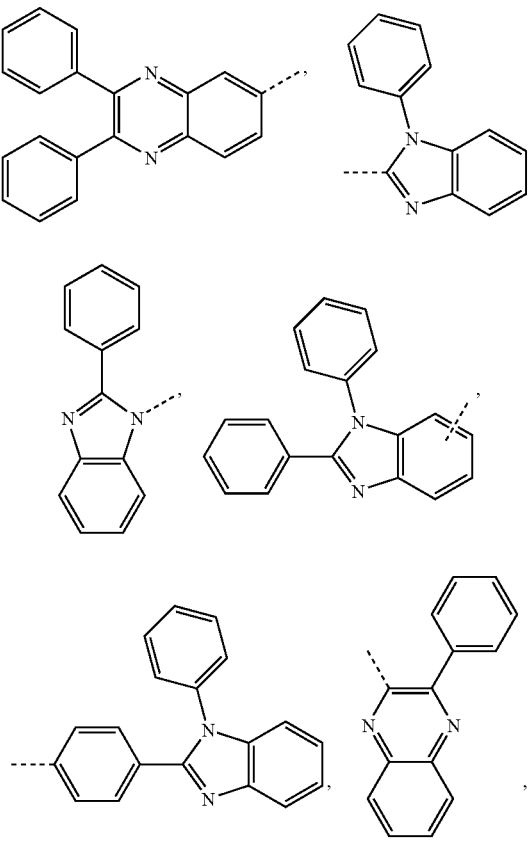
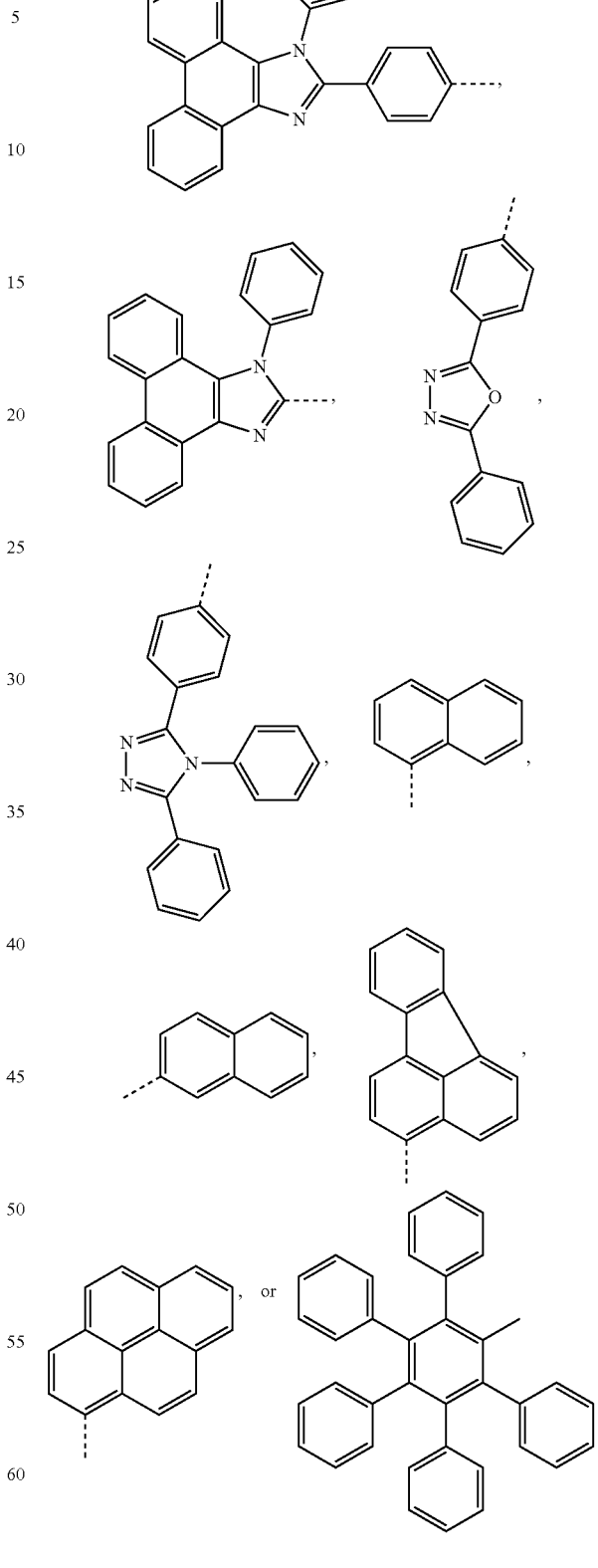
$Z^1$ and $Z^2$ can be different, but are preferably the same.
Examples of particularly preferred compounds are compounds A1 to A16, B1 to B16, C1 to C16, D1 to D16, E1 to E16, F1 to F16, G1 to G16, H1 to H16, I1 to I16, J1 to J16, K1 to K16, and L1 to L16, which are shown in claim 7.

The compounds of formula I of the present invention can be prepared according to a process, which comprises reacting a derivative of formula

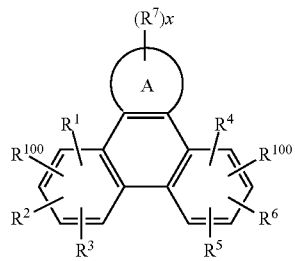

$R^{100}$ stands for halogen such as chloro or bromo, or iodo, preferably bromo, or iodo, most preferably bromo, with boronic acid derivative E-Ar, E having the meaning of

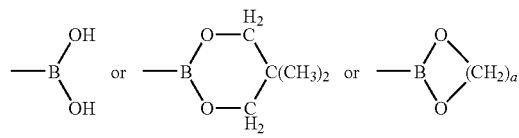

wherein a is 2 or 3, Ar has the meaning of $Z^1$, in the presence of an allylpalladium catalyst of the μ-halo (triisopropylphosphine)(η³-allyl)palladium(II) type (see for example WO99/47474).

Preferably, the reaction is carried out in the presence of an organic solvent, such as an aromatic hydrocarbon or a usual polar organic solvent, such as benzene, toluene, xylene, tetrahydrofurane, or dioxane, or mixtures thereof, most preferred toluene. Usually, the amount of the solvent is chosen in the range of from 1 to 10 l per mol of boronic acid derivative. Also preferred, the reaction is carried out under an inert atmosphere such as nitrogen, or argon.

Further, it is preferred to carry out the reaction in the presence of an aqueous base, such as an alkali metal hydroxide or carbonate such as NaOH, KOH, $Na_2CO_3$, $K_2CO_3$, $Cs_2CO_3$ and the like, preferably an aqueous $K_2CO_3$ solution is chosen. Usually, the molar ratio of the base to compound III is chosen in the range of from 0.5:1 to 50:1.

Generally, the reaction temperature is chosen in the range of from 40 to 180° C., preferably under reflux conditions.

Preferred, the reaction time is chosen in the range of from 1 to 80 hours, more preferably from 20 to 72 hours.

In a preferred embodiment a usual catalyst for coupling reactions or for polycondensation reactions is used, preferably Pd-based, which is described in WO2007/101820. The palladium compound is added in a ratio of from 1:10000 to 1:50, preferably from 1:5000 to 1:200, based on the number of bonds to be closed. Preference is given, for example, to the use of palladium(II) salts such as $PdAc_2$ or $Pd_2dba_3$ and to the addition of ligands selected from the group consisting of

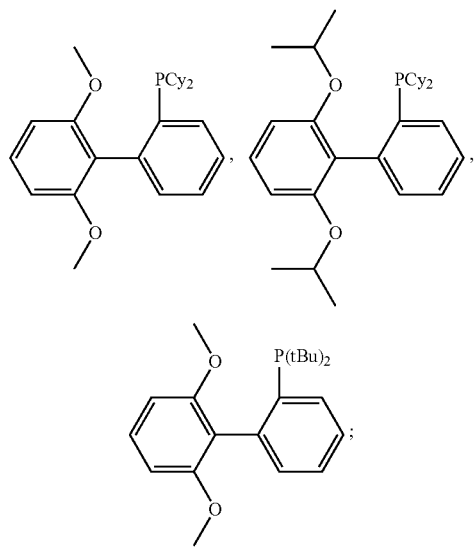

wherein

Cy = <img cyclohexyl>

The ligand is added in a ratio of from 1:1 to 1:10, based on Pd.

Also preferred, the catalyst is added as in solution or suspension. Preferably, an appropriate organic solvent such as the ones described above, preferably benzene, toluene, xylene, THF, dioxane, more preferably toluene, or mixtures thereof, is used. The amount of solvent usually is chosen in the range of from 1 to 10 l per mol of boronic acid derivative. The obtained inventive polymer can be isolated by well-known methods. Preferably, after cooling down the reaction mixture to room temperature, it is poured into acetone and the obtained precipitation is filtered off, washed and dried.

The preparation of the following compounds

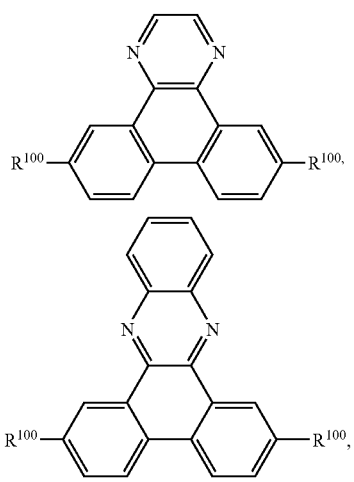

-continued

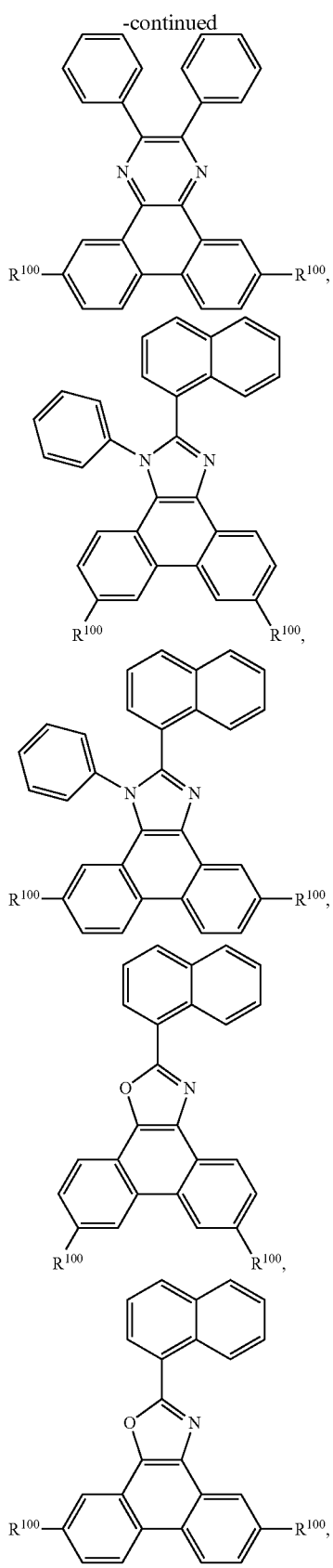

and analogs thereof, wherein $R^{100}$ is Br, or I, is described in WO2006/097419.

The following compounds

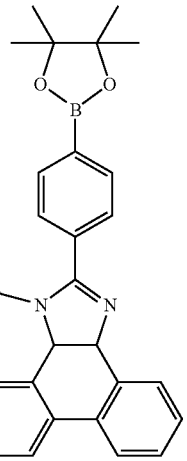

or analogs thereof, can be prepared according to WO2007/090773, or WO2006/097419.

The following compound

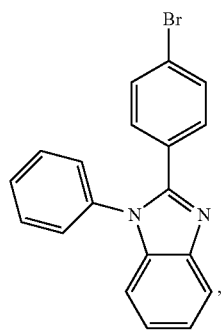 [SMILES: Brc1ccc(-c2nc3ccccc3n2-c2ccccc2)cc1]

or analogs thereof, can be prepared as described in Synthesis 2005, 47, or Synthesis 2003, 1683.

Compounds of formula I, wherein $Z^1$ and $Z^2$ are a group

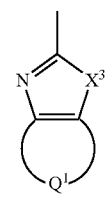

can be prepared according to, or in analogy to Synthesis 2005, 47 or Synthesis; 2003, 1683. An example of such a reaction is shown below:

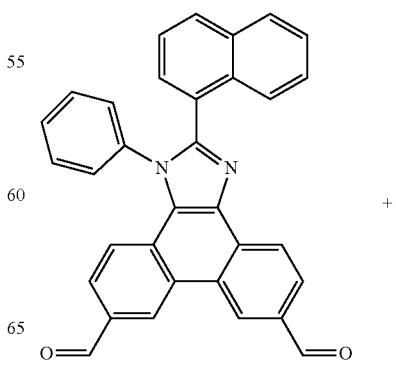

+

-continued

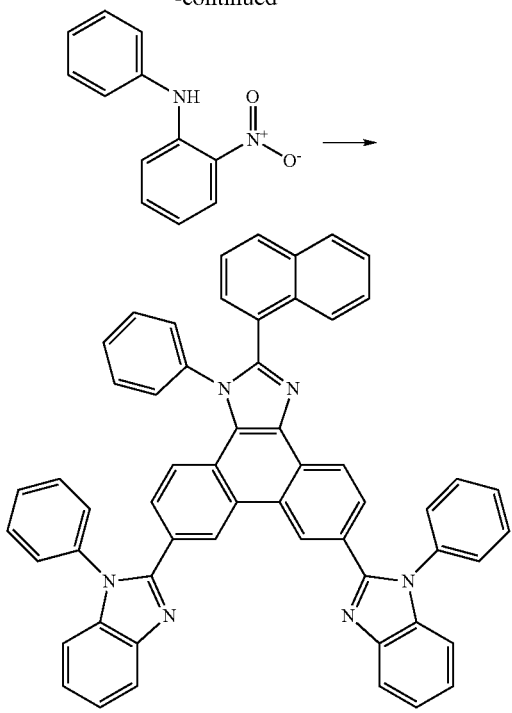

The synthesis of the starting compounds can be done according to, or in analogy to the procedure described in WO2007/090773.

Compounds of formula I, wherein $Z^1$ and $Z^2$ are a group can be prepared (Ulmann reaction) according, or in analogy to Inorg. Chem. 2006, 45, 147, or Inorg. Chem. 2005, 44, 1232.

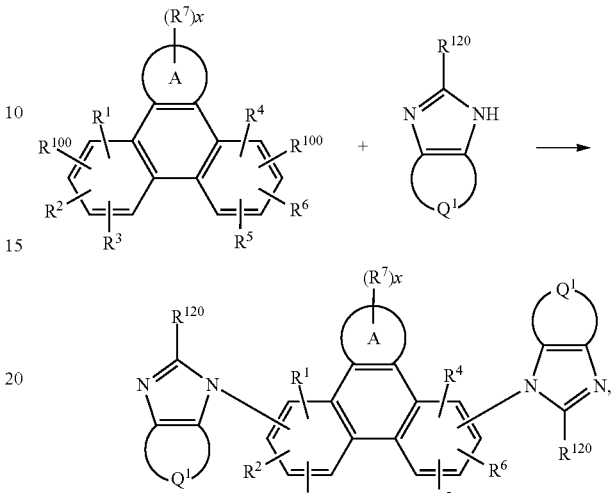

wherein $R^{100}$ stands for bromo, or iodo, preferably iodo.

Compounds of formula I, wherein $Z^1$ and $Z^2$ are a group

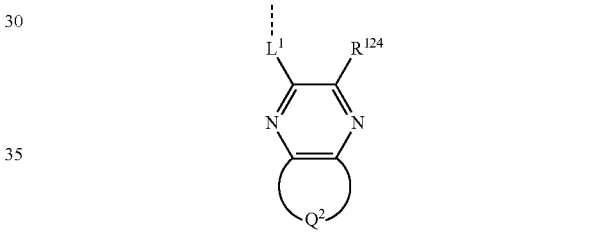

can be prepared according to, or in analogy to Adv. Funkt. Mater. 2006, 16, 1449. An example of such a reaction is shown below:

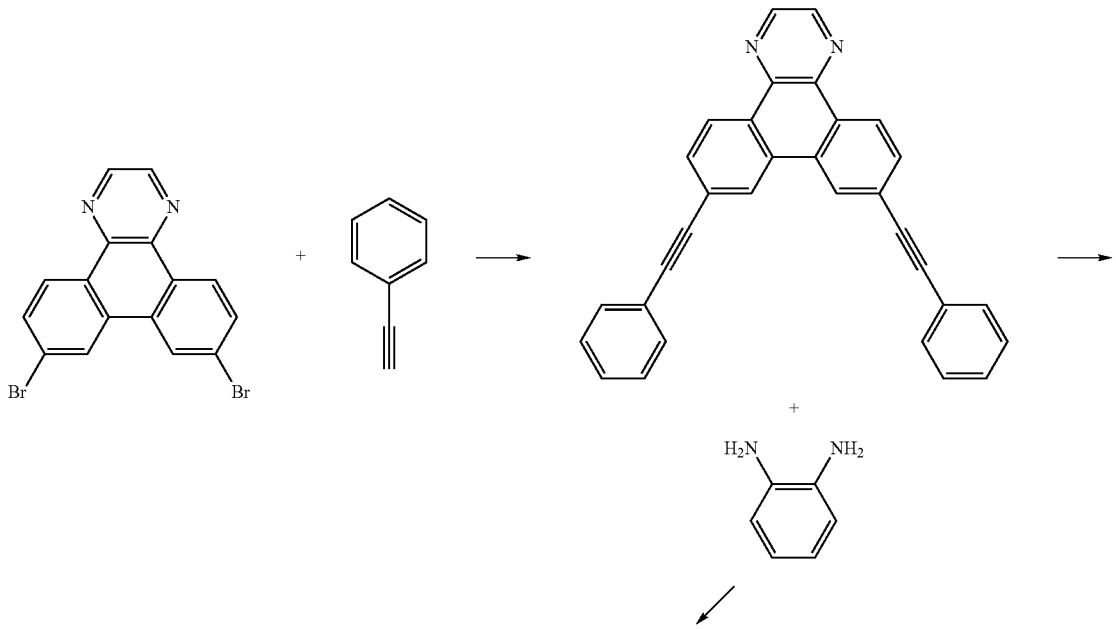

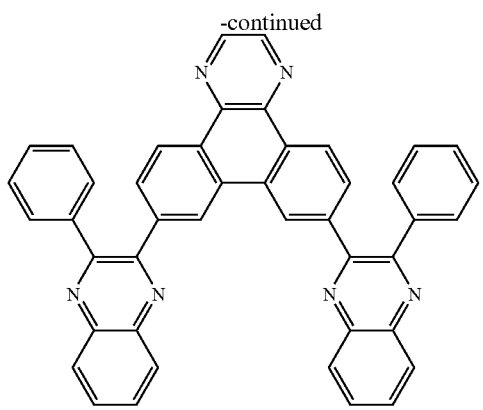

Halogen is fluorine, chlorine, bromine and iodine.

$C_1$-$C_{25}$alkyl is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

$C_2$-$C_{25}$alkenyl groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-24}$alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_1$-$C_{18}$perfluoroalkyl, especially $C_1$-$C_4$perfluoroalkyl, is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

The terms "haloalkyl, haloalkenyl and haloalkynyl" mean groups given by partially or wholly substituting the above-mentioned alkyl group, alkenyl group and alkynyl group with halogen, such as trifluoromethyl etc. The "aldehyde group, ketone group, ester group, carbamoyl group and amino group" include those substituted by an alkyl group, a cycloalkyl group, an aryl group, an aralkyl group or a heterocyclic group, wherein the alkyl group, the cycloalkyl group, the aryl group, the aralkyl group and the heterocyclic group may be unsubstituted or substituted. The term "silyl group" means a group of formula —$SiR^{62}R^{63}R^{64}$, wherein $R^{62}$, $R^{63}$ and $R^{64}$ are independently of each other a $C_1$-$C_8$alkyl group, in particular a $C_1$-$C_4$ alkyl group, a $C_6$-$C_{24}$aryl group or a $C_7$-$C_{12}$aralkyl group, such as a trimethylsilyl group. The term "siloxanyl group" means a group of formula —O—$SiR^{62}R^{63}R^{64}$, wherein $R^{62}$, $R^{63}$ and $R^{64}$ are as defined above, such as a trimethylsiloxanyl group.

The term "cycloalkyl group" is typically $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The term "cycloalkenyl group" means an unsaturated alicyclic hydrocarbon group containing one or more double bonds, such as cyclopentenyl, cyclopentadienyl, cyclohexenyl and the like, which may be unsubstituted or substituted. The cycloalkyl group, in particular a cyclohexyl group, can be condensed one or two times by phenyl which can be substituted one to three times with $C_1$-$C_4$-alkyl, halogen and cyano. Examples of such condensed cyclohexyl groups are:

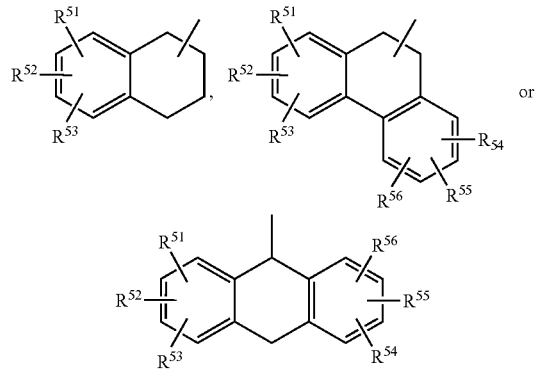

in particular

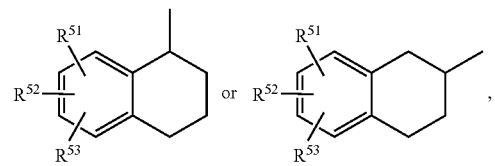

wherein $R^{51}$, $R^{52}$, $R^{53}$, $R^{54}$, $R^{55}$ and $R^{56}$ are independently of each other $C_1$-$C_8$-alkyl, $C_1$-$C_8$-alkoxy, halogen and cyano, in particular hydrogen.

Aryl is usually $C_6$-$C_{30}$aryl, preferably $C_6$-$C_{24}$aryl, which optionally can be substituted, such as, for example, phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, anthryl, tetracyl, pentacyl, hexacyl, or quaderphenylyl, which may be unsubstituted or substituted.

The term "aralkyl group" is typically $C_7$-$C_{24}$aralkyl, such as benzyl, 2-benzyl-2-propyl, β-phenyl-ethyl, α,α-dimethyl-benzyl, ω-phenyl-butyl, ω,ω-dimethyl-ω-phenyl-butyl, ω-phenyl-dodecyl, ω-phenyloctadecyl, ω-phenyl-eicosyl or ω-phenyl-docosyl, preferably $C_7$-$C_{18}$aralkyl such as benzyl, 2-benzyl-2-propyl, β-phenylethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted.

The term "aryl ether group" is typically a $C_{6-24}$aryloxy group, that is to say O—$C_{6-24}$aryl, such as, for example, phenoxy or 4-methoxyphenyl. The term "aryl thioether group" is typically a $C_{6-24}$arylthio group, that is to say S—$C_{6-24}$aryl, such as, for example, phenylthio or 4-methoxyphenylthio. The term "carbamoyl group" is typically a $C_{1-18}$carbamoyl radical, preferably $C_{1-8}$carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

The terms "aryl" and "alkyl" in alkylamino groups, dialkylamino groups, alkylarylamino groups, arylamino groups and diaryl groups are typically $C_1$-$C_{25}$alkyl and $C_6$-$C_{24}$aryl, respectively.

Alkylaryl refers to alkyl-substituted aryl radicals, especially $C_7$-$C_{12}$alkylaryl. Examples are tolyl, such as 3-methyl-, or 4-methylphenyl, or xylyl, such as 3,4-dimethylphenyl, or 3,5-dimethylphenyl.

Heteroaryl is typically $C_2$-$C_{26}$heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

Examples of a five or six membered ring formed by, for example, $R^{25}$ and $R^{26}$, respectively are heterocycloalkanes or heterocycloalkenes having from 3 to 5 carbon atoms which can have one additional hetero atom selected from nitrogen, oxygen and sulfur, for example

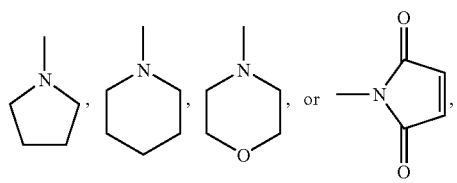

which can be part of a bicyclic system, for example

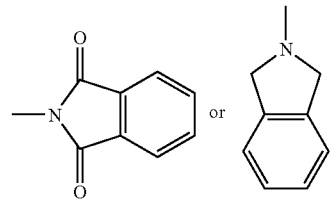

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group.

If a substituent, such as, for example $R^7$ occurs more than one time in a group, it can be different in each occurrence.

The wording "substituted by G" means that one, or more, especially one to three substituents G might be present.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl or alkylaryl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—CH($C_2H_5$)$C_4H_9$), $CH_2$—CH(O$R^{y''}$)—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y''}$ embraces the same definitions as $R^y$ or is H;
$C_1$-$C_8$alkylene-COO—$R^z$, e.g. $CH_2COOR_z$, $CH(CH_3)$COO$R^z$, $C(CH_3)_2COOR^z$, where $R^z$ is H, $C_1$-$C_{18}$alkyl, $(CH_2CH_2O)_{1-9}$—$R^x$, and $R^x$ embraces the definitions indicated above;
$CH_2CH_2$—O—CO—CH=$CH_2$; $CH_2CH(OH)CH_2$—O—CO—C($CH_3$)=$CH_2$.

Preferred arylene radicals are 1,4-phenylene, 2,5-tolylene, 1,4-naphthylene, 1,9 antracylene, 2,7-phenantrylene and 2,7-dihydrophenantrylene.

Preferred heteroarylene radicals are 2,5-pyrazinylene, 3,6-pyridazinylene, 2,5-pyridinylene, 2,5-pyrimidinylene, 1,3,4-thiadiazol-2,5-ylene, 1,3-thiazol-2,4-ylene, 1,3-thiazol-2,5-ylene, 2,4-thiophenylene, 2,5-thiophenylene, 1,3-oxazol-2,4-ylene, 1,3-oxazol-2,5-ylene and 1,3,4-oxadiazol-2,5-ylene, 2,5-indenylene and 2,6-indenylene.

The compounds of formula I can be used in organic light emitting diodes (OLEDs), especially as hosts for phosphorescent compounds. Accordingly, the present invention also relates to an electroluminescent device, comprising a compound of formula I. In a preferred embodiment the electroluminescent device comprising a cathode, an anode, and therebetween a light emitting layer containing a host material and a phosphorescent light-emitting material wherein the host material is a compound of formula I.

Suitably, the light-emitting layer of the OLED device comprises a host material and one or more guest materials for emitting light. At least one of the host materials is a compound comprising a compound of formula I. The light-emitting guest material(s) is usually present in an amount less than the amount of host materials and is typically present in an amount of up to 15 wt % of the host, more typically from 0.1 to 10 wt % of the host, and commonly from 2 to 8% of the host. For convenience, the phosphorescent complex guest material may be referred to herein as a phosphorescent material. The emissive layer may comprise a single material, that combines transport and emissive properties. Whether the emissive material is a dopant or a major constituent, emissive layer may comprise other materials, such as dopants that tune the emission of the emissive layer. The emissive layer may include a plurality of emissive materials capable of, in combination, emitting a desired spectrum of light.

Other Host Materials for Phosphorescent Materials

The host material useful in the invention may be used alone or in combination with other host materials. Other host materials should be selected so that the triplet exciton can be transferred efficiently from the host material to the phosphorescent material. Suitable host materials are described in WO00/70655; 01/39234; 01/93642; 02/074015; 02/15645, and US20020117662. Suitable hosts include certain aryl amines, triazoles, indoles and carbazole compounds. Examples of hosts are 4,4'-N,N'-dicarbazole-biphenyl (CBP), 2,2'-dimethyl-4,4'-N,N'-dicarbazole-biphenyl, m-(N,N'-dicarbazole)benzene, and poly(N-vinylcarbazole), including their derivatives.

Desirable host materials are capable of forming a continuous film. The light-emitting layer may contain more than one host material in order to improve the device's film morphology, electrical properties, light emission efficiency, and lifetime. The light emitting layer may contain a first host material that has good hole-transporting properties, and a second host material that has good electron-transporting properties.

Phosphorescent Materials

Phosphorescent materials may be used alone or, in certain cases, in combination with each other, either in the same or different layers. Examples of phosphorescent and related materials are described in WO00/57676, WO00/70655, WO01/41512, WO02/15645, US2003/0017361, WO01/93642, WO01/39234, U.S. Pat. No. 6,458,475, WO02/071813, U.S. Pat. No. 6,573,651, US2002/0197511, WO02/074015, U.S. Pat. No. 6,451,455, US2003/0072964, US2003/0068528, U.S. Pat. Nos. 6,413,656, 6,515,298, 6,451,415, 6,097,147, US2003/0124381, US2003/0059646, US2003/0054198, EP1239526, EP1238981, EP1244155, US2002/0100906, US2003/0068526, US2003/0068535, JP2003073387, JP2003073388, US2003/0141809, US2003/0040627, JP2003059667, JP2003073665 and US2002/0121638.

The emission wavelengths of cyclometallated Ir(III) complexes of the type $IrL_3$ and $IrL_2L'$, such as the green-emitting fac-tris(2-phenylpyridinato-N,$C^{2'}$)iridium(III) and bis(2-phenylpyridinato-N,$C^{2'}$)Iridium(III) (acetylacetonate) may be shifted by substitution of electron donating or withdrawing groups at appropriate positions on the cyclometallating ligand L, or by choice of different heterocycles for the cyclometallating ligand L. The emission wavelengths may also be shifted by choice of the ancillary ligand L'. Examples of red emitters are the bis(2-(2'-benzothienyl)pyridinato-N,$C^{3'}$)iridium(El)(acetylacetonate) and tris(1-phenylisoquinolinato-N,C)iridium(III). A blue-emitting example is bis(2-(4,6-difluorophenyl)-pyridinato-N,$C^{2'}$)Iridium(III)(picolinate).

Red electrophosphorescence has been reported, using bis (2-(2'-benzo[4,5-a]thienyl)pyridinato-N, $C^3$)iridium(acetylacetonate)[Btp$_2$Ir(acac)] as the phosphorescent material (Adachi, C., Lamansky, S., Baldo, M. A., Kwong, R. C., Thompson, M. E., and Forrest, S. R., App. Phys. Lett., 78, 1622 1624 (2001).

Other important phosphorescent materials include cyclometallated Pt(II) complexes such as cis-bis(2-phenylpyridinato-N,$C^{2'}$)platinum(II), cis-bis(2-(2'-thienyl)pyridinato-N, $C^{3'}$)platinum(II), cis-bis(2-(2'-thienyl)quinolinato-N,$C^{5'}$) platinum(II), or (2-(4,6-difluorophenyl)pyridinato-NC2') platinum(II)acetylacetonate. Pt(II)porphyrin complexes such as 2,3,7,8,12,13,17,18-octaethyl-21H,23H-porphine platinum(H) are also useful phosphorescent materials.

Still other examples of useful phosphorescent materials include coordination complexes of the trivalent lanthanides such as $Th^{3+}$ and $Eu^{3+}$ (J. Kido et al, Appl. Phys. Lett., 65, 2124 (1994)).

The amount of the phosphorescent material in the light-emitting layer is in general less than 30% by weight, preferably less than 20% by weight, particularly preferred 3 to 12% by weight.

Blocking Layers

In addition to suitable hosts, an OLED device employing a phosphorescent material often requires at least one exciton or hole blocking layers to help confine the excitons or electron-hole recombination centers to the light-emitting layer comprising the host and phosphorescent material, or to reduce the number of charge carriers (electrons or holes). In one embodiment, such a blocking layer would be placed between the electron-transporting layer and the light-emitting layer. In this case, the ionization potential of the blocking layer should be such that there is an energy barrier for hole migration from the host into the electron-transporting layer, while the electron affinity should be such that electrons pass more readily from the electron-transporting layer into the light-emitting layer comprising host and phosphorescent material. It is further desired, but not absolutely required, that the triplet energy of the blocking material be greater than that of the phosphorescent material. Suitable hole-blocking materials are described in WO00/70655 and WO01/93642. Two examples of useful materials are bathocuproine (BCP) and bis(2-methyl-8-quinolinolato)(4-phenylphenolato)aluminum(III) (BAlQ). Metal complexes other than Balq are also known to block holes and excitons as described in US20030068528. US20030175553 describes the use of fac-tris(1-phenylpyrazolato-N,C2)iridium(III) (Irppz) in an electron/exciton blocking layer.

Embodiments of the invention can provide advantageous features such as operating efficiency, higher luminance, color hue, low drive voltage, and improved operating stability. Embodiments of the organometallic compounds useful in the invention can provide a wide range of hues including those useful in the emission of white light (directly or through filters to provide multicolor displays).

General Device Architecture

The compounds of the present invention can be employed in many OLED device configurations using small molecule materials, oligomeric materials, polymeric materials, or combinations thereof. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

There are numerous configurations of the organic layers. The essential requirements of an OLED are an anode, a cathode, and an organic light-emitting layer located between the anode and cathode. Additional layers may be employed as more fully described hereafter.

A typical structure, especially useful for of a small molecule device, is comprised of a substrate, an anode, a hole-injecting layer, a hole-transporting layer, a light-emitting layer, a hole- or exciton-blocking layer, an electron-transporting layer, and a cathode. These layers are described in detail below. Note that the substrate may alternatively be located adjacent to the cathode, or the substrate may actually constitute the anode or cathode. The organic layers between the anode and cathode are conveniently referred to as the organic EL element. Also, the total combined thickness of the organic layers is desirably less than 500 nm.

Substrate

The substrate can either be light transmissive or opaque, depending on the intended direction of light emission. The light transmissive property is desirable for viewing the EL emission through the substrate. Transparent glass or plastic is commonly employed in such cases. The substrate can be a complex structure comprising multiple layers of materials. This is typically the case for active matrix substrates wherein TFTs are provided below the OLED layers. It is still necessary that the substrate, at least in the emissive pixilated areas, be comprised of largely transparent materials such as glass or polymers. For applications where the EL emission is viewed through the top electrode, the transmissive characteristic of the bottom support is immaterial, and therefore can be light transmissive, light absorbing or light reflective. Substrates for use in this case include, but are not limited to, glass, plastic, semiconductor materials, silicon, ceramics, and circuit board materials. Again, the substrate can be a complex structure comprising multiple layers of materials such as found in active matrix TFT designs. It is necessary to provide in these device configurations a light-transparent top electrode.

Anode

When the desired electroluminescent light emission (EL) is viewed through the anode, the anode should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode. For applications where EL emission is viewed only through the cathode, the transmissive characteristics of the anode are immaterial and any conductive material can be used, transparent, opaque or reflective. Example conductors for this application include, but are not limited to, gold, iridium, molybdenum, palladium, and platinum. Desired anode materials are commonly deposited by any suitable means such as evaporation, sputtering, chemical vapor deposition, or electrochemical means. Anodes can be patterned using well-known photolithographic processes. Optionally, anodes may be polished prior to application of other layers to reduce surface roughness so as to minimize shorts or enhance reflectivity.

Cathode

When light emission is viewed solely through the anode, the cathode used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One useful cathode material is comprised of a Mg:Ag alloy wherein the percentage of silver is in the range of 1 to 20%, as described in U.S. Pat. No. 4,885,221. Another suitable class of cathode materials includes bilayers comprising the cathode and a thin electron-injection layer (EIL) in contact with an organic layer (e.g., an electron transporting layer (ETL)) which is capped with a thicker layer of a conductive metal. Here, the EIL preferably includes a low work function metal or metal salt, and if so, the thicker capping layer does not need to have a low work function. One such cathode is comprised of a thin layer of LiF followed by a thicker layer of Al as described in U.S. Pat. No. 5,677,572. An ETL material doped with an alkali metal, for example, Li-doped Alq, is another example of a useful EIL. Other useful cathode material sets include, but are not limited to, those disclosed in U.S. Pat. Nos. 5,059,861, 5,059,862 and 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in U.S. Pat. Nos. 4,885,211, 5,247,190, JP 3,234,963, U.S. Pat. Nos. 5,703,436, 5,608,287, 5,837,391, 5,677,572, 5,776, 622, 5,776,623, 5,714,838, 5,969,474, 5,739,545, 5,981,306, 6,137,223, 6,140,763, 6,172,459, EP1076368, U.S. Pat. Nos. 6,278,236 and 6,284,3936. Cathode materials are typically deposited by any suitable method such as evaporation, sputtering, or chemical vapor deposition. When needed, patterning can be achieved through many well known methods including, but not limited to, through-mask deposition, integral shadow masking as described in U.S. Pat. No. 5,276,380 and EP0732868, laser ablation, and selective chemical vapor deposition.

Hole-Injecting Layer (HIL)

A hole-injecting layer may be provided between anode and hole-transporting layer. The hole-injecting material can serve to improve the film formation property of subsequent organic layers and to facilitate injection of holes into the hole-transporting layer. Suitable materials for use in the hole-injecting layer include, but are not limited to, porphyrinic compounds as described in U.S. Pat. No. 4,720,432, plasma-deposited fluorocarbon polymers as described in U.S. Pat. No. 6,208, 075, and some aromatic amines, for example, m-MTDATA (4,4',4"-tris[(3-methylphenyl)phenylamino]triphenylamine). Alternative hole-injecting materials reportedly useful in organic EL devices are described in EP0891121 and EP1029909.

Hole-Transporting Layer (HTL)

The hole-transporting layer of the organic EL device contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated in U.S. Pat. No. 3,180,730. Other suitable triarylamines substituted with one or more vinyl radicals and/or comprising at least one active hydrogen containing group are disclosed in U.S. Pat. Nos. 3,567,450 and 3,658,520. A more preferred class of aromatic tertiary amines are those which include at least two aromatic tertiary amine moieties as described in U.S. Pat. Nos. 4,720, 432 and 5,061,569. Such compounds include those represented by structural formula

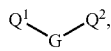

(A)

wherein $Q^1$ and $Q^2$ are independently selected aromatic tertiary amine moieties and G is a linking group such as an arylene, cycloalkylene, or alkylene group of a carbon to carbon bond. In one embodiment, at least one of $Q^1$ or $Q^2$ contains a polycyclic fused ring structure, e.g., a naphthalene. When G is an aryl group, it is conveniently a phenylene, biphenylene, or naphthalene moiety.

A useful class of triarylamines satisfying structural formula (A) and containing two triarylamine moieties is represented by structural formula

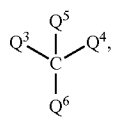

(B)

where $Q^3$ and $Q^4$ each independently represents a hydrogen atom, an aryl group, or an alkyl group or $Q^3$ and $Q^4$ together represent the atoms completing a cycloalkyl group; and $Q^5$ and $Q^6$ each independently represents an aryl group, which is in turn substituted with a diaryl substituted amino group, as indicated by structural formula

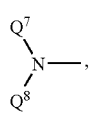

(C)

wherein $Q^7$ and $Q^8$ are independently selected aryl groups. In one embodiment, at least one of $Q^7$ or $Q^8$ contains a polycyclic fused ring structure, e.g., a naphthalene.

Another class of aromatic tertiary amines are the tetraaryldiamines. Desirable tetraaryldiamines include two diarylamino groups, such as indicated by formula (C), linked through an arylene group. Useful tetraaryldiamines include those represented by formula

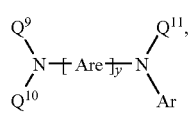

(D)

wherein each Are is an independently selected arylene group, such as a phenylene or anthracene moiety, n is an integer of from 1 to 4, and Ar, $Q^9$, $Q^{10}$, and $Q^{11}$ are independently selected aryl groups. In a typical embodiment, at least one of Ar, $Q^9$, $Q^{10}$, and $Q^{11}$ is a polycyclic fused ring structure, e.g., a naphthalene. The various alkyl, alkylene, aryl, and arylene moieties of the foregoing structural formulae (A), (B), (C), (D), can each in turn be substituted. Typical substituents include alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms, e.g. cyclopentyl, cyclohexyl, and cycloheptyl ring structures. The aryl and arylene moieties are usually phenyl and phenylene moieties.

The hole-transporting layer can be formed of a single or a mixture of aromatic tertiary amine compounds. Specifically, one may employ a triarylamine, such as a triarylamine satisfying the formula (B), in combination with a tetraaryldiamine, such as indicated by formula (D). When a triarylamine is employed in combination with a tetraaryldiamine, the latter is positioned as a layer interposed between the triarylamine and the electron injecting and transporting layer. Illustrative of useful aromatic tertiary amines are the following: 1,1-Bis(4-di-p-tolylaminophenyl)cyclohexane, 1,1-bis(4-di-p-tolylaminophenyl)-4-phenylcyclohexane, N,N,N',N'-tetraphenyl-4,4'''-diamino-1,1':4',1'':4'',1'''-quaterphenyl bis(4-dimethylamino-2-methylphenyl)phenylmethane, 1,4-bis[2-[4-[N,N-di(p-toly)amino]phenyl]vinyl]benzene (BD-TAPVB), N,N,N',N'-tetra-p-tolyl-4,4'-diaminobiphenyl, N,N,N',N'-tetraphenyl-4,4'-diaminobiphenyl, N,N,N',N'-tetra-1-naphthyl-4,4'-diaminobiphenyl, N,N,N',N'-tetra-2-naphthyl-4,4'-diaminobiphenyl, N-phenylcarbazole, 4,4'-bis[N-(1-naphthyl)-N-phenylamino]biphenyl (NPB), 4,4'-bis[N-(1-naphthyl)-N-(2-naphthyl)amino]biphenyl (TNB), 4,4'-bis[N-(1-naphthyl)-N-phenylamino]p-terphenyl, 4,4'-bis[N-(2-naphthyl)-N-phenylamino]biphenyl, 4,4'-bis[N-(3-acenaphthenyl)-N-phenylamino]biphenyl, 1,5-bis[N-(1-naphthyl)-N-phenylamino]naphthalene, 4,4'-bis[N-(9-anthryl)-N-phenylamino]biphenyl, 4,4'-bis[N-(1-anthryl)-N-phenylamino]-p-terphenyl, 4,4'-bis[N-(2-phenanthryl)-N-phenylamino]biphenyl, 4,4'-bis[N-(8-fluoranthenyl)-N-phenylamino]biphenyl, 4,4'-bis[N-(2-pyrenyl)-N-phenylamino]biphenyl, 4,4'-bis[N-(2-naphthacenyl)-N-phenylamino]biphenyl, 4,4'-bis[N-(2-perylenyl)-N-phenylamino]biphenyl, 4,4'-bis[N-(1-coronenyl)-N-phenylamino]biphenyl, 2,6-bis(di-p-tolylamino)naphthalene, 2,6-bis[di-(1-naphthyl)amino]naphthalene, 2,6-bis[N-(1-naphthyl)-N-(2-naphthyl)amino]naphthalene, N,N,N',N'-tetra(2-naphthyl)-4,4''-diamino-p-terphenyl, 4,4'-bis {N-phenyl-N-[4-(1-naphthyl)-phenyl]amino}biphenyl, 2,6-bis[N,N-di(2-naphthyl)amino]fluorine, 4,4',4''-tris[(3-methylphenyl)phenylamino]triphenylamine (MTDATA), and 4,4'-Bis[N-(3-methylphenyl)-N-phenylamino]biphenyl (TPD). A hole transport layer may be used to enhance conductivity. NPD and TPD are examples of intrinsic hole transport layers. An example of a p-doped hole transport layer is m-MTDATA doped with $F_4$-TCNQ at a molar ratio of 50:1 as disclosed in U.S. Pat. No. 6,337,102 or DE10058578.

Another class of useful hole-transporting materials includes polycyclic aromatic compounds as described in EP1009041. Tertiary aromatic amines with more than two amine groups may be used including oligomeric materials. In addition, polymeric hole-transporting materials can be used such as poly(N-vinylcarbazole) (PVK), polythiophenes, polypyrrole, polyaniline, and copolymers such as poly(3,4-ethylenedioxythiophene)/poly(4-styrenesulfonate) also called PEDOT/PSS.

Fluorescent Light-Emitting Materials and Layers (LEL)

In addition to the phosphorescent materials, other light emitting materials may be used in the OLED device, including fluorescent materials. Although the term "fluorescent" is commonly used to describe any light emitting material, in this case we are referring to a material that emits light from a singlet excited state. Fluorescent materials may be used in the same layer as the phosphorescent material, in adjacent layers, in adjacent pixels, or any combination. Care must be taken not to select materials that will adversely affect the performance of the phosphorescent materials. One skilled in the art will understand that triplet excited state energies of materials in the same layer as the phosphorescent material or in an adjacent layer must be appropriately set so as to prevent unwanted quenching. As more fully described in U.S. Pat. Nos. 4,769,292 and 5,935,721, the light-emitting layer (LEL) of the organic EL element includes a luminescent fluorescent or phosphorescent material where electroluminescence is produced as a result of electron-hole pair recombination in this region. The light-emitting layer can be comprised of a single material, but more commonly consists of a host material doped with a guest emitting material or materials where light emission comes primarily from the emitting materials and can be of any color. The host materials in the light-emitting layer can be an electron-transporting material, as defined below, a hole-transporting material, as defined above, or another material or combination of materials that support hole-electron recombination. Fluorescent emitting materials are typically incorporated at 0.01 to 10% by weight of the host material. The host and emitting materials can be small non-polymeric molecules or polymeric materials such as polyfluorenes and polyvinylarylenes (e.g., poly(p-phenylenevinylene), PPV). In the case of polymers, small molecule emitting materials can be molecularly dispersed into a polymeric host, or the emitting materials can be added by copolymerizing a minor constituent into a host polymer. Host materials may be mixed together in order to improve film formation, electrical properties, light emission efficiency, lifetime, or manufacturability. The host may comprise a material that has good hole-transporting properties and a material that has good electron-transporting properties.

Host and emitting materials known to be of use include, but are not limited to, those disclosed in U.S. Pat. Nos. 4,768,292, 5,141,671, 5,150,006, 5,151,629, 5,405,709, 5,484,922, 5,593,788, 5,645,948, 5,683,823, 5,755,999, 5,928,802, 5,935,720, 5,935,721, and 6,020,078.

Metal complexes of 8-hydroxyquinoline and similar derivatives (Formula E) constitute one class of useful host compounds capable of supporting electroluminescence, and are particularly suitable for light emission of wavelengths longer than 500 nm, e.g., green, yellow, orange, and red.

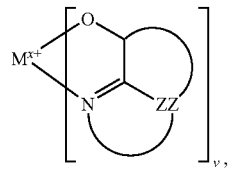

wherein M represents a metal; v is an integer of from 1 to 4; and ZZ independently in each occurrence represents the atoms completing a nucleus having at least two fused aromatic rings. From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such aluminum or gallium, or a transition metal such as zinc or zirconium. Generally any monovalent, divalent, trivalent, or tetravalent metal known to be a useful chelating metal can be employed. ZZ completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:
CO-1: Aluminum trisoxine [alias, tris(8-quinolinolato)aluminum(III)]
CO-2: Magnesium bisoxine [alias, bis(8-quinolinolato)magnesium(II)]
CO-3: Bis[benzo{f}-8-quinolinolato]zinc(II)
CO-4: Bis(2-methyl-8-quinolinolato)aluminum(III)-μ-oxo-bis(2-methyl-8-quinol-inolato)aluminum(III)
CO-5: Indium trisoxine [alias, tris(8-quinolinolato)indium]
CO-6: Aluminum tris(5-methyloxine) [alias, tris(5-methyl-8-quinolinolato)aluminum(III)]
CO-7: Lithium oxine [alias, (8-quinolinolato)lithium(I)]
CO-8: Gallium oxine [alias, tris(8-quinolinolato)gallium(III)]
CO-9: Zirconium oxine [alias, tetra(8-quinolinolato)zirconium(IV)]

Useful fluorescent emitting materials include, but are not limited to, derivatives of anthracene, tetracene, xanthene, perylene, rubrene, coumarin, rhodamine, and quinacridone, dicyanomethylenepyran compounds, thiopyran compounds, polymethine compounds, pyrilium and thiapyrilium compounds, fluorene derivatives, periflanthene derivatives, indenoperylene derivatives, bis(azinyl)amine boron compounds, bis(azinyl)methane compounds, and carbostyryl compounds. Illustrative examples of useful materials include, but are not limited to, compounds L1 to L52 described in U.S. Pat. No. 7,090,930B2.

Electron-Transporting Layer (ETL)

Preferred thin film-forming materials for use in forming the electron-transporting layer of the organic EL devices of this invention are metal chelated oxinoid compounds, including chelates of oxine itself (also commonly referred to as 8-quinolinol or 8-hydroxyquinoline). Such compounds help to inject and transport electrons and exhibit both high levels of performance and are readily fabricated in the form of thin films. Exemplary of contemplated oxinoid compounds are those satisfying structural formula (E), previously described. Other electron-transporting materials include various butadiene derivatives as disclosed in U.S. Pat. No. 4,356,429 and various heterocyclic optical brighteners as described in U.S. Pat. No. 4,539,507. Benzazoles satisfying structural formula (G) are also useful electron transporting materials. Triazines are also known to be useful as electron transporting materials. Doping may be used to enhance conductivity. Alq$_3$ is an example of an intrinsic electron transport layer. An example of an n-doped electron transport layer is BPhen doped with Li at a molar ratio of 1:1, as disclosed in U.S. Pat. No. 6,337,102.

Deposition of Organic Layers

The organic materials mentioned above are suitably deposited by any means suitable for the form of the organic materials. In the case of small molecules, they are conveniently deposited through thermal evaporation, but can be deposited by other means such as from a solvent with an optional binder to improve film formation. If the material is soluble or in oligomeric/polymeric form, solution processing is usually preferred e.g. spin-coating, ink-jet printing. Dendrimer substituents may be used to enhance the ability of small molecules to undergo solution processing. Patterned deposition can be achieved using shadow masks, integral shadow masks (U.S. Pat. No. 5,294,870), spatially-defined thermal dye transfer from a donor sheet (U.S. Pat. Nos. 5,688,551, 5,851,709 and 6,066,357) and inkjet method (U.S. Pat. No. 6,066,357).

Encapsulation

Most OLED devices are sensitive to moisture or oxygen, or both, so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as $SiO_x$, Teflon, and alternating inorganic/polymeric layers are known in the art for encapsulation.

Devices fabricated in accordance with embodiments of the invention may be incorporated into a wide variety of consumer products, including flat panel displays, computer monitors, televisions, billboards, lights for interior or exterior illumination and/or signalling, fully transparent displays, flexible displays, laser printers, cell phones, personal digital assistants (PDAs), laptop computers, digital cameras, camcorders, viewfinders, micro-displays, vehicles, theatre or stadium screen, or a sign. Various control mechanism may be used to control devices fabricated in accordance with the present invention, including passive matrix and active matrix.

Various features and aspects of the present invention are illustrated further in the examples that follow. While these examples are presented to show one skilled in the art how to operate within the scope of this invention, they are not to serve as a limitation on the scope of the invention where such scope is only defined in the claims. Unless otherwise indicated in the following examples and elsewhere in the specification and claims, all parts and percentages are by weight, temperatures are in degrees centigrade and pressures are at or near atmospheric.

EXAMPLES

Example 1

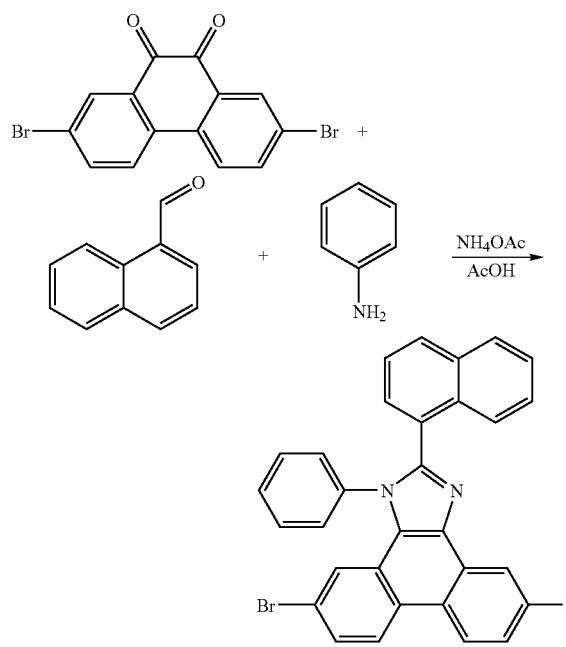

a.) 1.00 g (2.73 mmol) 2,7-dibromo-phenanthrene-9,10-dione, 470 mg (3.01 mmol) naphthalene-1-carbaldehyde, 510 mg (5.46 mmol) phenylamine are dissolved in 25 ml acetic acid (>99%). 1.05 g ammonium acetate are added under nitrogen. The reaction mixture is stirred for 18 h at 130° C. and then cooled to 25° C. The product is filtered off, washed with water and a sodium hydrogencarbonate solution (yield: 1.38 g (76%)).

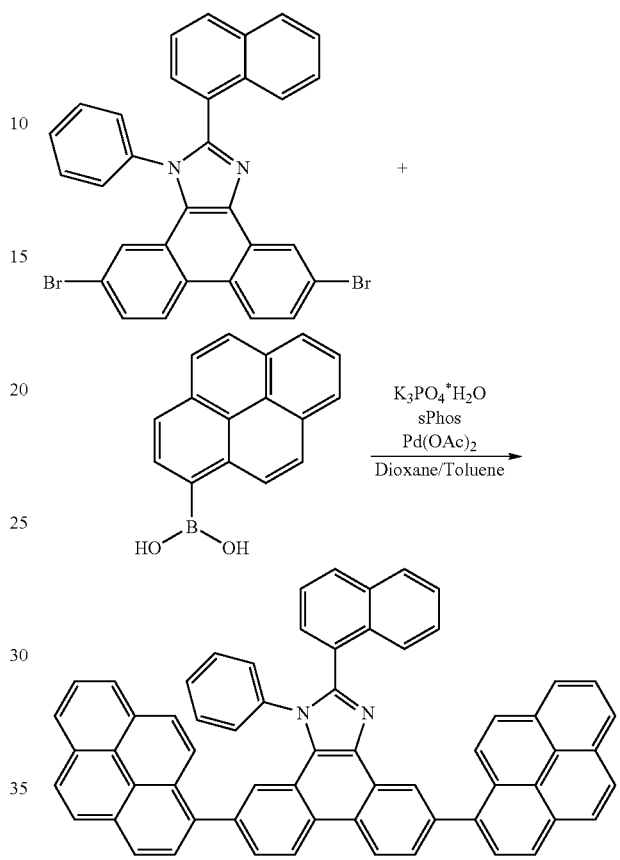

b) To 2.50 g (4.32 mmol) of the di-bromide of example 1a and 2.34 g (9.51 mmol) 1-pyren boronic acid 15 ml dioxane and 40 ml toluene are added. The reaction mixture is degassed. 107 mg (0.26 mmol) 2-Dicyclohexylphosphino-2',6'-di-methoxybiphenyl and 97 mg (0.043 mmol) palladium (II)acetate are added. The reaction mixture is degassed with argon. A degassed solution of 5.24 g (21.6 mmol) potassium phosphate tribasic monohydrate in 8 ml water is added. The reaction mixture is refluxed for 4 h. The product is filtered on silica gel with terahydrofuran (THF). The solvent is removed and the product is soxhlet extracted with methyl-ethyl-ketone (yield: 2.47 g (70%)).

Example 2

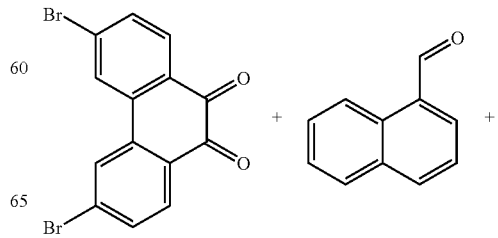

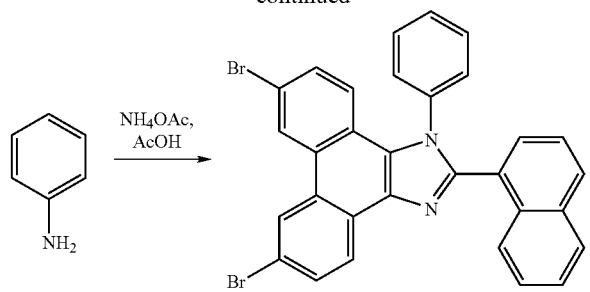
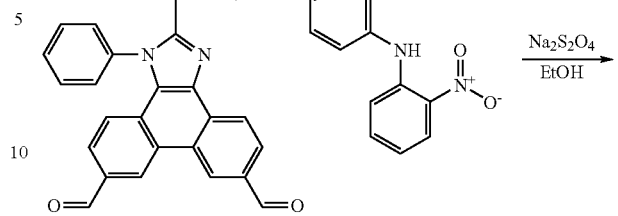

a) 400 ml glacial acetic acid are added to 20.0 g (54.6 mmol) 3,6-dibromo-phenanthrene-9,10-dione, 10.2 g (65.6 mmol) naphthalene-1-carbaldehyde, 21.2 g (164 mmol) phenyl amine and 12.6 g (164 mmol) ammonium acetate. The reaction mixture is refluxed for 2 h under nitrogen. 200 ml ethanol is added, the product is filtered off and washed with ethanol (yield 25.3 g (80%); melting point: 248-249° C.).

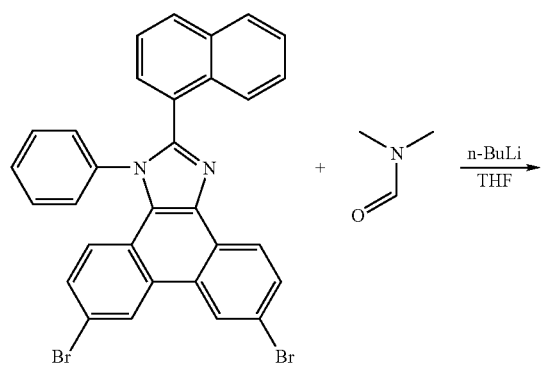
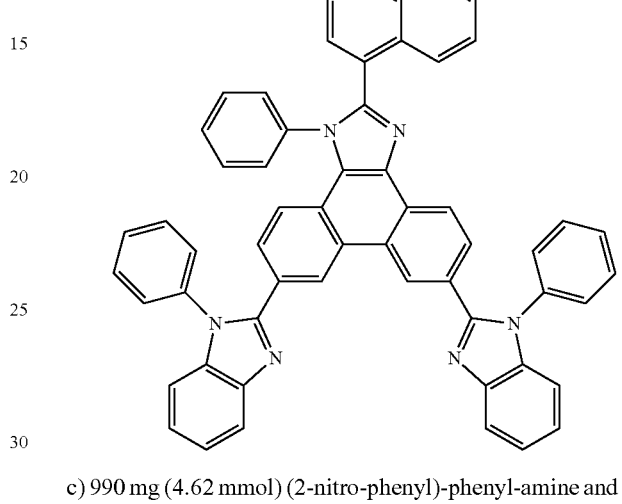

c) 990 mg (4.62 mmol) (2-nitro-phenyl)-phenyl-amine and 2.19 g (12.6 mmol) sodium dithionite are added to 1.00 g (2.10 mmol) of the product of example 2b in 30 ml ethanol. The reaction mixture is refluxed under nitrogen for 5 h. The product is filtered off and is washed with ethanol. A column chromatography with toluene/ethyl acetate 2/1 over silica gel gives 550 mg of the product. The product is refluxed in 20 ml dibuthylether for 1 h and is filtered off (yield: 350 mg (21%); melting point: 344° C.).

Example 3

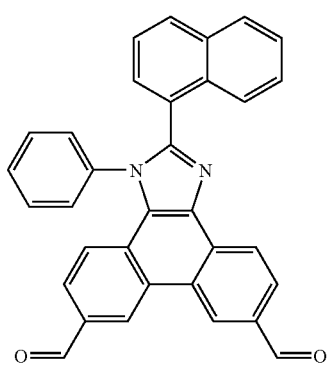

b) 5.00 g (8.65 mmol) of the product of example 2a are dissolved in 60 ml water free (THF) under argon. n-Butyl lithium is added to this solution 7.6 ml at −78° C. The reaction mixture is stirred for 20 min and than 6.32 g DMF (dimethylformamid) are added. The reaction mixture is stirred for 20 min at −78° C. and is then warmed up to 25° C. After 2 h the reaction mixture is poured into water. The water phase is extracted with dichloromethane. The organic phase is dried with magnesium sulfate. The solvent is removed in vacuum. The product is refluxed in dibutylether for 1 h and filtered off (yield: 1.95 g (47%); melting point: 297-314° C.).

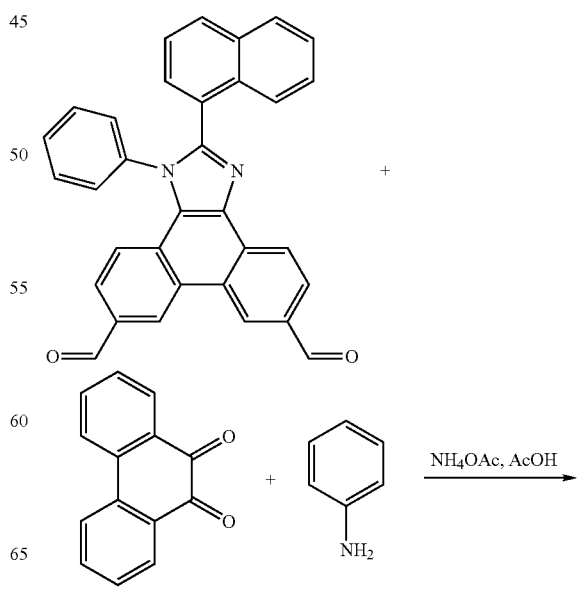

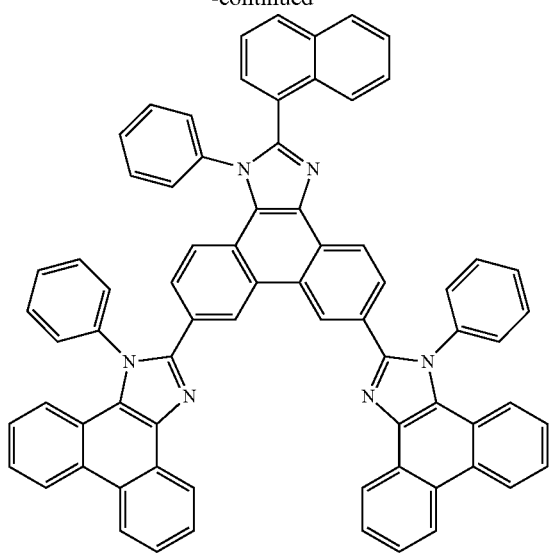

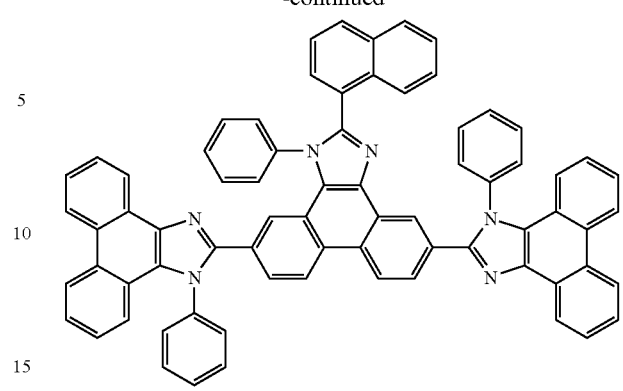

The product is prepared according to example 3 starting form the product of example 1a (melting point: >400° C.; glass transition point: 255° C.).

800 mg (3.83 mmol) phenanthrene-9,10-dione, 430 mg (4.60 mmol) phenyl amine and 590 mg (7.66 mmol) ammonium acetate are added to 730 mg (1.53 mmol) of the product of example 2b in 60 ml glacial acetic acid. The reaction mixture is refluxed for 1 h under nitrogen and poured into water. The product is filtered off, decocted with 20 ml methylethylketone, two times with 20 ml dibuthylether and with 20 ml methylethylketone (yield: 760 mg (49%); melting point: 427° C.).

Example 4

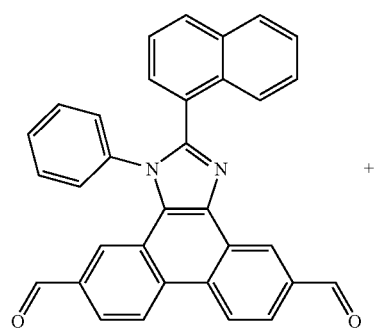

+

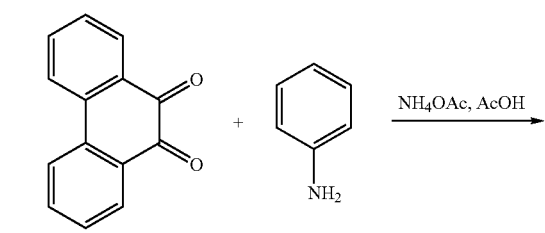

Example 5

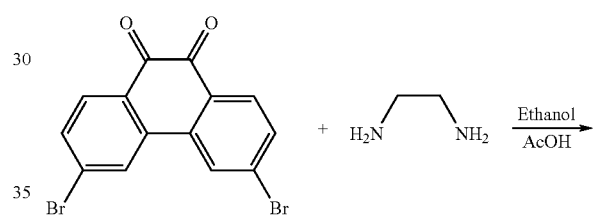

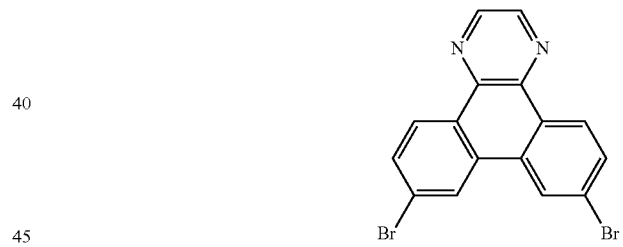

a) The product is prepared as described in Example 4 of PCT/EP2007/059218.

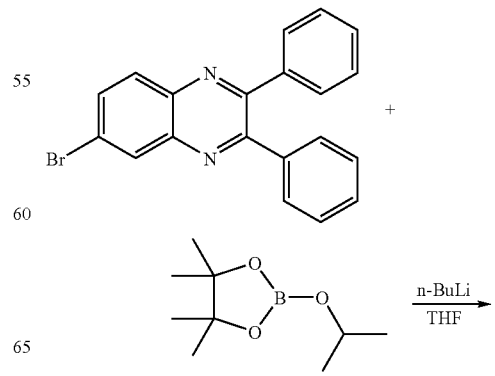

-continued

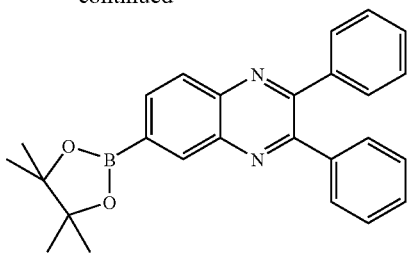

b) 5.00 g (13.8 mmol) 6-bromo-2,3-diphenyl-quinoxaline are dissolved in 20 ml water free THF under argon. 6.6 ml (16.6 mmol) n-butyl lithium are added to this solution at −78° C. After 20 min 3.09 g (16.6 mmol) 2-isopropoxy-4,4,5,5-tetramethyl-1,3,2-dioxaborolane are added and the reaction mixture is warmed to 25° C. After 4 h the reaction mixture is poured into water and the water phase is extracted with dichloromethane. The organic phase is dried with magnesium sulphate. The product is used without further purification for the next reaction step.

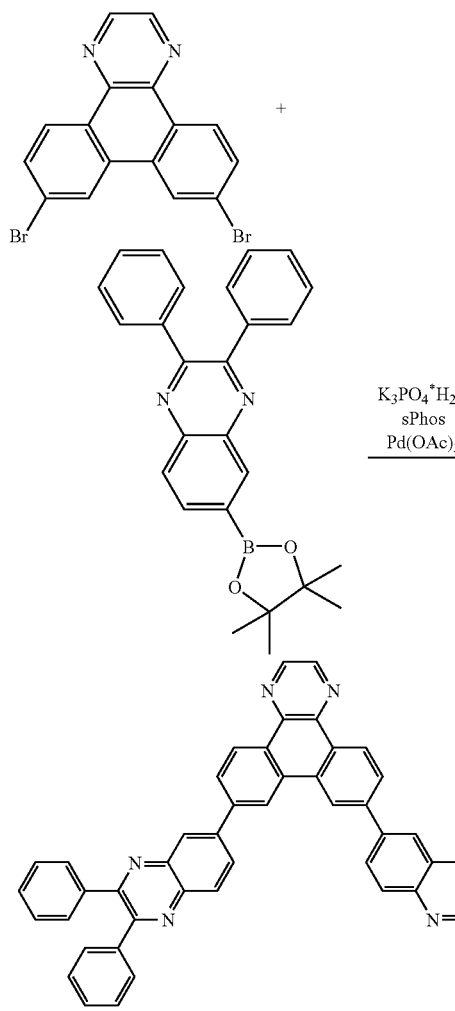

c.) 1.50 g (3.87 mmol) of the product of example 5a and 3.47 g (8.50 mmol) of the product of example 5b are dissolved in 10 ml dioxane and 40 ml toluene. The reaction mixture is degassed with argon. 95 mg (0.23 mmol) 2-dicyclohexylphosphino-2',6'-di-methoxybiphenyl (sPhos) and 8.7 mg (0.04 mmol) palladium(II)acetate are added. The reaction mixture is degassed with argon. A degassed solution of 4.69 g (10.3 mmol) potassium phosphate tribasic monohydrate in 8 ml water is added. The reaction mixture is stirred for 20 h at 90° C. under argon and is cooled to 25° C. The product is filtered off and decocted 3 times with 25 ml toluene (yield: 1.86 g (61%); melting point: 375° C.).

Example 6

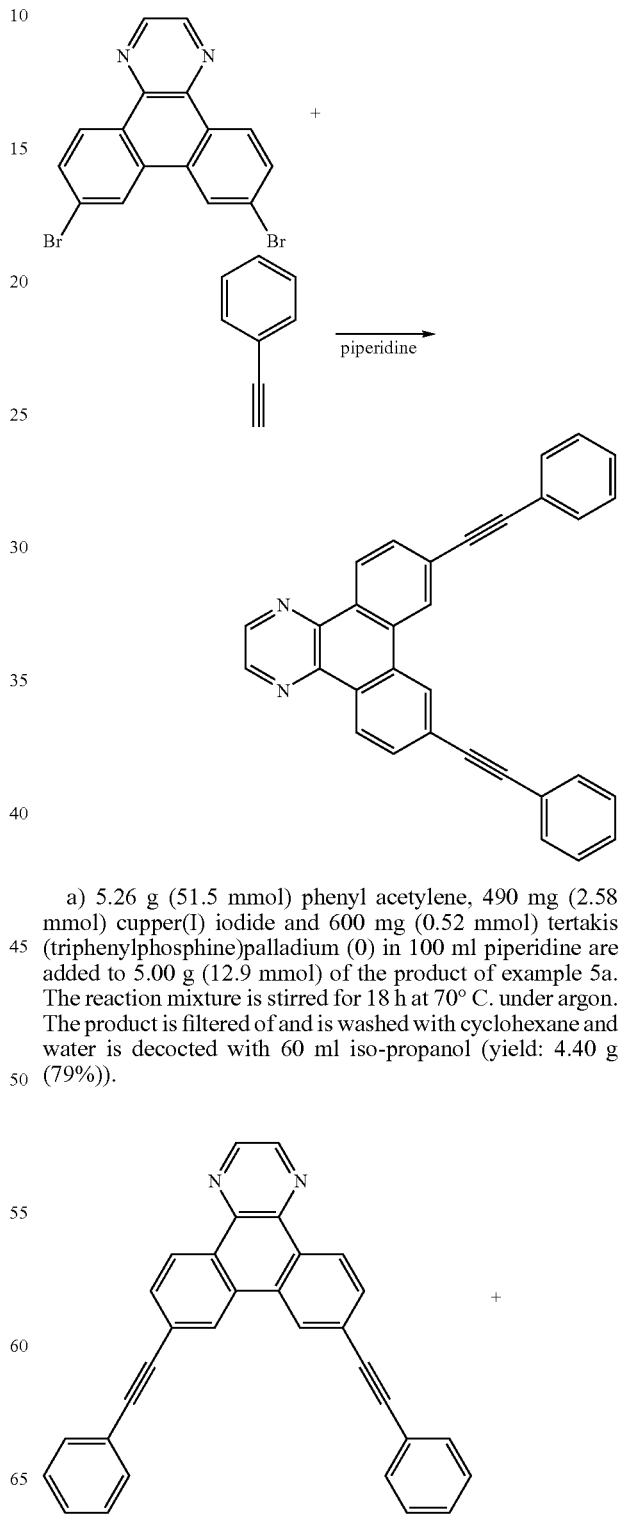

a) 5.26 g (51.5 mmol) phenyl acetylene, 490 mg (2.58 mmol) cupper(I) iodide and 600 mg (0.52 mmol) tertakis (triphenylphosphine)palladium (0) in 100 ml piperidine are added to 5.00 g (12.9 mmol) of the product of example 5a. The reaction mixture is stirred for 18 h at 70° C. under argon. The product is filtered of and is washed with cyclohexane and water is decocted with 60 ml iso-propanol (yield: 4.40 g (79%)).

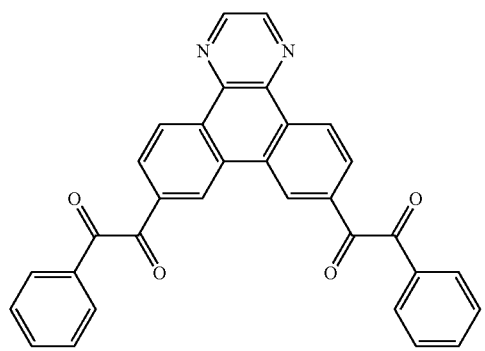

b) 70 ml DMSO are added to 5.10 g (11.9 mmol) of the product of example 6a and 1.80 g (7.11 mmol) iodine. The reaction mixture is stirred at 160° C. for 16 h and is cooled to 25° C. The product is filtered off and is washed with a 1% Na$_2$S$_2$O$_3$ solution and water (yield: 3.45% (60%)).

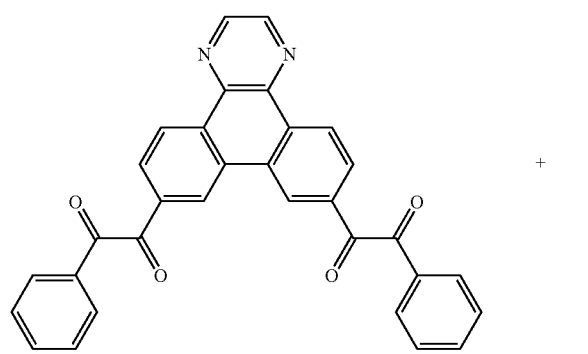

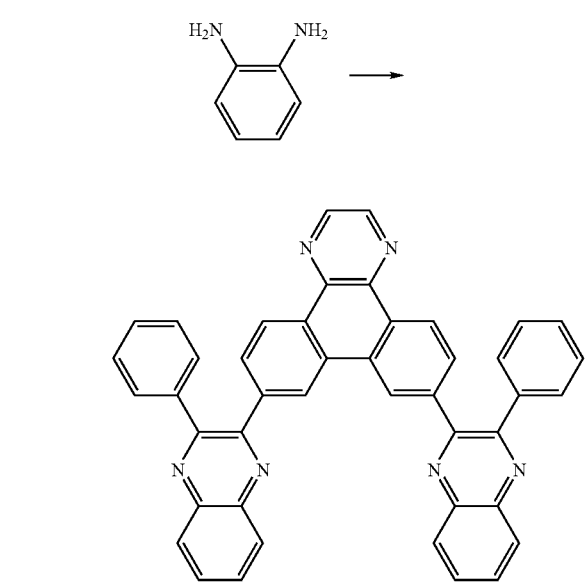

c) 140 ml ethanol and 70 ml chloroform are added to 3.40 g (6.88 mmol) of the product of example 6b and 1.49 g (13.8 mmol) 1,2-phenylendiamine. 15 drops of sulfuric acid (96%) are added and the reaction mixture is stirred at 90° C. for 19 h. The formed product is filtered off, is washed with ethanol, 20% hydrochloric acid and water and is soxhlet extracted with chloroform (yield: 2.34 g (60%); melting point: 339-341° C.).

Example 7

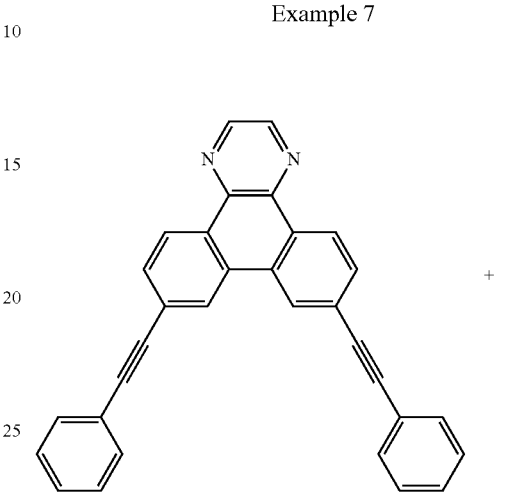

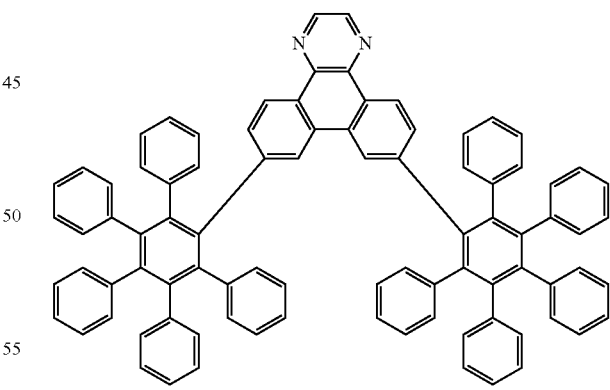

1.96 g (5.11 mmol) tetraphenylpentadienone is added under argon to 1.00 g (2.32 mmol) of the product of example 6a in 15 ml triethylene glycol. The reaction mixture is heated at 250° C. under argon for 16 h and is cooled to 25° C. The product is filtered off, washed with ethanol and dissolved in 20 ml dichloromethane. 10 ml methyl-ethyl-ketone are added and the dichloromethane is distilled off. This procedure is repeated 5 times (yield: 69%; melting point: >400° C.).

Example 8

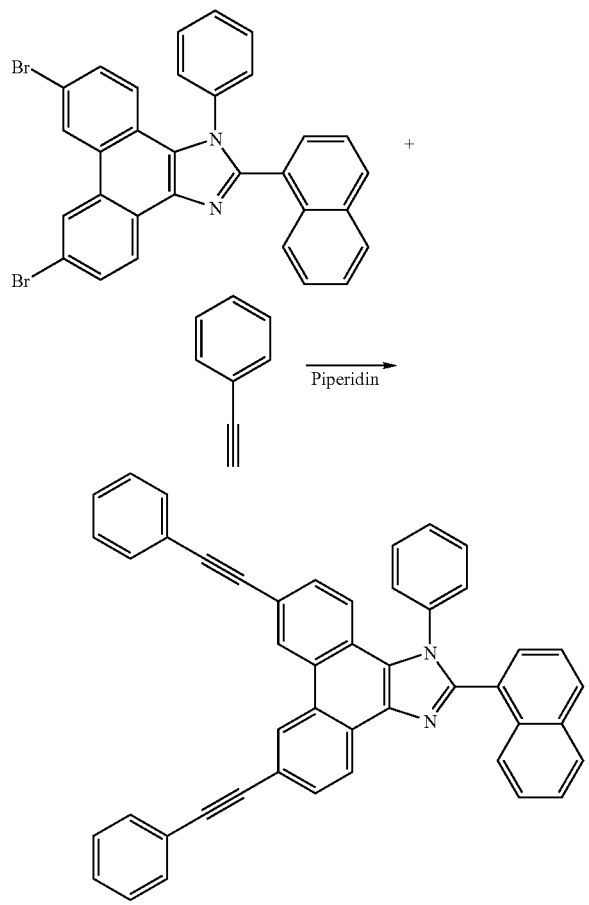

a) 3.16 g (30.9 mmol) ethynyl-benzene, 0.29 g (1.6 mmol) copper (I) iodide and 0.36 g (0.31 mmol) tertakis (triphenylphosphine)palladium (0) are added to 3.00 g (7.73 mmol) of the product of example 2a). 50 ml piperidine are added under argon and the reaction mixture is heated for 20 h at 70° C. The solids are filtered off and washed with toluene. The solvents are removed in vacuum and the residue is decocted in cyclohexane. The solvent is removed and the product is decocted from isopropanol (yield: 34%).

Device Fabrication

Prior to device fabrication, indium tin oxide (ITO) on glass is patterned as 2 mm wide stripes (sheet resistance 20 Ω/square). The substrates are cleaned by sonication in acetone, isopropanol and water for 15 minutes in each solvent. After that, the substrates are dried with a nitrogen steam and treated by $O_2$ vacuum plasma for 5 minutes. Organic layers of the OLEDs are sequentially deposited by thermal evaporation from resistively heated ceramic crucibles at a base pressure of $2 \times 10^{-7}$ Torr at 2 A/s. Host and dopant are co-evaporated from different sources to form a thin film in the range of 30-40 nm thickness. The evaporation rate of each single component source is controlled by a thickness monitor (Inficon) close to the substrate or to the source. All the devices are measured in a nitrogen glove box, immediately after fabrication. Current-voltage and optical measurements are carried out with a Botest equipment. Electroluminescent spectra were measured with an Ocean Optic spectrometer. For all of the experiments a phosphorescent red emitter available under the trade name LT-E713 from Luminescence Technology Corp is used:

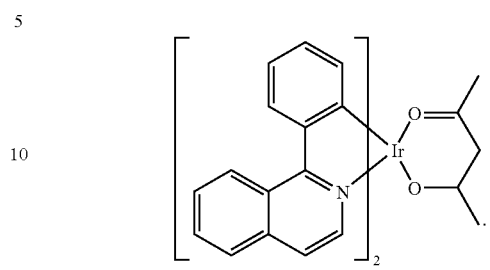

Application Example 1

An OLED is prepared having the following structure from the anode to the cathode: 60 nm of tris(2-naphthylphenylamino) triphenyl-amine (2-TNATA) as hole injection layer, 30 nm of 4,4'-bis[N-1-naphthyl)-N-phenylamino]-biphenyl (α-NPD), 30 nm of the compound (host) of Example 5 doped with 6 wt % of LT-E713 (guest), 10 nm of 1,3,5-bis(phenyl-2-benzimidazolyl)benzene (TPBI) acting as hole blocking layer, 30 nm of tris(8-quinolate)aluminium ($Alq_3$) as electron transport layer, 1 nm LiF capped with 100 nm of aluminium as top electrode.

Application Example 2

An OLED is prepared having the following structure from the anode to the cathode: 25 nm of copperphthalocyanine (CuPc) as hole injection layer, 55 nm of 4,4'-bis[N-81-naphthyl)-N-phenylamino]-biphenyl (α-NPD), 40 nm of the compound (host) of Example 5 doped with 15 wt % of LT-E713, 10 nm of 1,3,5-bis(phenyl-2-benzimidazolyl)benzene (TPBI) acting as hole blocking layer, 30 nm of tris(8-quinolate)aluminium ($Alq_3$) as electron transport layer, 1 nm LiF capped with 100 nm of aluminium as top electrode.

Comparative Application Example 1

The same device structure described in Application Example 2 is used, except that the compound (host) of Example 5 is replaced by bis(2-methyl-8-quinolato)-4-phenyl-phenolate(BAlq).

Application Example 3

The same device structure described in Application Example 1 is used, except that the compound of Example 3 is replaced by the compound of Example 6 (host), wherein the ratio of host to guest is 85:15

Application Example 4

The same device structure described in Application Example 1 is used, except that the compound of Example 3 is replaced by the compound of Example 4 (host), wherein the ratio of host to guest is 85:15.

The current efficiency, power efficiency, voltages for a luminance of 1000 cd/m² and the CIE (x,y) value are shown in the table below.

| | Dopant conc. (wt %) | Current efficiency [cd/A] @1000 cd/m² | Power efficiency [lm/W] @1000 Cd/m² | Voltage [V] @1000 Cd/m² | CIE X | CIE Y |
|---|---|---|---|---|---|---|
| Application Example 1 | 6 | 7.8 | 2.8 | 8.7 | 0.68 | 0.32 |
| Application Example 2 | 15 | 6.1 | 1.7 | 11 | 0.68 | 0.32 |
| Comparative Application Example 1 | 15 | 3.2 | 0.9 | 11.5 | 0.68 | 0.32 |
| Application Example 3 | 15 | 7.8 | 3.0 | 8.2 | 0.68 | 0.32 |
| Application Example 4 | 6 | 5.3 | 2.3 | 7.4 | 0.68 | 0.32 |

The invention claimed is:

1. A compound of the formula

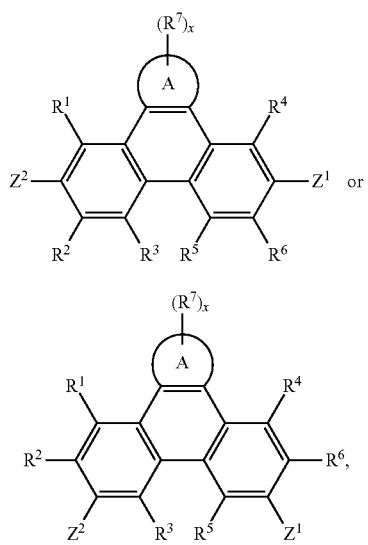

wherein A is

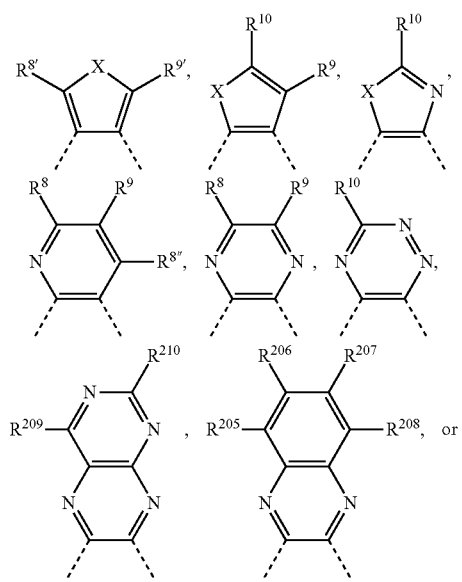

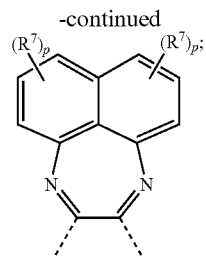

$R^1$, $R^2$, $R^3$, $R^4$, $R^5$ and $R^6$ are independently of each other hydrogen, F, or an organic substituent, or $R^1$ and $R^2$, $R^4$ and $R^6$, $R^2$ and $R^3$, $R^5$ and $R^3$ and/or $R^5$ and $R^6$, which are adjacent to each other, together form an aromatic, or heteroaromatic ring, or ring system, which can optionally be substituted, x is 0, or an integer of 1 to 5;

$R^7$ has the meaning of $R^8$, $R^{8''}$ has the meaning of $R^8$, p is 0, 1, 2, or 3, the dotted line - - - indicates the bonding to the biphenyl unit, $R^8$ and $R^9$ are independently of each other H, CN, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$, or $R^8$ and $R^9$ together form a group

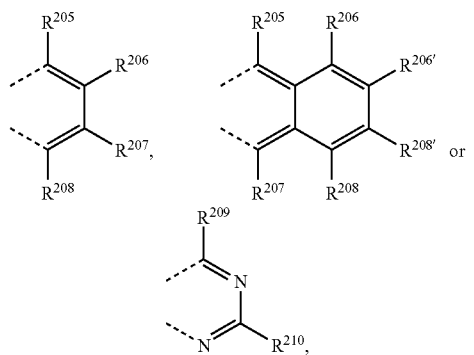

wherein $R^{206'}$, $R^{208'}$, $R^{205}$, $R^{206}$, $R^{207}$, $R^{208}$, $R^{209}$ and $R^{210}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_7$-$C_{25}$aralkyl, CN, or —CO—$R^{28}$, $R^{10}$ is H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —CO—$R^{28}$, $R^{8'}$ and $R^{9'}$ are independently of each other H, CN, —COOR$^{27}$; —CONR$^{25}$R$^{26}$, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$;

$R^{11}$ and $R^{14}$ are independently of each other hydrogen, F, $C_1$-$C_{18}$alkyl, $C_1$-$C_{18}$alkyl which is substituted by E and/or interrupted by D, $C_1$-$C_{18}$perfluoroalkyl, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, CN, or —CO—$R^{28}$, $R^{12}$, $R^{13}$, $R^{15}$ and $R^{16}$ are independently of each other H, halogen, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN or —CO—$R^{28}$, X is O, S, or NR$^{17}$, wherein R$^{17}$ is $C_6$-$C_{18}$aryl; $C_2$-$C_{20}$heteroaryl; $C_6$-$C_{18}$aryl, or $C_2$-$C_{20}$heteroaryl, which are substituted by $C_1$-$C_{18}$alkyl, $C_1$-$C_{18}$perfluoroalkyl, —N($C_6$-$C_{18}$aryl)$_2$, or $C_1$-$C_{18}$alkoxy; $C_1$-$C_{18}$alkyl; or $C_1$-$C_{18}$alkyl which is interrupted by —O—;

or two substituents $R^1$ and $R^2$, $R^4$ and $R^6$, $R^{11}$ and $R^{12}$, and/or $R^{14}$ and $R^{16}$, $R^2$ and $R^3$, $R^5$ and $R^6$, $R^{12}$ and $R^{13}$, and/or $R^{15}$ and $R^{16}$, which are adjacent to each other, together form a group

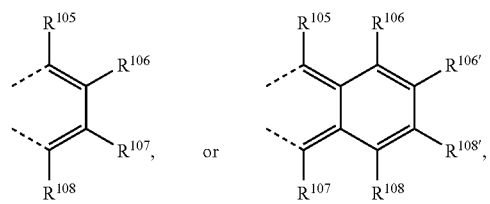

or two substituents $R^{15}$ and $R^{13}$, and/or $R^5$ and $R^3$, which are adjacent to each other, together form a group

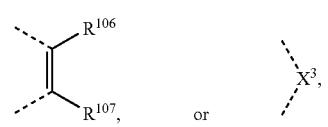

wherein $X^3$ is O, S, C($R^{119}$)($R^{120}$) or NR$^{17}$, wherein $R^{17}$ is as defined above, $R^{105}$, $R^{106}$, $R^{107}$, $R^{108}$, $R^{106'}$ and $R^{108'}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $R^{119}$ and $R^{120}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{119}$ and $R^{120}$ together form a group of formula =CR$^{121}$R$^{122}$, wherein $R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—R$^{127}$, D is —CO—; —COO—; —S—; —SO—; —SO$_2$—; —O—; —NR$^{25}$—; —SiR$^{30}$R$^{31}$—; —POR$^{32}$—; —CR$^{23}$=CR$^{24}$—; or —C≡C—; and E is —OR$^{29}$; —SR$^{29}$; —NR$^{25}$R$^{26}$; —COR$^{28}$; —COOR$^{27}$; —CONR$^{25}$R$^{26}$; —CN; or halogen; G is E, $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, wherein $R^{23}$, $R^{24}$, $R^{25}$ and $R^{26}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or $R^{25}$ and $R^{26}$ together form a five or six membered ring, $R^{27}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{28}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{29}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{30}$ and $R^{31}$ are independently of each other $C_1$-$C_{18}$alkyl, $C_6$-$C_{18}$aryl, or $C_6$-$C_{18}$aryl, which is substituted by $C_1$-$C_{18}$alkyl, $R^{32}$ is $C_1$-$C_{18}$alkyl, $C_6$-$C_{18}$aryl, or $C_6$-$C_{18}$aryl, which is substituted by $C_1$-$C_{18}$alkyl, $Z^1$ and $Z^2$ are independently of each other a group

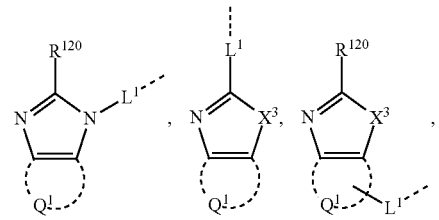

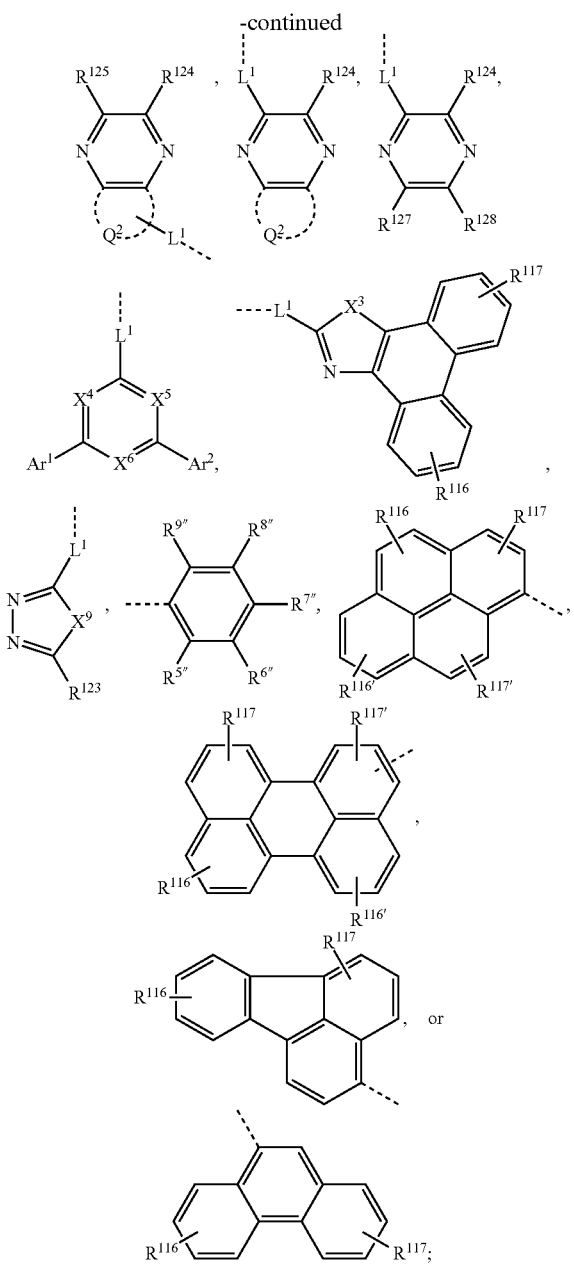

wherein R[5″] is hydrogen, or has the meaning of R[6],

R[6″], R[7″], and R[9″] are independently of each other C$_6$-C$_{18}$aryl; which may optionally be substituted by G; or C$_2$-C$_{20}$heteroaryl, which may optionally be substituted by G, X[3] represents O, S or N—R[121′], X[9] represents O, S or N—R[121′], Q[1] and Q[2] represents atoms necessary for forming a carbocyclic aromatic, or heterocyclic aromatic ring, which can optionally be condensed with other ring(s) to form a condensed ring, and/or can optionally be substituted by G, R[121′] is C$_6$-C$_{18}$aryl; or C$_2$-C$_{20}$heteroaryl; which can optionally be substituted by C$_1$-C$_{18}$alkyl, C$_1$-C$_{18}$perfluoroalkyl, or C$_1$-C$_{18}$alkoxy; C$_1$-C$_{18}$alkyl; or C$_1$-C$_{18}$alkyl which is interrupted by —O—;

R[116], R[116′], R[117] and R[117′] are independently of each other H, halogen, —CN, C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, C$_7$-C$_{25}$aralkyl, —C(=O)—R[127], —C(=O)OR[127], or —C(=O)NR[127]R[126], or substituents R[116], R[116′], R[117] and R[117′], which are adjacent to each other, can form a ring, R[126] and R[127] are independently of each other C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$alkyl; or C$_1$-C$_{18}$alkyl which is interrupted by —O—, R[120], R[123], R[124] and R[125] are independently of each other H, C$_1$-C$_{18}$alkyl, C$_1$-C$_{18}$alkyl which is substituted by E and/or interrupted by D, C$_1$-C$_{18}$perfluoroalkyl, C$_6$-C$_{24}$aryl, which can optionally be substituted by G, C$_2$-C$_{20}$heteroaryl, which can optionally be substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, or C$_7$-C$_{25}$aralkyl, R[128] is H, CN, C$_1$-C$_{18}$alkyl, C$_1$-C$_{18}$alkyl which is substituted by E and/or interrupted by D, C$_1$-C$_{18}$perfluoroalkyl, C$_6$-C$_{24}$aryl, which can optionally be substituted by G, C$_2$-C$_{20}$heteroaryl, which can optionally be substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, or C$_7$-C$_{25}$aralkyl, L[1] is a single bond, —(CR[47]=CR[48])$_{m2}$—, —(Ar[3])$_{m3}$—, —[Ar[3](Y[1])$_{m1}$]$_{m4}$—, —[(Y[1])$_{m1}$Ar[3]]$_{m4}$—, or —[Ar[3](Y[2])$_{m1}$Ar[4]]$_{m4}$—, wherein Y[1] is —(CR[47]=CR[48])—, Y[2] is NR[49], O, S, C=O, C(=O)O, wherein R[49] is H; C$_6$-C$_{18}$aryl which can optionally be substituted by C$_1$-C$_{18}$alkyl, or C$_1$-C$_{18}$alkoxy; C$_1$-C$_{18}$alkyl; or C$_1$-C$_{18}$alkyl which is interrupted by —O—;

R[47] and R[48] are independently of each other hydrogen, fluorine, C$_1$-C$_{20}$alkyl, or C$_6$-C$_{24}$aryl, which can optionally be substituted by G, m1 is an integer of 1 to 10, m2 is an integer of 1 to 10, m3 is an integer of 1 to 5, m4 is an integer of 1 to 5, Ar[3] and Ar[4] are independently of each other arylen, or heteroarylen, which can optionally be substituted, X[4], X[5] and X[6] are independently of each other N, or CH, with the proviso that at least one of the substituents X[4], X[5] and X[6] are N, Ar[1] and Ar[2] are independently of each other C$_6$-C$_{24}$aryl, which can optionally be substituted by G, or C$_2$-C$_{20}$heteroaryl, which can optionally be substituted by G, wherein D, E and G are as defined above, and wherein at least one of Z[1] and Z[2] is an electron deficient heteroaryl group.

2. A compound according to claim 1 of formula

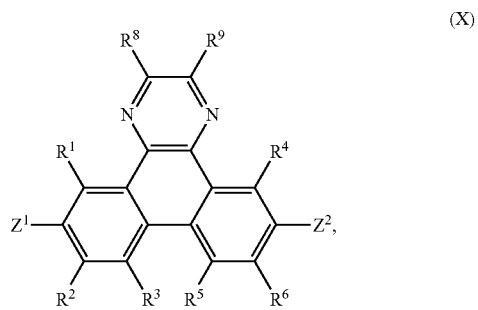

(X)

-continued (XI)
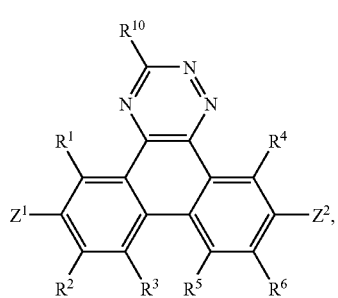

(XII)
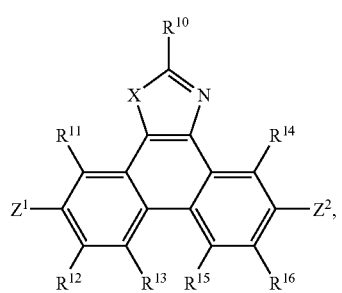

(XIII)
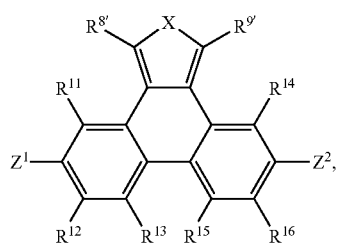

(XVI)
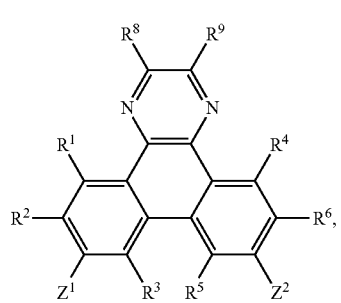

(XVII)
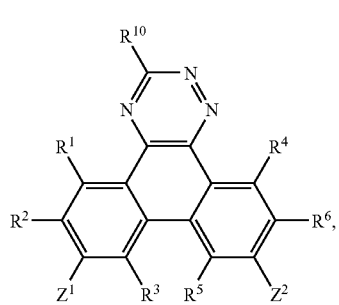

(XVIII)
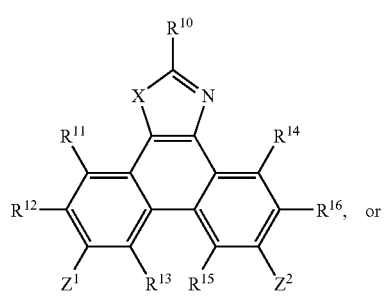

(XIX)
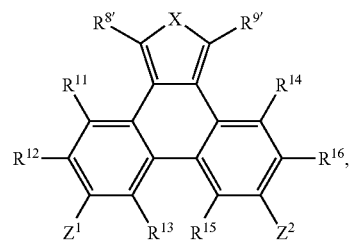

wherein

IV and $R^4$ are independently of each other hydrogen, F, $C_1$-$C_{18}$alkyl, $C_1$-$C_{18}$alkyl which is substituted by E and/or interrupted by D, $C_1$-$C_{18}$perfluoroalkyl, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, CN, or —CO—$R^{28}$, $R^2$, $R^3$, $R^5$ and $R^6$ are independently of each other H, F, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$, $R^8$ and $R^9$ are independently of each other H, CN, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$, or $R^8$ and $R^9$ together form a group

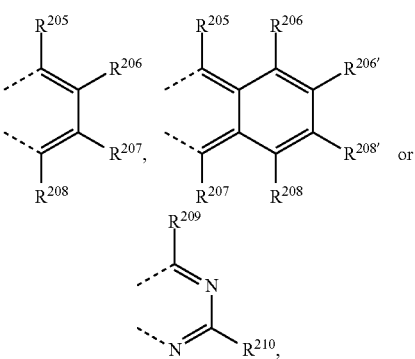

wherein $R^{206'}$, $R^{208'}$, $R^{205}$, $R^{206}$, $R^{207}$, $R^{208}$, $R^{209}$ and $R^{210}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_7$-$C_{25}$aralkyl, CN, or —CO—$R^{28}$, $R^{10}$ is H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —CO—$R^{28}$, $R^{8'}$ and $R^{9'}$ are independently of each other H, CN, —COO$R^{27}$; —CONR$^{25}$R$^{26}$, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$;

$R^{11}$ and $R^{14}$ are independently of each other hydrogen, F, $C_1$-$C_{18}$alkyl, $C_1$-$C_{18}$alkyl which is substituted by E and/or interrupted by D, $C_1$-$C_{18}$perfluoroalkyl, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, CN, or —CO—$R^{28}$, $R^{12}$, $R^{13}$, $R^{15}$ and $R^{16}$ are independently of each other H, halogen, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN or —CO—$R^{28}$, X is O, S, or NR$^{17}$, wherein $R^{17}$ is $C_6$-$C_{18}$aryl; $C_2$-$C_{20}$heteroaryl; $C_6$-$C_{18}$aryl, or $C_2$-$C_{20}$heteroaryl, which are substituted by $C_1$-$C_{18}$alkyl, $C_1$-$C_{18}$perfluoroalkyl, —N($C_6$-$C_{18}$aryl)$_2$, or $C_1$-$C_{18}$alkoxy; $C_1$-$C_{18}$alkyl; or $C_1$-$C_{18}$alkyl which is interrupted by —O—;

or two substituents $R^1$ and $R^2$, $R^4$ and $R^6$, $R^{11}$ and $R^{12}$, and/or $R^{14}$ and $R^{16}$, $R^2$ and $R^3$, $R^5$ and $R^6$, $R^{12}$ and $R^{13}$, and/or $R^{15}$ and $R^{16}$, which are adjacent to each other, together form a group

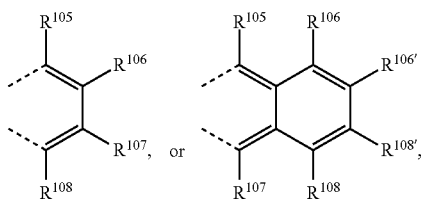

or two substituents $R^{15}$ and $R^{13}$, and/or $R^5$ and $R^3$, which are adjacent to each other, together form a group

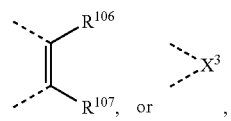

wherein $X^3$ is O, S, C($R^{119}$)($R^{120}$), or NR$^{17}$, wherein $R^{17}$ is as defined above, $R^{105}$, $R^{106}$, $R^{107}$, $R^{108}$, $R^{106'}$ and $R^{108'}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $R^{119}$ and $R^{120}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{119}$ and $R^{120}$ together form a group of formula =C$R^{121}$R$^{122}$, wherein $R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—$R^{127}$, and $R^{127}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, D is —CO—; —COO—; —S—; —SO—; —SO$_2$—; —O—; —NR$^{25}$—; —SiR$^{30}$R$^{31}$—; —POR$^{32}$—; —CR$^{23}$=CR$^{24}$—; or —C≡C—; and E is —OR$^{29}$; —SR$^{29}$; —NR$^{25}$R$^{26}$; —COR$^{28}$; —COOR$^{27}$; —CONR$^{25}$R$^{26}$; —CN; or halogen; G is E, $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, wherein $R^{23}$, $R^{24}$, $R^{25}$ and $R^{26}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or $R^{25}$ and $R^{26}$ together form a five or six membered ring, $R^{27}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{28}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{29}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{30}$ and $R^{31}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{32}$ is $C_1$-$C_{18}$alkyl, $C_6$-$C_{18}$aryl, or $C_6$-$C_{18}$aryl, which is substituted by $C_1$-$C_{18}$alkyl, and $Z^1$ and $Z^2$ are as defined in claim 1.

3. A compound of the formula X, XI, XII, XVI, XVII or XVIII, according to claim 2, wherein $R^1$ and $R^4$ are hydrogen, $R^2$, $R^3$, $R^5$ and $R^6$ are independently of each other H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, $C_7$-$C_{25}$aralkyl, or a group —$X^2$—$R^{18}$, $R^8$ and $R^9$ are independently of each other H, CN, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, or a group —$X^2$—$R^{18}$; or two substituents $R^2$ and $R^3$ and/or $R^5$ and $R^6$, which are adjacent to each other, together form a group

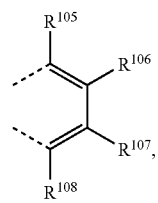

or two substituents $R^5$ and $R^3$, which are adjacent to each other, together form a group

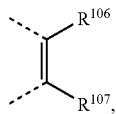

wherein $R^{105}$, $R^{106}$, $R^{107}$ and —$R^{108}$ are independently of each other H, or $C_1$-$C_8$alkyl, or $R^8$ and $R^9$ together form a group

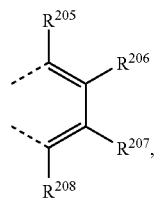 or 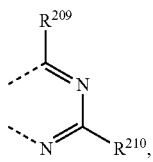

wherein $R^{205}$, $R^{206}$, $R^{207}$, $R^{208}$, $R^{209}$ and $R^{210}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $C_1$-$C_{18}$perfluoroalkyl, $R^{10}$ is H, $C_6$-$C_{18}$aryl, which can be substituted by G, $C_2$-$C_{18}$heteroaryl, which can be substituted by G, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is substituted by E and/or interrupted by D, or a group —$X^2$—$R^{18}$, wherein $X^2$ is a as $C_6$-$C_{12}$aryl or $C_6$-$C_{12}$heteroaryl spacer, which can be substituted one or more times with $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, and $R^{18}$ is H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, or —$NR^{25}R^{26}$;

D is —CO—; —COO—; —S—; —SO—; —$SO_2$—; —O—; —$NR^{25}$—; —$CR^{23}$=$CR^{24}$—; or —C≡C—; wherein $R^{23}$, $R^{24}$, $R^{25}$ and $R^{26}$ are independently of each other H; $C_6$-$C_{18}$aryl; $C_6$-$C_{18}$aryl which is substituted by $C_1$-$C_8$alkyl, or $C_1$-$C_8$alkoxy; $C_1$-$C_8$alkyl; or $C_1$-$C_8$alkyl which is interrupted by —O—, or $R^{25}$ and $R^{26}$ together form a five or six membered ring.

4. A compound according to claim 2 having the formula

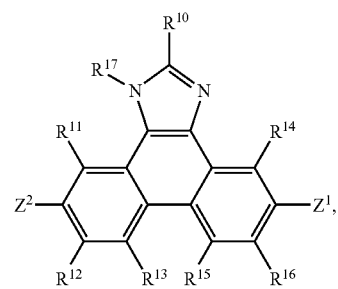

(XIIa)

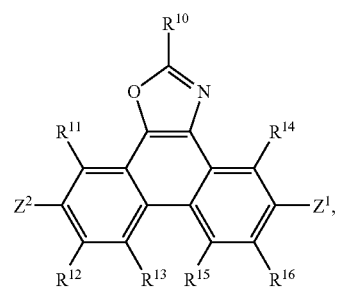

(XIIb)

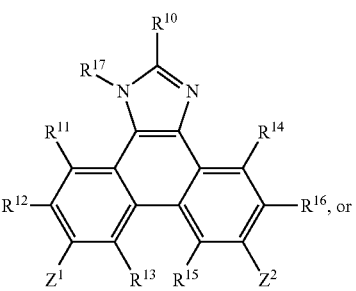

(XVIIIa)

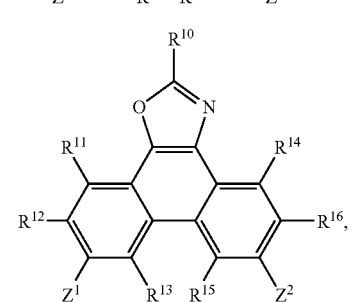

(XVIIIb)

wherein $R^{19}$ is H, $C_6$-$C_{18}$aryl, which can be substituted by G, $C_2$-$C_{18}$heteroaryl, which can be substituted by G, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is substituted by E and/or interrupted by D, or a group —$X^2$—$R^{'8}$, wherein $X^2$ is a $C_6$-$C_{12}$aryl or $C_6$-$C_{12}$heteroaryl spacer which can be substituted one or more times with $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, and $R^{18}$ is H, $C_1$-$C_{18}$alkyl, $C_1$-$C_{18}$alkyl which is interrupted by D, $C_1$-$C_{18}$perfluoroalkyl, $C_1$-$C_{18}$alkoxy, $C_1$-$C_{18}$alkoxy which is interrupted by D, or —$NR^{25}R^{26}$;

$R^{11}$ and $R^{14}$ are hydrogen, $R^{12}$, $R^{13}$, $R^{15}$ and $R^{16}$ are hydrogen, R¹⁷ is $C_6$-$C_{18}$aryl; $C_6$-$C_{18}$aryl which is substituted by $C_1$-$C_{18}$alkyl, $C_1$-$C_{18}$perfluoroalkyl, —N($C_6$-$C_{18}$aryl)$_2$, or $C_1$-$C_{18}$alkoxy; $C_1$-$C_{18}$alkyl; or $C_1$-$C_{18}$alkyl which is interrupted by —O—; or two substituents R⁵ and R³, R¹² and R¹³, and/or R¹⁵ and R¹⁶, which are adjacent to each other, together form a group

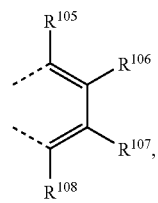

or two substituents R¹⁵ and R¹³, which are adjacent to each other, together form a group

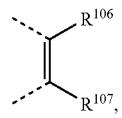

wherein R¹⁰⁵, R¹⁰⁶, R¹⁰⁷ and R¹⁰⁸ are independently of each other H, or $C_1$-$C_8$alkyl, D is —S—; —O—; or —NR²⁵—;

E is —OR²⁹; —SR²⁹; —NR²⁵R²⁶; —CN; or F; G is E, $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, wherein R²⁵ and R²⁶ are independently of each other H; $C_6$-$C_{18}$aryl; $C_6$-$C_{18}$aryl which is substituted by $C_1$-$C_8$alkyl, or $C_1$-$C_8$alkoxy; $C_1$-$C_8$alkyl; or $C_1$-$C_8$alkyl which is interrupted by —O—, or R²⁵ and R²⁶ together form a five or six membered ring, and R²⁹ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—.

5. A compound according to claim 2, wherein

Z¹ and Z² are independently of each other a group

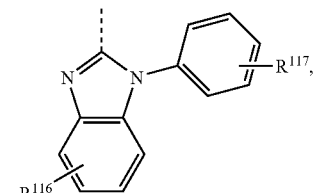

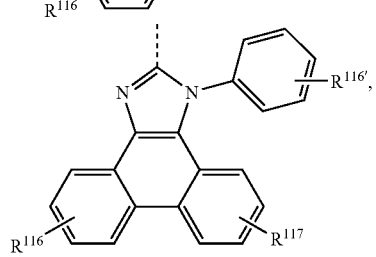

-continued

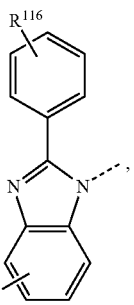

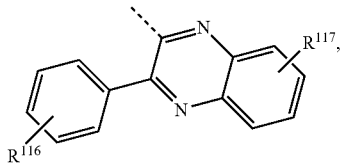

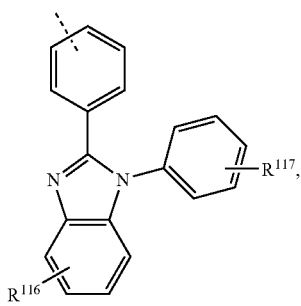

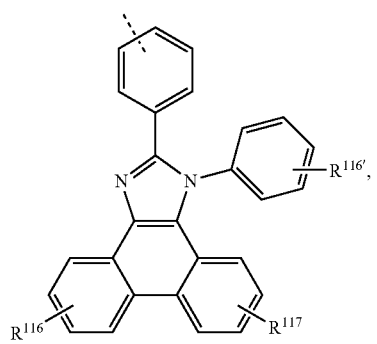

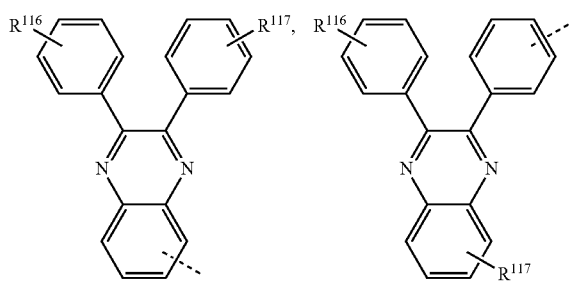

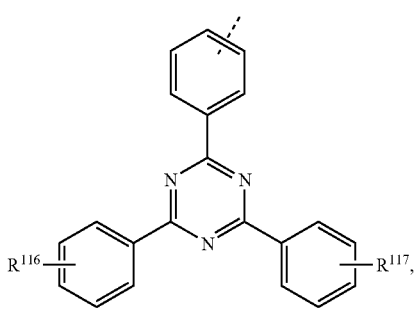

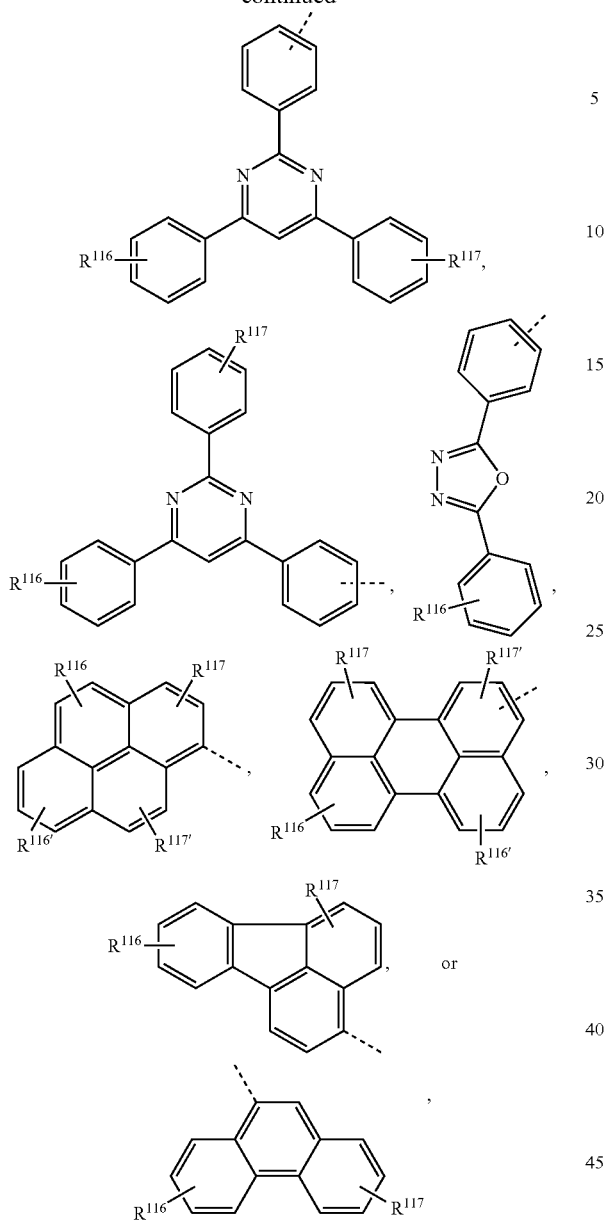

wherein $R^{116}$, $R^{116'}$, $R^{117}$ and $R^{117'}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{127}$, —C(=O)O$R^{127}$, or —C(=O)N$R^{127}R^{126}$, or substituents $R^{116}$, $R^{117}$ and $R^{117'}$, which are adjacent to each other, can form a ring, $R^{126}$ and $R^{127}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, and wherein at least one of $Z^1$ and $Z^2$ is an electron deficient heteroaryl group.

6. A compound of formula:

| Compound | $Z^1 = Z^2$ |
|---|---|

[structure with $Z^1$ and $Z^2$ substituents on a pyrazine-fused polycyclic system]

| A1 | HE-1 |
| A2 | HE-2 |
| A3 | HE-2 |
| A4 | HE-4 |
| A5 | HE-5 |
| A6 | HE-6 |
| A7 | HE-7 |
| A8 | HE-8 |
| A9 | HE-9 |
| A12 | AR-1 |
| A13 | AR-2 |
| A14 | AR-3 |
| A15 | AR-4 |
| A16 | SR-1 |

[structure with $Z^1$ and $Z^2$ substituents on a pyrazine-fused polycyclic system]

| B1 | HE-1 |
| B2 | HE-2 |
| B3 | HE-2 |
| B4 | HE-4 |
| B5 | HE-5 |
| B6 | HE-6 |
| B7 | HE-7 |
| B8 | HE-8 |
| B11 | HE-11 |
| B12 | AR-1 |
| B13 | AR-2 |
| B14 | AR-3 |
| B15 | AR-4 |
| B16 | SR-1 |

[structure with diphenyl-substituted pyrazine-fused polycyclic system with $Z^1$ and $Z^2$]

| C1 | HE-1 |
| C2 | HE-2 |
| C3 | HE-2 |
| C4 | HE-4 |
| C5 | HE-5 |
| C6 | HE-6 |
| C7 | HE-7 |

-continued
| Compound | Z¹ = Z² |
|---|---|
| C8 | HE-8 |
| C9 | HE-9 |
| C12 | AR-1 |
| C13 | AR-2 |
| C14 | AR-3 |
| C15 | AR-4 |
| C16 | SR-1 |
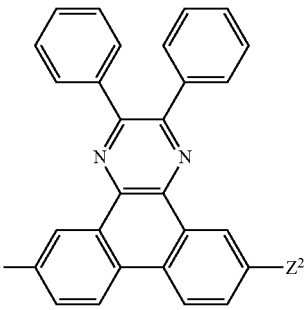
| D1 | HE-1 |
|---|---|
| D2 | HE-2 |
| D3 | HE-2 |
| D4 | HE-4 |
| D5 | HE-5 |
| D6 | HE-6 |
| D7 | HE-7 |
| D8 | HE-8 |
| D9 | HE-9 |
| D12 | AR-1 |
| D13 | AR-2 |
| D14 | AR-3 |
| D15 | AR-4 |
| D16 | SR-1 |
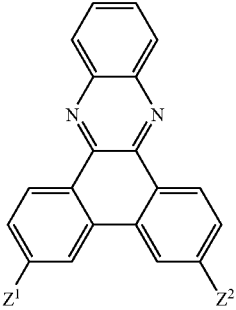
| E1 | HE-1 |
|---|---|
| E2 | HE-2 |
| E3 | HE-2 |
| E4 | HE-4 |
| E5 | HE-5 |
| E6 | HE-6 |
| E7 | HE-7 |
| E8 | HE-8 |
| E9 | HE-9 |
| E12 | AR-1 |
| E13 | AR-2 |
| E14 | AR-3 |
| E15 | AR-4 |
| E16 | SR-1 |
-continued
| Compound | Z¹ = Z² |
|---|---|
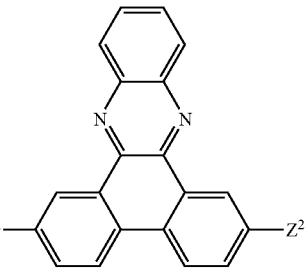
| F1 | HE-1 |
|---|---|
| F2 | HE-2 |
| F3 | HE-2 |
| F4 | HE-4 |
| F5 | HE-5 |
| F6 | HE-6 |
| F7 | HE-7 |
| F8 | HE-8 |
| F9 | HE-9 |
| F12 | AR-1 |
| F13 | AR-2 |
| F14 | AR-3 |
| F15 | AR-4 |
| F16 | SR-1 |
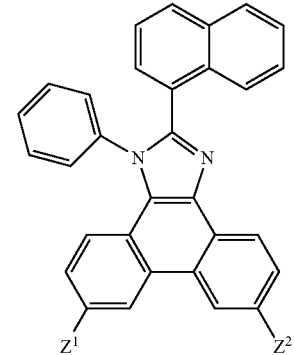
| G1 | HE-1 |
|---|---|
| G2 | HE-2 |
| G3 | HE-2 |
| G4 | HE-4 |
| G5 | HE-5 |
| G6 | HE-6 |
| G7 | HE-7 |
| G8 | HE-8 |
| G9 | HE-9 |
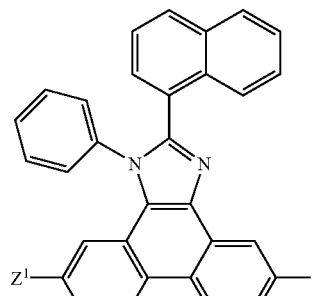
| H1 | HE-1 |
|---|---|
| H2 | HE-2 |
| H3 | HE-2 |
| H4 | HE-4 |
| H5 | HE-5 |

-continued
| Compound | $Z^1 = Z^2$ |
|---|---|
| H6 | HE-6 |
| H7 | HE-7 |
| H8 | HE-8 |
| H9 | HE-9 |
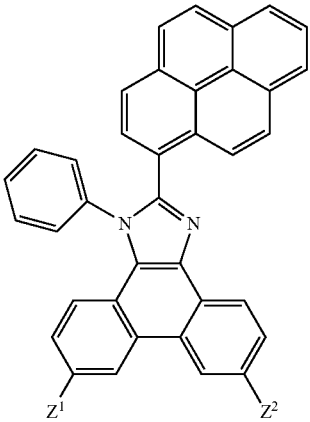
| I1 | HE-1 |
| I2 | HE-2 |
| I3 | HE-2 |
| I4 | HE-4 |
| I5 | HE-5 |
| I6 | HE-6 |
| I7 | HE-7 |
| I8 | HE-8 |
| I9 | HE-9 |
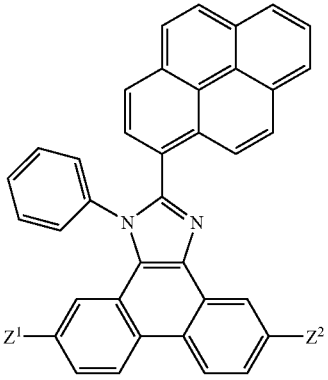
| J1 | HE-1 |
| J2 | HE-2 |
| J3 | HE-2 |
| J4 | HE-4 |
| J5 | HE-5 |
| J6 | HE-6 |
| J7 | HE-7 |
| J8 | HE-8 |
| J9 | HE-9 |
-continued
| Compound | $Z^1 = Z^2$ |
|---|---|
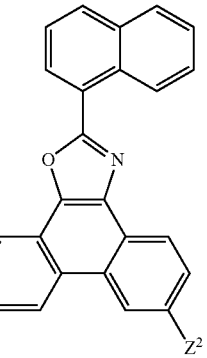
| K1 | HE-1 |
| K2 | HE-2 |
| K3 | HE-2 |
| K4 | HE-4 |
| K5 | HE-5 |
| K6 | HE-6 |
| K7 | HE-7 |
| K8 | HE-8 |
| K9 | HE-9 |
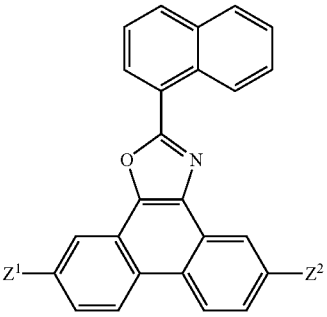
| L1 | HE-1 |
| L2 | HE-2 |
| L3 | HE-2 |
| L4 | HE-4 |
| L5 | HE-5 |
| L6 | HE-6 |
| L7 | HE-7 |
| L8 | HE-8 |
| L9 | HE-9 |
wherein HE-1 is
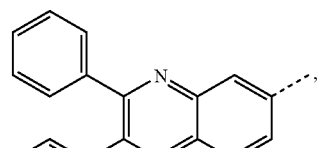
HE-2 is
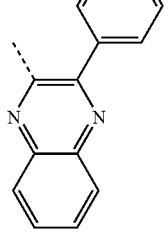

| Compound | $Z^1 = Z^2$ |
|---|---|
| HE-3 is | 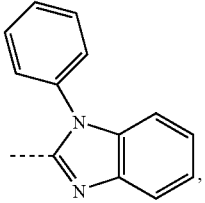 |
| HE-4 is | 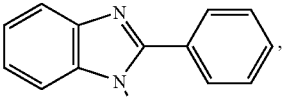 |
| HE-5 is | 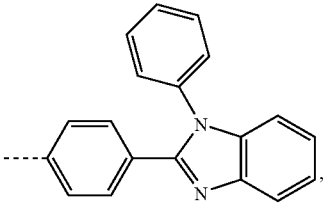 |
| HE-6 is | 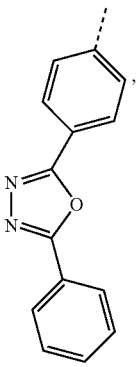 |
| HE-7 is | 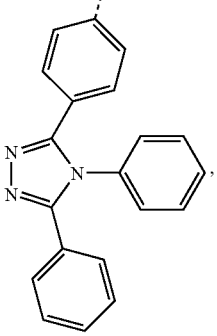 |
| HE-8 is | 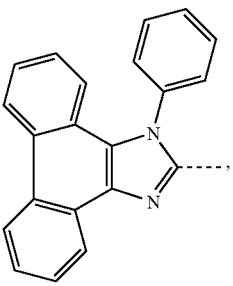 |

| Compound | $Z^1 = Z^2$ |
|---|---|
| HE-9 is | 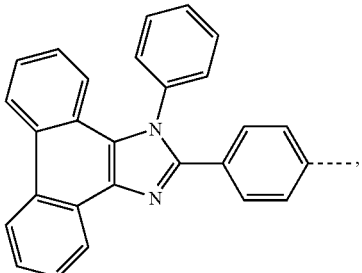 |
| AR-1 is | 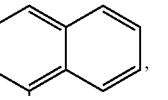 |
| AR-2 is | 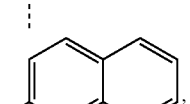 |
| AR-3 is | 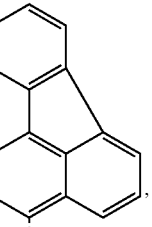 |
| AR-4 is | 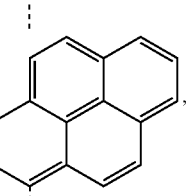 |
| and SR-1 is | 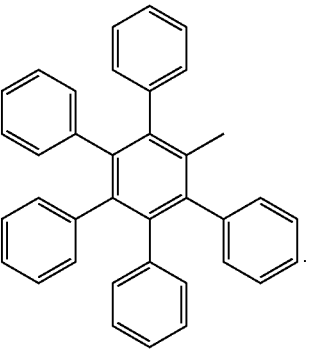 |

7. An electroluminescent device, comprising a compound of formula I according to claim 1.

8. Electroluminescent device according to claim 7, comprising a cathode, an anode, and therebetween a light emitting layer containing a host material and a phosphorescent light-emitting material wherein the host material is a compound of formula I.

9. A process for the preparation of compounds of the formula I according to claim 1, which comprises reacting a derivative of formula

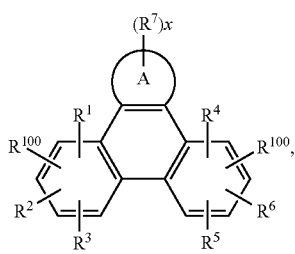

wherein $R^{100}$ stands for halogen, with boronic acid derivative E-Ar, E having the meaning of

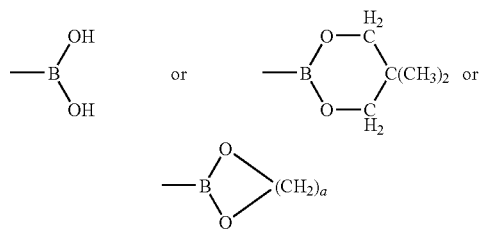

wherein a is 2 or 3, Ar has the meaning of $Z^1$, in the presence of an allylpalladium catalyst, wherein A, $Z^1$, $R^1$, $R^2$, $R^3$, $R^4$, $R^5$, $R^6$, $R^7$ and x are as defined in claim 1.

10. A compound of formula

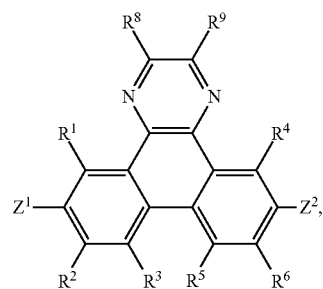
(X)

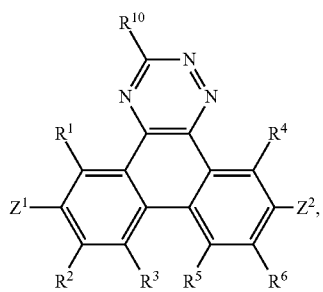
(XI)

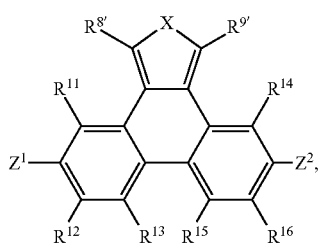
(XIII)

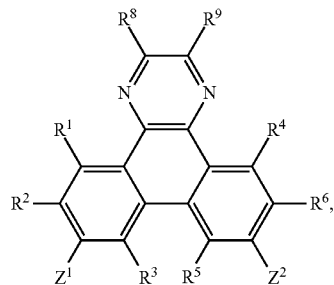
(XVI)

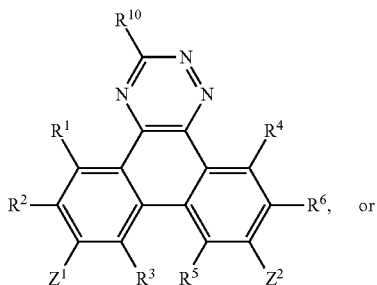
(XVII)

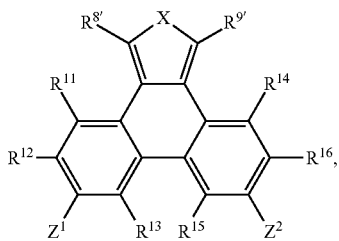
(XIX)

wherein $R^1$ and $R^4$ are independently of each other hydrogen, F, $C_1$-$C_{18}$alkyl, $C_1$-$C_{18}$alkyl which is substituted by E and/or interrupted by D, $C_1$-$C_{18}$perfluoroalkyl, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, CN, or —CO—$R^{28}$, $R^2$, $R^3$, $R^5$ and $R^6$ are independently of each other H, F, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$, $R^8$ and $R^9$ are independently of each other H, CN, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$, or $R^8$ and $R^9$ together form a group

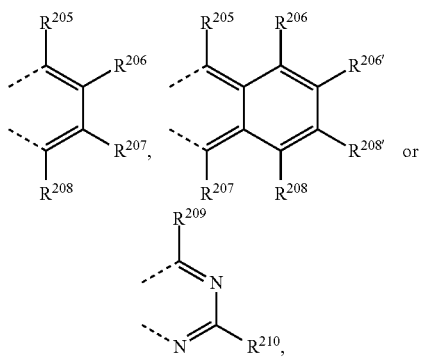

wherein $R^{206'}$, $R^{208'}$, $R^{205}$, $R^{206}$, $R^{207}$, $R^{208}$, $R^{209}$ and $R^{210}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_7$-$C_{25}$aralkyl, CN, or —CO—$R^{28}$, $R^{10}$ is H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —CO—$R^{28}$, $R^{8'}$ and $R^{9'}$ are independently of each other H, CN, —COOR$^{27}$; —CONR$^{25}$R$^{26}$, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN, or —CO—$R^{28}$;

$R^{11}$ and $R^{14}$ are independently of each other hydrogen, F, $C_1$-$C_{18}$alkyl, $C_1$-$C_{18}$alkyl which is substituted by E and/or interrupted by D, $C_1$-$C_{18}$perfluoroalkyl, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, CN, or —CO—$R^{28}$, $R^{12}$, $R^{13}$, $R^{15}$ and $R^{16}$ are independently of each other H, halogen, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, CN or —CO—$R^{28}$, X is O, S, or NR$^{17}$, wherein R$'^{17}$ is $C_6$-$C_{18}$aryl; $C_2$-$C_{20}$heteroaryl; $C_6$-$C_{18}$aryl, or $C_2$-$C_{20}$heteroaryl, which are substituted by $C_1$-$C_{18}$alkyl, $C_1$-$C_{18}$perfluoroalkyl, —N($C_6$-$C_{18}$aryl)$_2$, or $C_1$-$C_{18}$alkoxy; $C_1$-$C_{18}$alkyl; or $C_1$-$C_{18}$alkyl which is interrupted by —O—;

or two substituents $R^1$ and $R^2$, $R^4$ and $R^6$, $R^{11}$ and $R^{12}$, and/or $R^{14}$ and $R^{16}$, $R^2$ and $R^3$, $R^5$ and $R^6$, $R^{12}$ and $R^{13}$, and/or $R^{15}$ and $R^{16}$, which are adjacent to each other, together form a group

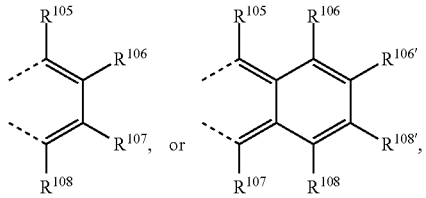

or two substituents $R^{15}$ and $R^{13}$, and/or $R^5$ and $R^3$, which are adjacent to each other, together form a group

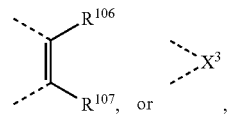

wherein $X^3$ is O, S, C($R^{119}$)($R^{121}$), or NR$^{17}$, wherein R$^{17}$ is as defined above, $R^{195}$, $R^{106}$, $R^{107}$, $R^{108}$, $R^{106'}$ and $R^{108'}$ are independently of each other H, $C_1$-$C_{18}$alkyl, $C_1$-$C_{18}$alkyl which is substituted by E and/or interrupted by D, $C_1$-$C_{18}$alkoxy, or $C_1$-$C_{18}$alkoxy which is substituted by E and/or interrupted by D, $R^{119}$ and $R^{120}$ are independently of each other $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{119}$ and $R^{120}$ together form a group of formula =CR$^{121}$R$^{122}$, wherein $R^{121}$ and $R^{122}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{119}$ and $R^{120}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or —C(=O)—R$^{127}$, and D is —CO—; —COO—; —S—; —SO—; —SO$_2$—; —O—; —NR$^{25}$—; —SiR$^{30}$R$^{31}$—; —POR$^{32}$—; —CR$^{23}$=CR$^{24}$—; or —C≡C—; and E is —OR$^{29}$; —SR$^{29}$; —NR$^{25}$R$^{26}$; —COR$^{28}$; —COOR$^{27}$; —CONR$^{25}$R$^{26}$; CN; or halogen;

G is E, $C_1$-$C_{18}$alkyl, $C_1$-$C_{18}$alkyl which is interrupted by D, $C_1$-$C_{18}$perfluoroalkyl, $C_1$-$C_{18}$alkoxy, or $C_1$-$C_{18}$alkoxy which is substituted by E and/or interrupted by D, wherein $R^{23}$, $R^{24}$, $R^{25}$ and $R^{26}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; or $R^{25}$ and $R^{26}$ together form a five or six membered ring, $R^{27}$ is $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{28}$ is H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{29}$ is $C_6$-$C_{18}$aryl; $C_6$-$C_{18}$aryl, which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{30}$ and $R^{31}$ are independently of each other $C_1$-$C_{18}$alkyl, $C_6$-$C_{18}$aryl, or $C_6$-$C_{18}$aryl, which is substituted by $C_1$-$C_{18}$alkyl, and $R^{32}$ is $C_1$-$C_{18}$alkyl, $C_6$-$C_{18}$aryl, or $C_6$-$C_{18}$aryl, which is substituted by $C_1$-$C_{18}$alkyl, and $Z^1$ and $Z^2$ are independently of each other a group

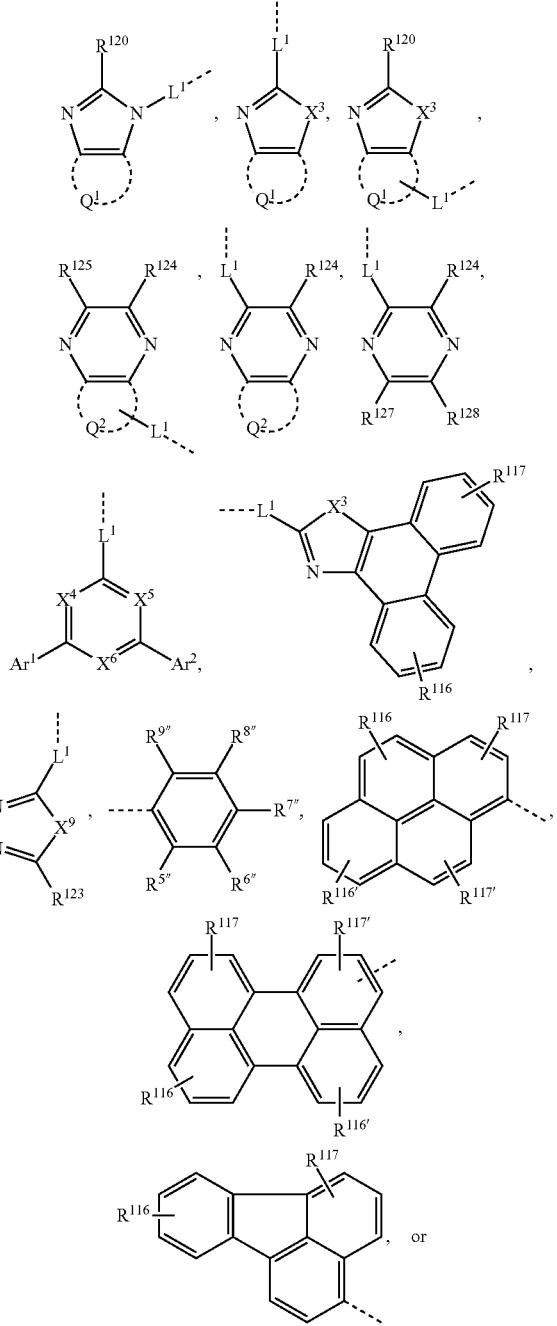

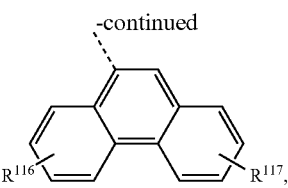

or
$Z^1$ and $Z^2$ are both

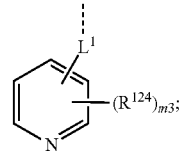

wherein $R^{5''}$ is hydrogen, or has the meaning of $R^6$, $R^{6''}$, $R^{7''}$, $R^{8''}$ and $R^{9''}$ are independently of each other $C_6$-$C_{18}$aryl; which may optionally be substituted by G; or $C_2$-$C_{20}$heteroaryl, which may optionally be substituted by G, $X^3$ represents O, S or N—$R^{121'}$, $X^9$ represents O, S or N—$R^{121'}$, $Q^1$ and $Q^2$ represents atoms necessary for forming a carbocyclic aromatic, or heterocyclic aromatic ring, which can optionally be condensed with other ring(s) to form a condensed ring, and/or can optionally be substituted by G, $R^{121'}$ is $C_6$-$C_{18}$aryl; or $C_2$-$C_{20}$heteroaryl; which can optionally be substituted by $C_1$-$C_{18}$alkyl, $C_1$-$C_{18}$perfluoroalkyl, or $C_1$-$C_{18}$alkoxy; $C_1$-$C_{18}$alkyl; or $C_1$-$C_{18}$alkyl which is interrupted by —O—;

$R^{116}$, $R^{116'}$, $R^{117}$ and $R^{117'}$ are independently of each other H, halogen, —CN, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, —C(=O)—$R^{127}$, —C(=O)O$R^{127}$, or —C(=O)N$R^{127}R^{126}$, or substituents $R^{116}$, $R^{116'}$, $R^{117}$ and $R^{117'}$, which are adjacent to each other, can form a ring, $R^{126}$ and $R^{127}$ are independently of each other $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{120}$, $R^{123}$, $R^{124}$ and $R^{125}$ are independently of each other H, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, which can optionally be substituted by G, $C_2$-$C_{20}$heteroaryl, which can optionally be substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, $R^{128}$ is H, CN, $C_1$-$C_{18}$alkyl, $C_1$-$C_{18}$alkyl which is substituted by E and/or interrupted by D, $C_1$-$C_{18}$perfluoroalkyl, $C_6$-$C_{24}$aryl, which can optionally be substituted by G, $C_2$-$C_{20}$heteroaryl, which can optionally be substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, $L^1$ is a single bond, $-(CR^{47}=CR^{48})_{m2}-$, $-(Ar^3)_{m3}-$, $-[Ar^3(Y^1)_{m1}]_{m4}-$, $-[(Y^1)_{m1}Ar^3]_{m4}-$, or $-[Ar^3(Y^2)_{m1}Ar^4]_{m4}-$, wherein $Y^1$ is $-(CR^{47}=CR^{48})-$, $Y^2$ is $NR^{49}$, O, S, C=O, C(=O)O, wherein $R^{49}$ is H; $C_6$-$C_{18}$aryl which can optionally be substituted by $C_1$-$C_{18}$alkyl, or $C_1$-$C_{18}$alkoxy; $C_1$-$C_{18}$alkyl; or $C_1$-$C_{18}$alkyl which is interrupted by $-O-$;

$R^{47}$ and $R^{48}$ are independently of each other hydrogen, fluorine, $C_1$-$C_{20}$alkyl, or $C_6$-$C_{24}$aryl, which can optionally be substituted by G, m1 is an integer of 1 to 10, m2 is an integer of 1 to 10, m3 is an integer of 1 to 5, m4 is an integer of 1 to 5, $Ar^3$ and $Ar^4$ are independently of each other arylen, or heteroarylen, which can optionally be substituted, $X^4$, $X^5$ and $X^6$ are independently of each other N, or CH, with the proviso that at least one of the substituents $X^4$, $X^5$ and $X^6$ are N, $Ar^1$ and $Ar^2$ are independently of each other $C_6$-$C_{24}$aryl, which can optionally be substituted by G, or $C_2$-$C_{20}$heteroaryl, which can optionally be substituted by G, wherein D, E and G are as defined above.

\* \* \* \* \*